US007790156B2

(12) United States Patent
Damude et al.

(10) Patent No.: US 7,790,156 B2
(45) Date of Patent: Sep. 7, 2010

(54) Δ-8 DESATURASES AND THEIR USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/099,811

(22) Filed: Apr. 9, 2008

(65) Prior Publication Data

US 2008/0254521 A1 Oct. 16, 2008

Related U.S. Application Data

(60) Provisional application No. 60/910,831, filed on Apr. 10, 2007.

(51) Int. Cl.
*A01N 63/00* (2006.01)
*A01K 48/00* (2006.01)
*C07H 21/04* (2006.01)

(52) U.S. Cl. .................. 424/93.2; 424/93.21; 536/23.2; 536/23.7; 536/23.74

(58) Field of Classification Search ................ 424/93.2, 424/93.21; 536/23.2, 23.7, 23.74
See application file for complete search history.

(56) References Cited

U.S. PATENT DOCUMENTS

| | | | | |
|---|---|---|---|---|
| 6,825,017 | B1 * | 11/2004 | Browse et al. | 435/190 |
| 7,125,672 | B2 | 10/2006 | Picataggio et al. | |
| 7,238,482 | B2 | 7/2007 | Picataggio et al. | |
| 7,256,033 | B2 | 8/2007 | Damude et al. | |
| 7,335,476 | B2 | 2/2008 | Picataggio et al. | |
| 2005/0273885 | A1 | 12/2005 | Singh et al. | |
| 2006/0035351 | A1 | 2/2006 | Zhu et al. | |
| 2006/0094092 | A1 | 5/2006 | Damude et al. | |
| 2006/0110806 | A1 | 5/2006 | Damude et al. | |
| 2006/0115881 | A1 | 6/2006 | Damude et al. | |
| 2006/0195939 | A1 | 8/2006 | Damude et al. | |
| 2007/0004016 | A1 | 1/2007 | Picataggio et al. | |
| 2007/0207528 | A1 | 9/2007 | Picataggio et al. | |
| 2008/0095915 | A1 | 4/2008 | Damude et al. | |
| 2008/0118623 | A1 | 5/2008 | Damude et al. | |
| 2008/0138868 | A1 | 6/2008 | Damude et al. | |
| 2008/0194685 | A1 | 8/2008 | Damude et al. | |
| 2008/0254192 | A1 | 10/2008 | Damude et al. | |

FOREIGN PATENT DOCUMENTS

| | | |
|---|---|---|
| WO | WO0034439 | 6/2000 |
| WO | WO2004057001 | 7/2004 |
| WO | WO2005103253 | 4/2005 |
| WO | WO 2006/012325 A1 * | 2/2006 |
| WO | WO2008073275 | 6/2008 |

OTHER PUBLICATIONS

Kaye et al., 1990, Proc. Natl. Acad. Sci. USA, vol. 87, pp. 6922-6926.*
Skolnick et al., 2000, Trends in Biotech, vol. 18, p. 34-39.*
Tomasinsig et al., 2005, Current Protein and Peptide Science, vol. 6, p. 23-34.*
Browse et al., 2004, computer printout, pp. 5-6.*
Damude et al., 2006, computer printout pp. 2-3.*
Wallis et al., Arch. Biochem. and Biophys., 365(2):307-316 (1999).
Sayanova et al. (FEBS LETT., 580:1946-1952 (2006)).
The following applications are commonly owned by DuPont and are reported herein: U.S. Appl. No. 12/244,822, filed Oct. 3, 2008 and U.S. Appl. No. 12/244,950, filed Oct. 3, 2008.
International Search Report and Written Opinion of PCT/US2008/004700 mailed Sep. 19, 2008.
International Search Report, PCT International Application No. PCT/US08/04700, Oct. 22, 2009.
Warude, Dnyaneshwar et al., Polyunsaturated Fatty Acids: Biotechnology, Critical Reviews in Biotechnology, vol. 26, 26 (2006), pp. 83-93.

* cited by examiner

*Primary Examiner*—Shin-Lin Chen
(74) *Attorney, Agent, or Firm*—Lynne M. Christenbury

(57) ABSTRACT

The present invention relates to Δ8 desaturase genes, which have the ability to convert eicosadienoic acid (EDA; 20:2 ω-6) to dihomo-γ-linolenic acid (DGLA; 20:3 ω-6) and/or eicosatrienoic acid (ETrA; 20:3 ω-3) to eicosatetraenoic acid (ETA; (20:3 ω-3). Isolated nucleic acid fragments and recombinant DNA constructs comprising such fragments encoding Δ8 desaturases along with a method of making long-chain polyunsaturated fatty acids (PUFAs) using these Δ8 desaturases in oleaginous yeast are disclosed.

8 Claims, 11 Drawing Sheets

FIG. 4A

Figure 1:
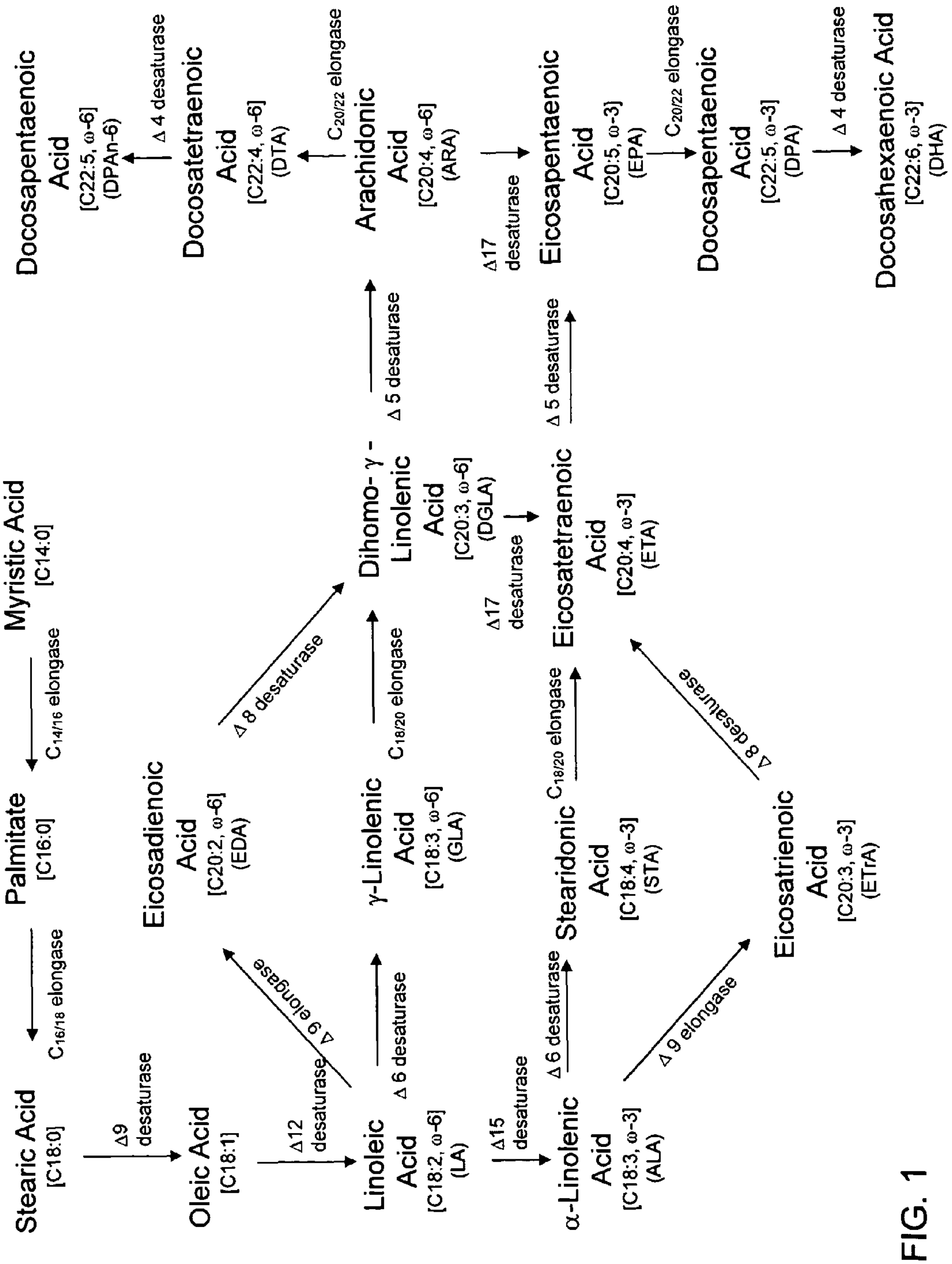

```
     M..KR.ALPLT.DG.TYDVSAW.N.HPGGA.IIENY.GRDATD.FMVMHS Consensus #1
              10        20        30        40        50
1    M-VKRPALPLTVDGVTYDVSAWLNHHPGGADIIENYRGRDATDVFMVMHS EaD8Des1 (SEQ ID NO21).pro
1    M-VKRPALPLTVDGVTYDVSAWLNHHPGGADIIENYRGRDATDVFMVMHS EaD8Des2 (SEQ ID NO22).pro
1    M-VKRPALPLTVDGVTYDVSAWLNHHPGGADIIENYRGRDATDVFMVMHS EaD8Des3 (SEQ ID NO23).pro
1    M-VKRPALPLTVDGVTYDVSAWLNHHPGGADIIENYRGRDATDVFMVMHS EaD8Des4 (SEQ ID NO24).pro
1    MKSKRQALPLTIDGTTYDVSAWVNFHPGGAEIIENYQGRDATDAFMVMHS corrected EgD8 (SEQ ID NO25).pro

     ..A..KL.RMP...PSS.L...PP.....E.QEDFRKLR.ELIA.GMFDA Consensus #1
              60        70        80        90       100
50   ENAVSKLRRMPIMEPSSPLTPTPPKPNSDEPQEDFRKLRDELIAAGMFDA EaD8Des1 (SEQ ID NO21).pro
50   ENAVSKLRRMPIMEPSSPLTPTPPKPNSDEPQEDFRKLRDELIAAGMFDA EaD8Des2 (SEQ ID NO22).pro
50   ENAVSKLRRMPIMEPSSPLTPTPPKPNSDEPQEDFRKLRDELIAAGMFDA EaD8Des3 (SEQ ID NO23).pro
50   ENAVSKLRRMPIMEPSSPLTPTPPKPNSDEPQEDFRKLRDELIAAGMFDA EaD8Des4 (SEQ ID NO24).pro
51   QEAFDKLKRMPKINPSSEL---PPQAAVNEAQEDFRKLREELIATGMFDA corrected EgD8 (SEQ ID NO25).pro

     SP.WY.YK...TLGLGVL...LM.Q...Y..GA..LG.H.QQMGWLSHDI Consensus #1
             110       120       130       140       150
100  SPMWYAYKTLTTLGLGVLAVLLMTQWHWYLVGAIVLGIHFQQMGWLSHDI EaD8Des1 (SEQ ID NO21).pro
100  SPMWYAYKTLSTLGLGVLAVLLMTQWHWYLVGAIVLGIHFQQMGWLSHDI EaD8Des2 (SEQ ID NO22).pro
100  SPMWYAYKTLSTLGLGVLAVLLMTQWHWYLVGAIVLGIHFQQMGWLSHDI EaD8Des3 (SEQ ID NO23).pro
100  SPMWYAYKTLSTLGLGVLAVLLMTQWHWYLVGAIVLGIHFQQMGWLSHDI EaD8Des4 (SEQ ID NO24).pro
98   SPLWYSYKISTTLGLGVLGYFLMVQYQMYFIGAVLLGMHYQQMGWLSHDI corrected EgD8 (SEQ ID NO25).pro
```

FIG. 4B

```
    CHHQ.FK.R..NN..GL.FGN.LQGFSVTWWKDRHNAHHSATNVQGHDPD Consensus #1
             160       170       180       190       200
150 CHHQLFKDRSINNAIGLLFGNVLQGFSVTWWKDRHNAHHSATNVQGHDPD EaD8Des1 (SEQ ID NO21).pro
150 CHHQLFKDRSINNAIGLLFGNVLQGFSVTWWKDRHNAHHSATNVQGHDPD EaD8Des2 (SEQ ID NO22).pro
150 CHHQLFKDRSINNAIGLLFGNVLQGFSVTWWKDRHNAHHSATNVQGHDPD EaD8Des3 (SEQ ID NO23).pro
150 CHHQLFKDRSINNAIGLLFGNVLQGFSVTWWKDRHNAHHSATNVQGHDPD EaD8Des4 (SEQ ID NO24).pro
148 CHHQTFKNRNWNNLVGLVFGNGLQGFSVTWWKDRHNAHHSATNVQGHDPD corrected EgD8 (SEQ ID NO25).pro

    IDNLPLLAWS..DV.RA.P.SR..I..QQYYF..IC.LLRFIWCFQS..T Consensus #1
             210       220       230       240       250
200 IDNLPLLAWSKEDVERAGPFSRRMIKYQQYYFFFICALLRFIWCFQSIHT EaD8Des1 (SEQ ID NO21).pro
200 IDNLPLLAWSKEDVERAGPFSRRIIKYQQYYFFFICALLRFIWCFQSIHT EaD8Des2 (SEQ ID NO22).pro
200 IDNLPLLAWSKEDVERAGPFSRRMIKYQQYYFFFICALLRFIWCFQSIHT EaD8Des3 (SEQ ID NO23).pro
200 IDNLPLLAWSKEDVERAGPFSRRMIKYQQYYFFFICALLRFIWCFQSIHT EaD8Des4 (SEQ ID NO24).pro
198 IDNLPLLAWSEDDVTRASPISRKLIQFQQYYFLVICILLRFIWCFQSVLT corrected EgD8 (SEQ ID NO25).pro

    ...LKDR.NQ.YR.QY.KE..GLALHW.LK.LF..F.MPS.LT.L.VFFV Consensus #1
             260       270       280       290       300
250 AKGLKDRSNQYYRRQYEKESVGLALHWGLKALFYYFYMPSFLTGLMVFFV EaD8Des1 (SEQ ID NO21).pro
250 ATGLKDRSNQYYRRQYEKESVGLALHWGLKALFYYFYMPSFLTGLMVFFV EaD8Des2 (SEQ ID NO22).pro
250 ATGLKDRSNQYYRRQYEKESVGLALHWGLKALFYYFYMPSFLTGLMVFFV EaD8Des3 (SEQ ID NO23).pro
250 AKGLKDRSNQYYRRQYEKESVGLALHWGLKALFYYFYMPSFLTGLMVFFV EaD8Des4 (SEQ ID NO24).pro
248 VRSLKDRDNQFYRSQYKKEAIGLALHWTLKTLFHLFFMPSILTSLLVFFV corrected EgD8 (SEQ ID NO25).pro
```

FIG. 4C

```
    SEL.GGFGIAIVVFMNHYPLEKI.DSVWDGHGF..GQIHETMN..RG..T Consensus #1
              310       320       330       340       350
300 SELLGGFGIAIVVFMNHYPLEKIQDSVWDGHGFCAGQIHETMNVQRGLVT EaD8Des1 (SEQ ID NO21).pro
300 SELLGGFGIAIVVFMNHYPLEKIQDSVWDGHGFCAGQIHETMNVQRGLVT EaD8Des2 (SEQ ID NO22).pro
300 SELLGGFGIAIVVFMNHYPLEKIQDSVWDGHGFCAGQIHETMNVQRGLVT EaD8Des3 (SEQ ID NO23).pro
300 SELLGGFGIAIVVFMNHYPLEKIQDSVWDGHGFCAGQIHETMNVQRGLVT EaD8Des4 (SEQ ID NO24).pro
298 SELVGGFGIAIVVFMNHYPLEKIGDSVWDGHGFSVGQIHETMNIRRGIIT corrected EgD8 (SEQ ID NO25).pro

    DWFFGGLNYQIEHHLWPTLPRHNLTA.S..VEQLC.KHNLPYR.P...EG Consensus #1
              360       370       380       390       400
350 DWFFGGLNYQIEHHLWPTLPRHNLTAASIKVEQLCKKHNLPYRSPPMLEG EaD8Des1 (SEQ ID NO21).pro
350 DWFFGGLNYQIEHHLWPTLPRHNLTAASIKVEQLCKKHNLPYRSPPMLEG EaD8Des2 (SEQ ID NO22).pro
350 DWFFGGLNYQIEHHLWPTLPRHNLTAASIKVEQLCKKHNLPYRSPPMLEG EaD8Des3 (SEQ ID NO23).pro
350 DWFFGGLNYQIEHHLWPTLPRHNLTAASIKVEQLCKKHNLPYRSPPMLEG EaD8Des4 (SEQ ID NO24).pro
348 DWFFGGLNYQIEHHLWPTLPRHNLTAVSYQVEQLCQKHNLPYRNPLPHEG corrected EgD8 (SEQ ID NO25).pro

    ..IL..YL..FARM..K..A.KA.                           Consensus #1
              410       420
400 VGILISYLGTFARMVAK--ADKA                            EaD8Des1 (SEQ ID NO21).pro
400 VGILISYLGTFARMVAK--ADKA                            EaD8Des2 (SEQ ID NO22).pro
400 VGILISYLGTFARMVAK--ADKA                            EaD8Des3 (SEQ ID NO23).pro
400 VGILISYLGTFARMVAK--ADKA                            EaD8Des4 (SEQ ID NO24).pro
398 LVILLRYLAVFARMAEKQPAGKAL                           corrected EgD8 (SEQ ID NO25).pro
```

FIG. 6

| Event | Fatty Acid | Fatty acid composition (wt.%) 16:0 | 16:1 | 18:0 | 18:1 | LA | ALA | 20:1 | EDA | DGLA | ERA | ETA | 24:0 | 24:1 | C20 % delta-8 desat | Ave. C20 % delta-8 desat | Ratio (EDA/ERA) % desat |
|---|---|---|---|---|---|---|---|---|---|---|---|---|---|---|---|---|---|
| pY175-1 | EDA | 13.1 | 10.0 | 1.2 | 20.4 | 50.8 | 0.1 | 0.2 | 1.5 | 1.6 | 0.0 | 0.0 | 0.2 | 1.0 | 51.4 | 52.2 | 1.2 |
| Y175-2 | EDA | 13.5 | 9.8 | 1.2 | 21.0 | 50.7 | 0.1 | 0.1 | 1.3 | 1.5 | 0.0 | 0.0 | 0.3 | 0.5 | 52.6 | | |
| Y175-2 | EDA | 13.5 | 9.7 | 1.2 | 21.1 | 50.8 | 0.1 | 0.2 | 1.3 | 1.4 | 0.0 | 0.0 | 0.2 | 0.4 | 52.6 | | |
| Y176-1 | EDA | 13.6 | 9.5 | 1.1 | 18.3 | 52.6 | 0.1 | 0.1 | 1.8 | 1.8 | 0.0 | 0.0 | 0.2 | 0.9 | 50.7 | 52.2 | 1.2 |
| Y176-2 | EDA | 13.3 | 10.6 | 1.1 | 20.7 | 50.8 | 0.1 | 0.1 | 1.1 | 1.3 | 0.0 | 0.0 | 0.2 | 0.6 | 53.0 | | |
| Y176-3 | EDA | 13.2 | 10.6 | 1.1 | 21.1 | 50.5 | 0.1 | 0.1 | 1.1 | 1.3 | 0.0 | 0.0 | 0.2 | 0.7 | 53.0 | | |
| Y177-1 | EDA | 13.3 | 10.3 | 1.1 | 19.2 | 52.3 | 0.1 | 0.1 | 1.4 | 1.6 | 0.0 | 0.0 | 0.1 | 0.3 | 52.6 | 52.3 | 1.1 |
| Y177-2 | EDA | 13.3 | 10.1 | 1.2 | 21.5 | 50.4 | 0.1 | 0.1 | 1.2 | 1.3 | 0.0 | 0.0 | 0.2 | 0.6 | 52.7 | | |
| Y177-3 | EDA | 13.3 | 10.2 | 1.1 | 22.6 | 49.7 | 0.1 | 0.1 | 1.2 | 1.2 | 0.0 | 0.0 | 0.2 | 0.2 | 51.5 | | |
| Y178-1 | EDA | 13.5 | 9.6 | 1.2 | 21.8 | 50.5 | 0.1 | 0.2 | 1.4 | 1.3 | 0.0 | 0.0 | 0.1 | 0.3 | 47.5 | 49.2 | 1.1 |
| Y178-2 | EDA | 13.7 | 9.2 | 1.2 | 19.5 | 51.9 | 0.1 | 0.2 | 1.9 | 1.8 | 0.0 | 0.0 | 0.1 | 0.3 | 48.4 | | |
| Y178-3 | EDA | 13.6 | 9.8 | 1.2 | 22.2 | 49.8 | 0.1 | 0.2 | 1.3 | 1.4 | 0.0 | 0.0 | 0.1 | 0.3 | 51.5 | | |
| Y175-1 | ERA | 12.2 | 8.8 | 1.3 | 21.9 | 40.8 | 7.2 | 0.1 | 0.1 | 0.1 | 3.8 | 3.1 | 0.1 | 0.5 | 44.3 | 44.3 | |
| Y175-2 | ERA | 12.1 | 9.2 | 1.3 | 21.4 | 40.9 | 7.2 | 0.1 | 0.1 | 0.1 | 3.9 | 3.1 | 0.1 | 0.4 | 44.1 | | |
| Y175-3 | ERA | 12.1 | 9.1 | 1.2 | 21.2 | 41.1 | 7.3 | 0.1 | 0.1 | 0.1 | 3.9 | 3.2 | 0.1 | 0.3 | 44.5 | | |
| Y176-1 | ERA | 12.1 | 8.8 | 1.2 | 20.1 | 41.1 | 8.1 | 0.1 | 0.1 | 0.1 | 4.3 | 3.3 | 0.1 | 0.5 | 43.6 | 44.7 | |
| Y176-2 | ERA | 12.3 | 9.6 | 1.3 | 23.0 | 40.5 | 6.3 | 0.1 | 0.1 | 0.1 | 3.3 | 2.7 | 0.2 | 0.3 | 45.2 | | |
| Y176-3 | ERA | 12.0 | 9.6 | 1.3 | 21.0 | 41.3 | 7.4 | 0.1 | 0.1 | 0.1 | 3.7 | 3.0 | 0.0 | 0.4 | 45.3 | | |
| Y177-1 | ERA | 12.1 | 9.5 | 1.2 | 22.4 | 40.4 | 7.1 | 0.1 | 0.1 | 0.1 | 3.5 | 3.0 | 0.1 | 0.3 | 45.7 | 45.5 | |
| Y177-2 | ERA | 12.0 | 9.9 | 1.2 | 21.3 | 40.3 | 7.6 | 0.1 | 0.1 | 0.1 | 3.6 | 3.0 | 0.1 | 0.6 | 45.1 | | |
| Y177-3 | ERA | 12.0 | 9.8 | 1.2 | 20.1 | 40.6 | 7.7 | 0.1 | 0.1 | 0.1 | 3.8 | 3.2 | 0.1 | 1.0 | 45.9 | | |
| Y178-1 | ERA | 11.7 | 9.8 | 1.0 | 19.5 | 42.6 | 8.3 | 0.1 | 0.1 | 0.1 | 3.7 | 2.7 | 0.1 | 0.4 | 42.3 | 44.1 | |
| Y178-2 | ERA | 12.0 | 9.8 | 1.2 | 20.8 | 40.9 | 7.8 | 0.1 | 0.1 | 0.1 | 3.7 | 3.0 | 0.1 | 0.3 | 44.6 | | |
| Y178-3 | ERA | 12.2 | 10.2 | 1.2 | 24.4 | 40.4 | 5.6 | 0.1 | 0.1 | 0.1 | 2.8 | 2.3 | 0.2 | 0.4 | 45.5 | | |

SEQUENCE LISTING

```
<160> NUMBER OF SEQ ID NOS: 51

<210> SEQ ID NO 1
<211> LENGTH: 604
<212> TYPE: DNA
<213> ORGANISM: Euglena anabaena

<400> SEQUENCE: 1

gccaactttg tacaaaaaag ttggattttt tttcggccca cgatctcaca tggtgaaaag      60

gccagcactt ccgctgaccg ttgatggtgt cacctatgat gtgtctgcct ggttgaacca     120

tcatccaggg ggtgctgaca tcattgagaa ctaccgcggt cgtgatgcca ctgatgtctt     180

tatggttatg cactctgaaa atgctgtgag taaactaaga aggatgccta tcatggaacc     240

atcatctcca ctgacgccta cgccaccgaa acccaactca gacgaaccgc aggaggattt     300

ccgcaagctc cgagatgagc tcatcgcagc aggaatgttc gacgcatcac cgatgtggta     360

cgcatataag acgctcacta cgctgggcct cggggtcctc gcggtgctat tgatgaccca     420

gtggcactgg tacctcgtcg gggcaatcgt gttgggcatt cacttccaac aaatgggttg     480

gttgtcgcac gatatctgcc accatcagct gttcaaggac cgatcgatca acaacgccat     540

cggcttgctt ttcgggaacg tcttgcaagg gttctctgtg acctggtgga aggacagtca     600

caac                                                                  604


<210> SEQ ID NO 2
<211> LENGTH: 1263
<212> TYPE: DNA
<213> ORGANISM: Euglena gracilis
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(1263)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: U.S. 7,256,033
<311> PATENT FILING DATE: 2005-06-24
<312> PUBLICATION DATE: 2007-08-14
<313> RELEVANT RESIDUES IN SEQ ID NO: (1)..(1263)

<400> SEQUENCE: 2

atgaagtcaa agcgccaagc gcttcccctt acaattgatg gaacaacata tgatgtgtct      60
```

-continued

```
gcctgggtca atttccaccc tggtggtgcg gaaattatag agaattacca aggaagggat    120

gccactgatg ccttcatggt tatgcactct caagaagcct tcgacaagct caagcgcatg    180

cccaaaatca atcccagttc tgagttgcca ccccaggctg cagtgaatga agctcaagag    240

gatttccgga agctccgaga agagttgatc gcaactggca tgtttgatgc ctcccccctc    300

tggtactcat acaaaatcag caccacactg ggccttggag tgctgggtta tttcctgatg    360

gttcagtatc agatgtattt cattggggca gtgttgcttg ggatgcacta tcaacagatg    420

ggctggcttt ctcatgacat ttgccaccac cagactttca agaaccggaa ctggaacaac    480

ctcgtgggac tggtatttgg caatggtctg caaggttttt ccgtgacatg gtggaaggac    540

agacacaatg cacatcattc ggcaaccaat gttcaagggc acgaccctga tattgacaac    600

ctcccccctct tagcctggtc tgaggatgac gtcacacggg cgtcaccgat ttcccgcaag    660

ctcattcagt tccagcagta ctatttcttg gtcatctgta tcttgttgcg gttcatttgg    720

tgtttccaga gcgtgttgac cgtgcgcagt ttgaaggaca gagataacca attctatcgc    780

tctcagtata agaaggaggc cattggcctc gccctgcact ggaccttgaa gaccctgttc    840

cacttattct ttatgcccag catcctcaca tcgctgttgg tgtttttcgt ttcggagctg    900

gttggcggct tcggcattgc gatcgtggtg ttcatgaacc actacccact ggagaagatc    960

ggggactcag tctgggatgg ccatggattc tcggttggcc agatccatga gaccatgaac   1020

attcggcgag ggattatcac agattggttt ttcggaggct tgaattacca gattgagcac   1080

catttgtggc cgaccctccc tcgccacaac ctgacagcgg ttagctacca ggtggaacag   1140

ctgtgccaga agcacaacct gccgtatcgg aacccgctgc cccatgaagg gttggtcatc   1200

ctgctgcgct atctggcggt gttcgcccgg atggcggaga agcaacccgc ggggaaggct   1260

cta                                                                 1263
```

<210> SEQ ID NO 3
<211> LENGTH: 27
<212> TYPE: DNA
<213> ORGANISM: Artificial Sequence
<220> FEATURE:
<223> OTHER INFORMATION: primer pDonor222Eg5-1

<400> SEQUENCE: 3

```
gccaactttg tacaaaaaag ttggatt                                         27
```

<210> SEQ ID NO 4
<211> LENGTH: 21
<212> TYPE: DNA
<213> ORGANISM: Artificial Sequence
<220> FEATURE:
<223> OTHER INFORMATION: primer D8DEG3-1
<220> FEATURE:
<221> NAME/KEY: misc_feature
<222> LOCATION: (7)..(7)
<223> OTHER INFORMATION: n is a, c, g, or t

<400> SEQUENCE: 4

```
rttrtgncka tctttccacc a                                               21
```

<210> SEQ ID NO 5
<211> LENGTH: 21
<212> TYPE: DNA
<213> ORGANISM: Artificial Sequence
<220> FEATURE:
<223> OTHER INFORMATION: primer D8DEG3-2
<220> FEATURE:
<221> NAME/KEY: misc_feature -continued
<222> LOCATION: (7)..(7)
<223> OTHER INFORMATION: n is a, c, g, or t

<400> SEQUENCE: 5
rttrtgnckg tctttccacc a 21

<210> SEQ ID NO 6
<211> LENGTH: 21
<212> TYPE: DNA
<213> ORGANISM: Artificial Sequence
<220> FEATURE:
<223> OTHER INFORMATION: primer D8DEG3-3
<220> FEATURE:
<221> NAME/KEY: misc_feature
<222> LOCATION: (7)..(7)
<223> OTHER INFORMATION: n is a, c, g, or t

<400> SEQUENCE: 6
rttrtgncka tccttccacc a 21

<210> SEQ ID NO 7
<211> LENGTH: 21
<212> TYPE: DNA
<213> ORGANISM: Artificial Sequence
<220> FEATURE:
<223> OTHER INFORMATION: primer D8DEG3-4
<220> FEATURE:
<221> NAME/KEY: misc_feature
<222> LOCATION: (7)..(7)
<223> OTHER INFORMATION: n is a, c, g, or t

<400> SEQUENCE: 7
rttrtgnckg tccttccacc a 21

<210> SEQ ID NO 8
<211> LENGTH: 19
<212> TYPE: DNA
<213> ORGANISM: Artificial Sequence
<220> FEATURE:
<223> OTHER INFORMATION: primer T7

<400> SEQUENCE: 8
ggaaacagct atgaccatg 19

<210> SEQ ID NO 9
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 9
gtaatacgac tcactatagg gc 22

<210> SEQ ID NO 10
<211> LENGTH: 4116
<212> TYPE: DNA
<213> ORGANISM: Artificial Sequence
<220> FEATURE:
<223> OTHER INFORMATION: plasmid pHD23-1

<400> SEQUENCE: 10
cctgaattcc agcacactgg cggccgttac tagtggatcc gagctcggta ccaagcttga 60
tgcatagctt gagtattcta acgcgtcacc taaatagctt ggcgtaatca tggtcatagc 120
tgtttcctgt gtgaaattgt tatccgctca caattccaca caacatacga gccggaagca 180

-continued

```
taaagtgtaa agcctggggt gcctaatgag tgagctaact cacattaatt gcgttgcgct    240
cactgcccgc tttccagtcg ggaaacctgt cgtgccagct gcattaatga atcggccaac    300
gcgcggggag aggcggtttg cgtattgggc gctcttccgc ttcctcgctc actgactcgc    360
tgcgctcggt cgttcggctg cggcgagcgg tatcagctca ctcaaaggcg gtaatacggt    420
tatccacaga atcaggggat aacgcaggaa agaacatgtg agcaaaaggc cagcaaaagg    480
ccaggaaccg taaaaaggcc gcgttgctgg cgtttttcca taggctccgc ccccctgacg    540
agcatcacaa aaatcgacgc tcaagtcaga ggtggcgaaa cccgacagga ctataaagat    600
accaggcgtt tccccctgga agctccctcg tgcgctctcc tgttccgacc ctgccgctta    660
ccggatacct gtccgccttt ctcccttcgg gaagcgtggc gctttctcat agctcacgct    720
gtaggtatct cagttcggtg taggtcgttc gctccaagct gggctgtgtg cacgaacccc    780
ccgttcagcc cgaccgctgc gccttatccg gtaactatcg tcttgagtcc aacccggtaa    840
gacacgactt atcgccactg gcagcagcca ctggtaacag gattagcaga gcgaggtatg    900
taggcggtgc tacagagttc ttgaagtggt ggcctaacta cggctacact agaagaacag    960
tatttggtat ctgcgctctg ctgaagccag ttaccttcgg aaaaagagtt ggtagctctt   1020
gatccggcaa acaaaccacc gctggtagcg gtggtttttt tgtttgcaag cagcagatta   1080
cgcgcagaaa aaaaggatct caagaagatc ctttgatctt ttctacgggg tctgacgctc   1140
agtggaacga aaactcacgt taagggattt tggtcatgag attatcaaaa aggatcttca   1200
cctagatcct tttaaattaa aaatgaagtt ttagcacgtg tcagtcctgc tcctcggcca   1260
cgaagtgcac gcagttgccg gccgggtcgc gcagggcgaa ctcccgcccc cacggctgct   1320
cgccgatctc ggtcatggcc ggcccggagg cgtcccggaa gttcgtggac acgacctccg   1380
accactcggc gtacagctcg tccaggccgc gcacccacac ccaggccagg gtgttgtccg   1440
gcaccacctg gtcctggacc gcgctgatga acagggtcac gtcgtcccgg accacaccgg   1500
cgaagtcgtc ctccacgaag tcccgggaga acccgagccg gtcggtccag aactcgaccg   1560
ctccggcgac gtcgcgcgcg gtgagcaccg gaacggcact ggtcaacttg gccatggtgg   1620
ccctcctcac gtgctattat tgaagcattt atcagggtta ttgtctcatg agcggataca   1680
tatttgaatg tatttagaaa aataaacaaa taggggttcc gcgcacattt ccccgaaaag   1740
tgccacctga tgcggtgtga aataccgcac agatgcgtaa ggagaaaata ccgcatcagg   1800
aaattgtaag cgttaataat tcagaagaac tcgtcaagaa ggcgatagaa ggcgatgcgc   1860
tgcgaatcgg gagcggcgat accgtaaagc acgaggaagc ggtcagccca ttcgccgcca   1920
agctcttcag caatatcacg ggtagccaac gctatgtcct gatagcggtc cgccacaccc   1980
agccggccac agtcgatgaa tccagaaaag cggccatttt ccaccatgat attcggcaag   2040
caggcatcgc catgggtcac gacgagatcc tcgccgtcgg gcatgctcgc cttgagcctg   2100
gcgaacagtt cggctggcgc gagcccctga tgctcttcgt ccagatcatc ctgatcgaca   2160
agaccggctt ccatccgagt acgtgctcgc tcgatgcgat gtttcgcttg gtggtcgaat   2220
gggcaggtag ccggatcaag cgtatgcagc cgccgcattg catcagccat gatggatact   2280
ttctcggcag gagcaaggtg agatgacagg agatcctgcc ccggcacttc gcccaatagc   2340
agccagtccc ttcccgcttc agtgacaacg tcgagcacag ctgcgcaagg aacgcccgtc   2400
gtggccagcc acgatagccg cgctgcctcg tcttgcagtt cattcagggc accggacagg   2460
tcggtcttga caaaaagaac cgggcgcccc tgcgctgaca gccggaacac ggcggcatca   2520
gagcagccga ttgtctgttg tgcccagtca tagccgaata gcctctccac ccaagcggcc   2580
```

-continued

```
ggagaacctg cgtgcaatcc atcttgttca atcatgcgaa acgatcctca tcctgtctct   2640

tgatcagagc ttgatcccct gcgccatcag atccttggcg gcaagaaagc catccagttt   2700

actttgcagg gcttcccaac cttaccagag ggcgccccag ctggcaattc cggttcgctt   2760

gctgtccata aaaccgccca gtctagctat cgccatgtaa gcccactgca agctacctgc   2820

tttctctttg cgcttgcgtt ttcccttgtc cagatagccc agtagctgac attcatccgg   2880

ggtcagcacc gtttctgcgg actggctttc tacgtgaaaa ggatctaggt gaagatcctt   2940

tttgataatc tcatgcctga catttatatt ccccagaaca tcaggttaat ggcgtttttg   3000

atgtcatttt cgcggtggct gagatcagcc acttcttccc cgataacgga gaccggcaca   3060

ctggccatat cggtggtcat catgcgccag ctttcatccc cgatatgcac caccgggtaa   3120

agttcacggg agactttatc tgacagcaga cgtgcactgg ccagggggat caccatccgt   3180

cgccccggcg tgtcaataat atcactctgt acatccacaa acagacgata acggctctct   3240

cttttatagg tgtaaacctt aaactgccgt acgtataggc tgcgcaactg ttgggaaggg   3300

cgatcggtgc gggcctcttc gctattacgc cagctggcga aagggggatg tgctgcaagg   3360

cgattaagtt gggtaacgcc agggttttcc cagtcacgac gttgtaaaac gacggccagt   3420

gaattgtaat acgactcact atagggcgaa ttgggccctc tagatgcatg ctcgagcggc   3480

cgccagtgtg atggatatct gcagaattca gggccaactt tgtacaaaaa agttggattt   3540

tttttcggcc cacgatctca catggtgaaa aggccagcac ttccgctgac cgttgatggt   3600

gtcacctatg atgtgtctgc ctggttgaac catcatccag gggtgctga catcattgag   3660

aactaccgcg gtcgtgatgc cactgatgtc tttatggtta tgcactctga aaatgctgtg   3720

agtaaactaa gaaggatgcc tatcatggaa ccatcatctc cactgacgcc tacgccaccg   3780

aaacccaact cagacgaacc gcaggaggat ttccgcaagc tccgagatga gctcatcgca   3840

gcaggaatgt tcgacgcatc accgatgtgg tacgcatata agacgctcac tacgctgggc   3900

ctcggggtcc tcgcggtgct attgatgacc cagtggcact ggtacctcgt cggggcaatc   3960

gtgttgggca ttcacttcca acaaatgggt tggttgtcgc acgatatctg ccaccatcag   4020

ctgttcaagg accgatcgat caacaacgcc atcggcttgc ttttcgggaa cgtcttgcaa   4080

gggttctctg tgacctggtg gaaggacagt cacaac                             4116
```

<210> SEQ ID NO 11
<211> LENGTH: 419
<212> TYPE: PRT
<213> ORGANISM: Euglena gracilis
<220> FEATURE:
<221> NAME/KEY: MISC_FEATURE
<222> LOCATION: (1)..(419)
<223> OTHER INFORMATION: NCBI Accession No. AAD45877

<400> SEQUENCE: 11

```
Met Lys Ser Lys Arg Gln Ala Leu Ser Pro Leu Gln Leu Met Glu Gln
1               5                   10                  15

Thr Tyr Asp Val Val Asn Phe His Pro Gly Gly Ala Glu Ile Ile Glu
            20                  25                  30

Asn Tyr Gln Gly Arg Asp Ala Thr Asp Ala Phe Met Val Met His Phe
        35                  40                  45

Gln Glu Ala Phe Asp Lys Leu Lys Arg Met Pro Lys Ile Asn Pro Ser
    50                  55                  60

Phe Glu Leu Pro Pro Gln Ala Ala Val Asn Glu Ala Gln Glu Asp Phe
65                  70                  75                  80
```

-continued

```
Arg Lys Leu Arg Glu Glu Leu Ile Ala Thr Gly Met Phe Asp Ala Ser
                85                  90                  95

Pro Leu Trp Tyr Ser Tyr Lys Ile Ser Thr Thr Leu Gly Leu Gly Val
            100                 105                 110

Leu Gly Tyr Phe Leu Met Val Gln Tyr Gln Met Tyr Phe Ile Gly Ala
        115                 120                 125

Val Leu Leu Gly Met His Tyr Gln Gln Met Gly Trp Leu Ser His Asp
    130                 135                 140

Ile Cys His His Gln Thr Phe Lys Asn Arg Asn Trp Asn Asn Leu Val
145                 150                 155                 160

Gly Leu Val Phe Gly Asn Gly Leu Gln Gly Phe Ser Val Thr Cys Trp
                165                 170                 175

Lys Asp Arg His Asn Ala His His Ser Ala Thr Asn Val Gln Gly His
            180                 185                 190

Asp Pro Asp Ile Asp Asn Leu Pro Pro Leu Ala Trp Ser Glu Asp Asp
        195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
        275                 280                 285

Ser Leu Leu Val Phe Phe Val Ser Glu Leu Val Gly Gly Phe Gly Ile
    290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335

Met Asn Ile Arg Arg Gly Ile Ile Thr Asp Trp Phe Phe Gly Gly Leu
            340                 345                 350

Asn Tyr Gln Ile Glu His His Leu Trp Pro Thr Leu Pro Arg His Asn
        355                 360                 365

Leu Thr Ala Val Ser Tyr Gln Val Glu Gln Leu Cys Gln Lys His Asn
    370                 375                 380

Leu Pro Tyr Arg Asn Pro Leu Pro His Glu Gly Leu Val Ile Leu Leu
385                 390                 395                 400

Arg Tyr Leu Ala Val Phe Ala Arg Met Ala Glu Lys Gln Pro Ala Gly
                405                 410                 415

Lys Ala Leu


<210> SEQ ID NO 12
<211> LENGTH: 20
<212> TYPE: DNA
<213> ORGANISM: Artificial Sequence
<220> FEATURE:
<223> OTHER INFORMATION: primer EaD8seq-1

<400> SEQUENCE: 12

ccaccatcag ctgttcaagg                                                20
```

-continued

<210> SEQ ID NO 13
<211> LENGTH: 4363
<212> TYPE: DNA
<213> ORGANISM: Artificial Sequence
<220> FEATURE:
<223> OTHER INFORMATION: plasmid pLF118-1
<220> FEATURE:
<221> NAME/KEY: misc_feature
<222> LOCATION: (4311)..(4350)
<223> OTHER INFORMATION: n is a, c, g, or t

<400> SEQUENCE: 13
gtacaaagtt ggcattataa gaaagcattg cttatcaatt tgttgcaacg aacaggtcac 60
tatcagtcaa aataaaatca ttatttgcca tccagctgat atcccctata gtgagtcgta 120
ttacatggtc atagctgttt cctggcagct ctggcccgtg tctcaaaatc tctgatgtta 180
cattgcacaa gataaaaata tatcatcatg ttagaaaaac tcatcgagca tcaaatgaaa 240
ctgcaattta ttcatatcag gattatcaat accatatttt tgaaaaagcc gtttctgtaa 300
tgaaggagaa aactcaccga ggcagttcca taggatggca agatcctggt atcggtctgc 360
gattccgact cgtccaacat caatacaacc tattaatttc ccctcgtcaa aaataaggtt 420
atcaagtgag aaatcaccat gagtgacgac tgaatccggt gagaatggca aaagcttatg 480
catttctttc cagacttgtt caacaggcca gccattacgc tcgtcatcaa aatcactcgc 540
atcaaccaaa ccgttattca ttcgtgattg cgcctgagcg agacgaaata cgcgatcgct 600
gttaaaagga caattacaaa caggaatcga atgcaaccgg cgcaggaaca ctgccagcgc 660
atcaacaata ttttcacctg aatcaggata ttcttctaat acctggaatg ctgttttccc 720
ggggatcgca gtggtgagta accatgcatc atcaggagta cggataaaat gcttgatggt 780
cggaagaggc ataaattccg tcagccagtt tagtctgacc atctcatctg taacatcatt 840
ggcaacgcta cctttgccat gtttcagaaa caactctggc gcatcgggct tcccatacaa 900
tcgatagatt gtcgcacctg attgcccgac attatcgcga gcccatttat acccatataa 960
atcagcatcc atgttggaat ttaatcgcgg cctcgagcaa gacgtttccc gttgaatatg 1020
gctcatagat cttttctcca tcactgatag ggagtggtaa aataactcca tcaatgatag 1080
agtgtcaaca acatgaccaa aatcccttaa cgtgagttac gcgtattaat tgcgttgcgc 1140
tcactgcccg ctttccagtc gggaaacctg tcgtgccagc tgcattaatg aatcggccaa 1200
cgcgcgggga gaggcggttt gcgtattggg cgctcttccg cttcctcgct cactgactcg 1260
ctgcgctcgg tcgttcggct gcggcgagcg gtatcagctc actcaaaggc ggtaatacgg 1320
ttatccacag aatcagggga taacgcagga aagaacatgt gagcaaaagg ccagcaaaag 1380
gccaggaacc gtaaaaaggc cgcgttgctg gcgtttttcc ataggctccg cccccctgac 1440
gagcatcaca aaaatcgacg ctcaagtcag aggtggcgaa acccgacagg actataaaga 1500
taccaggcgt ttccccctgg aagctccctc gtgcgctctc ctgttccgac cctgccgctt 1560
accggatacc tgtccgcctt tctcccttcg ggaagcgtgg cgctttctca atgctcacgc 1620
tgtaggtatc tcagttcggt gtaggtcgtt cgctccaagc tgggctgtgt gcacgaaccc 1680
cccgttcagc ccgaccgctg cgccttatcc ggtaactatc gtcttgagtc caacccggta 1740
agacacgact tatcgccact ggcagcagcc actggtaaca ggattagcag agcgaggtat 1800
gtaggcggtg ctacagagtt cttgaagtgg tggcctaact acggttacac tagaagaaca 1860
gtatttggta tctgcgctct gctgaagcca gttaccttcg gaaaaagagt tggtagctct 1920
tgatccggca aacaaaccac cgctggtagc ggtggttttt ttgtttgcaa gcagcagatt 1980

-continued

```
acgcgcagaa aaaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca aataatgatt   2400
ttattttgac tgatagtgac ctgttcgttg caacaaattg atgagcaatg ctttttata    2460
atgccaactt tgtacaaaaa agttggtatt tttttcggc ccacgatctc acatggtgaa    2520
aaggccagca cttccgctga ccgttgatgg tgtcacctat gatgtgtctg cctggttgaa   2580
ccatcatcca gggggtgctg acatcattga gaactaccgc ggtcgtgatg ccactgatgt   2640
ctttatggtt atgcactctg aaaatgctgt gagtaaacta agaaggatgc ctatcatgga   2700
accatcatct ccactgacgc ctacgccacc gaaacccaac tcagacgaac cgcaggagga   2760
tttccgcaag ctccgagatg agctcatcgc agcaggaatg ttcgacgcat caccgatgtg   2820
gtacgcatat aagacgctca ctacgctggg cctcggggtc ctcgcggtgc tattgatgac   2880
ccagtggcac tggtacctcg tcggggcaat cgtgttgggc attcacttcc aacaaatggg   2940
ttggttgtcg cacgatatct gccaccatca gctgttcaag gaccgatcga tcaacaacgc   3000
catcggcttg cttttcggga acgtcttgca agggttctct gtgacctggt ggaaggacag   3060
gcacaatgca caccactccg ccaccaacgt gcaaggccac gaccccgaca ttgacaacct   3120
gccgctgctg gcatggtcca aggaggacgt ggagagggcc ggcccgttct cacggcggat   3180
gatcaagtac cagcaatact acttcttctt catctgtgcc ctcctgaggt tcatctggtg   3240
cttccagagc atccacacag ccaagggcct gaaggatcgc agcaaccagt actaccgcag   3300
gcagtacgag aaagagagcg tgggcctggc cctccactgg ggcctgaagg cgttgttcta   3360
ctacttttat atgccaagct tcttgaccgg actcatggtg tttttcgtgt ccgagttgct   3420
tgggggcttc ggcatcgcca tcgtggtgtt catgaaccac tacccccctgg agaagatcca   3480
ggactcggtg tgggacggcc acggcttttg cgccggccag attcacgaaa cgatgaacgt   3540
ccagcgggga ctcgtcacgg actggttctt cggtgggctg aattaccaaa tcgagcacca   3600
cctgtggccg acgctgcccc ggcacaacct gacggcggcc agcatcaaag tggagcagtt   3660
gtgcaagaag cacaacttgc cgtatcgcag ccccccaatg ctggaggggg tgggcatcct   3720
gatcagctac ctgggcacct ttgcccgcat ggtggcaaag gccgacaagg cgtaagtgac   3780
atggcaccgc tcaggactct gatagttggg ctgacgcttt ggttgtcatc ccttgcccct   3840
tcatatcacc tctggcccga ctcggattct ctctggagct ctaacctgtt caatgtggac   3900
tgctacacat atgagttcct cggatctctg gggaacagcc tttggaagac tcggcattcc   3960
tttatgcttg gaaggcttga gacctcttct gcaggactca aggcaaccct cctcagtgtc   4020
gggaaagagt atttgccttc ggcctgacct gctatacctc acccaacatg cgtcgtggaa   4080
ttaatgatca ttgttaaagt ttggtgcgat ttctgattgt gcgcaaattg tgcggaggcg   4140
cggcacacac gttctcctcc ggccatcaca gtccaaggtc aaatttccaa ctctaatcac   4200
catgatgggc cacagctttg cacactattt ctggcagagc tgcaagaaac tcgccacagt   4260
gagttttgag agatgttcag tgctgcgcat ttgatcggca ttgtggcctt nnnnnnnnnn   4320
nnnnnnnnnn nnnnnnnnnn nnnnnnnnnn acccaacttt ctt                     4363
```

-continued

<210> SEQ ID NO 14
<211> LENGTH: 4307
<212> TYPE: DNA
<213> ORGANISM: Artificial Sequence
<220> FEATURE:
<223> OTHER INFORMATION: plasmid pLF118-2
<220> FEATURE:
<221> NAME/KEY: misc_feature
<222> LOCATION: (4255)..(4294)
<223> OTHER INFORMATION: n is a, c, g, or t

<400> SEQUENCE: 14
gtacaaagtt ggcattataa gaaagcattg cttatcaatt tgttgcaacg aacaggtcac 60
tatcagtcaa aataaaatca ttatttgcca tccagctgat atcccctata gtgagtcgta 120
ttacatggtc atagctgttt cctggcagct ctggcccgtg tctcaaaatc tctgatgtta 180
cattgcacaa gataaaaata tatcatcatg ttagaaaaac tcatcgagca tcaaatgaaa 240
ctgcaattta ttcatatcag gattatcaat accatatttt tgaaaaagcc gtttctgtaa 300
tgaaggagaa aactcaccga ggcagttcca taggatggca agatcctggt atcggtctgc 360
gattccgact cgtccaacat caatacaacc tattaatttc ccctcgtcaa aaataaggtt 420
atcaagtgag aaatcaccat gagtgacgac tgaatccggt gagaatggca aaagcttatg 480
catttctttc cagacttgtt caacaggcca gccattacgc tcgtcatcaa aatcactcgc 540
atcaaccaaa ccgttattca ttcgtgattg cgcctgagcg agacgaaata cgcgatcgct 600
gttaaaagga caattacaaa caggaatcga atgcaaccgg cgcaggaaca ctgccagcgc 660
atcaacaata ttttcacctg aatcaggata ttcttctaat acctggaatg ctgttttccc 720
ggggatcgca gtggtgagta accatgcatc atcaggagta cggataaaat gcttgatggt 780
cggaagaggc ataaattccg tcagccagtt tagtctgacc atctcatctg taacatcatt 840
ggcaacgcta cctttgccat gtttcagaaa caactctggc gcatcgggct tcccatacaa 900
tcgatagatt gtcgcacctg attgcccgac attatcgcga gcccatttat acccatataa 960
atcagcatcc atgttggaat ttaatcgcgg cctcgagcaa gacgtttccc gttgaatatg 1020
gctcatagat cttttctcca tcactgatag ggagtggtaa aataactcca tcaatgatag 1080
agtgtcaaca acatgaccaa aatcccttaa cgtgagttac gcgtattaat tgcgttgcgc 1140
tcactgcccg ctttccagtc gggaaacctg tcgtgccagc tgcattaatg aatcggccaa 1200
cgcgcgggga gaggcggttt gcgtattggg cgctcttccg cttcctcgct cactgactcg 1260
ctgcgctcgg tcgttcggct gcggcgagcg gtatcagctc actcaaaggc ggtaatacgg 1320
ttatccacag aatcagggga taacgcagga aagaacatgt gagcaaaagg ccagcaaaag 1380
gccaggaacc gtaaaaaggc cgcgttgctg gcgtttttcc ataggctccg cccccctgac 1440
gagcatcaca aaaatcgacg ctcaagtcag aggtggcgaa acccgacagg actataaaga 1500
taccaggcgt ttccccctgg aagctccctc gtgcgctctc ctgttccgac cctgccgctt 1560
accggatacc tgtccgcctt tctcccttcg ggaagcgtgg cgctttctca atgctcacgc 1620
tgtaggtatc tcagttcggt gtaggtcgtt cgctccaagc tgggctgtgt gcacgaaccc 1680
cccgttcagc ccgaccgctg cgccttatcc ggtaactatc gtcttgagtc caacccggta 1740
agacacgact tatcgccact ggcagcagcc actggtaaca ggattagcag agcgaggtat 1800
gtaggcggtg ctacagagtt cttgaagtgg tggcctaact acggttacac tagaagaaca 1860
gtatttggta tctgcgctct gctgaagcca gttaccttcg gaaaaagagt tggtagctct 1920

-continued

```
tgatccggca aacaaaccac cgctggtagc ggtggttttt ttgtttgcaa gcagcagatt   1980
acgcgcagaa aaaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca aataatgatt   2400
ttattttgac tgatagtgac ctgttcgttg caacaaattg atgagcaatg cttttttata   2460
atgccaactt tgtacaaaaa agttggattt tttttcggcc cacgatctca catggtgaaa   2520
aggccagcac ttccgctgac cgttgatggt gtcacctatg atgtgtctgc ctggttgaac   2580
catcatccag gggtgctga catcattgag aactaccgcg gtcgtgatgc cactgatgtc   2640
tttatggtta tgcactctga aaatgctgtg agtaaactaa gaaggatgcc tatcatggaa   2700
ccatcatctc cactgacgcc tacgccaccg aaacccaact cagacgaacc gcaggaggat   2760
ttccgcaagc tccgagatga gctcatcgca gcaggaatgt tcgacgcatc accgatgtgg   2820
tacgcatata agacgctcag tacgctgggc ctcggggtcc tcgcggtgct attgatgacc   2880
cagtggcact ggtacctcgt cggggcaatc gtgttgggca ttcacttcca acaaatgggt   2940
tggttgtcgc acgatatctg ccaccatcag ctgttcaagg accgatcgat caacaacgcc   3000
atcggcttgc ttttcgggaa cgtcttgcaa gggttctctg tgacctggtg gaaggacagg   3060
cacaatgcac accactccgc caccaacgtg caaggccacg accccgacat tgacaacctg   3120
ccgctgctgg catggtccaa ggaggacgtg gagagggccg gcccgttctc acggcggatt   3180
atcaagtacc agcaatacta cttcttcttc atctgtgccc tcctgaggtt catctggtgc   3240
ttccagagca tccacacagc cacgggcctg aaggatcgca gcaaccagta ctaccgcagg   3300
cagtacgaga aagagagcgt gggcctggcc ctccactggg gcctgaaggc gttgttctac   3360
tacttttata tgccaagctt cttgaccgga ctcatggtgt ttttcgtgtc cgagttgctt   3420
gggggcttcg gcatcgccat cgtggtgttc atgaaccact acccccctgga gaagatccag   3480
gactcggtgt gggacggcca cggcttttgc gccggccaga ttcacgaaac gatgaacgtc   3540
cagcggggac tcgtcacgga ctggttcttc ggtgggctga attaccaaat cgagcaccac   3600
ctgtggccga cgctgccccg gcacaacctg acggcggcca gcatcaaagt ggagcagttg   3660
tgcaagaagc acaacttgcc gtatcgcagc cccccaatgc tggagggggt gggcatcctg   3720
atcagctacc tgggcacctt tgcccgcatg gtggcaaagg ccgacaaggc gtaagtgaca   3780
tggcaccgct caggactctg atagttgggc tgacgctttg gttgtcatcc cttgcccctt   3840
catatcacct ctggccctac tcggattctc tctggagctc taacctgttc aatgtggact   3900
gctacacata tgagttcctc ggatctctgg ggaacagcct ttggaagact cggcattcct   3960
ttatgcttgg aaggcttgag acctcttctg caggactcaa ggcaaccctc ctcagtgtcg   4020
ggaaagagta tttgccttcg gcctgacctg ctatacctca cccaacatgc gtcgtggaat   4080
taatgatcat tgttaagagt ttggtgcgat ttctgattgt gcgcaaattg tgcggaggcg   4140
cggcacacac gttctcctcc ggccatcaca gtccaaggtc aaatttccaa ctctaatcac   4200
catgatgggc cacagctttg cacactattt ctggcagagc tgcaagaaac tcgcnnnnnn   4260
nnnnnnnnnn nnnnnnnnnn nnnnnnnnnn nnnnacccaa ctttctt                 4307
```

<210> SEQ ID NO 15
<211> LENGTH: 4307
<212> TYPE: DNA
<213> ORGANISM: Artificial Sequence
<220> FEATURE:
<223> OTHER INFORMATION: plasmid pLF118-3
<220> FEATURE:
<221> NAME/KEY: misc_feature
<222> LOCATION: (4255)..(4294)
<223> OTHER INFORMATION: n is a, c, g, or t

<400> SEQUENCE: 15
gtacaaagtt ggcattataa gaaagcattg cttatcaatt tgttgcaacg aacaggtcac 60
tatcagtcaa aataaaatca ttatttgcca tccagctgat atcccctata gtgagtcgta 120
ttacatggtc atagctgttt cctggcagct ctggcccgtg tctcaaaatc tctgatgtta 180
cattgcacaa gataaaaata tatcatcatg ttagaaaaac tcatcgagca tcaaatgaaa 240
ctgcaattta ttcatatcag gattatcaat accatatttt tgaaaaagcc gtttctgtaa 300
tgaaggagaa aactcaccga ggcagttcca taggatggca agatcctggt atcggtctgc 360
gattccgact cgtccaacat caatacaacc tattaatttc ccctcgtcaa aaataaggtt 420
atcaagtgag aaatcaccat gagtgacgac tgaatccggt gagaatggca aaagcttatg 480
catttctttc cagacttgtt caacaggcca gccattacgc tcgtcatcaa aatcactcgc 540
atcaaccaaa ccgttattca ttcgtgattg cgcctgagcg agacgaaata cgcgatcgct 600
gttaaaagga caattacaaa caggaatcga atgcaaccgg cgcaggaaca ctgccagcgc 660
atcaacaata ttttcacctg aatcaggata ttcttctaat acctggaatg ctgttttccc 720
ggggatcgca gtggtgagta accatgcatc atcaggagta cggataaaat gcttgatggt 780
cggaagaggc ataaattccg tcagccagtt tagtctgacc atctcatctg taacatcatt 840
ggcaacgcta cctttgccat gtttcagaaa caactctggc gcatcgggct tcccatacaa 900
tcgatagatt gtcgcacctg attgcccgac attatcgcga gcccatttat acccatataa 960
atcagcatcc atgttggaat ttaatcgcgg cctcgagcaa gacgtttccc gttgaatatg 1020
gctcatagat cttttctcca tcactgatag ggagtggtaa aataactcca tcaatgatag 1080
agtgtcaaca acatgaccaa aatcccttaa cgtgagttac gcgtattaat tgcgttgcgc 1140
tcactgcccg ctttccagtc gggaaacctg tcgtgccagc tgcattaatg aatcggccaa 1200
cgcgcgggga gaggcggttt gcgtattggg cgctcttccg cttcctcgct cactgactcg 1260
ctgcgctcgg tcgttcggct gcggcgagcg gtatcagctc actcaaaggc ggtaatacgg 1320
ttatccacag aatcagggga taacgcagga aagaacatgt gagcaaaagg ccagcaaaag 1380
gccaggaacc gtaaaaaggc cgcgttgctg gcgtttttcc ataggctccg cccccctgac 1440
gagcatcaca aaaatcgacg ctcaagtcag aggtggcgaa acccgacagg actataaaga 1500
taccaggcgt ttccccctgg aagctccctc gtgcgctctc ctgttccgac cctgccgctt 1560
accggatacc tgtccgcctt tctcccttcg ggaagcgtgg cgctttctca atgctcacgc 1620
tgtaggtatc tcagttcggt gtaggtcgtt cgctccaagc tgggctgtgt gcacgaaccc 1680
cccgttcagc ccgaccgctg cgccttatcc ggtaactatc gtcttgagtc caacccggta 1740
agacacgact tatcgccact ggcagcagcc actggtaaca ggattagcag agcgaggtat 1800
gtaggcggtg ctacagagtt cttgaagtgg tggcctaact acggttacac tagaagaaca 1860
gtatttggta tctgcgctct gctgaagcca gttaccttcg gaaaaagagt tggtagctct 1920

-continued

```
tgatccggca aacaaaccac cgctggtagc ggtggttttt ttgtttgcaa gcagcagatt   1980
acgcgcagaa aaaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca aataatgatt   2400
ttattttgac tgatagtgac ctgttcgttg caacaaattg atgagcaatg cttttttata   2460
atgccaactt tgtacaaaaa agttggctat ttttttcgg cccacgatct cacatggtga   2520
aaaggccagc acttccgctg accgttgatg gtgtcaccta tgatgtgtct gcctggttga   2580
accatcatcc agggggtgct gacatcattg agaactaccg cggtcgtgat gccactgatg   2640
tctttatggt tatgcactct gaaaatgctg tgagtaaact aagaaggatg cctatcatgg   2700
aaccatcatc tccactgacg cctacgccac cgaaacccaa ctcagacgaa ccgcaggagg   2760
atttccgcaa gctccgagat gagctcatcg cagcaggaat gttcgacgca tcaccgatgt   2820
ggtacgcata taagacgctc agtacgctgg gcctcggggt cctcgcggtg ctattgatga   2880
cccagtggca ctggtacctc gtcggggcaa tcgtgttggg cattcacttc caacaaatgg   2940
gttggttgtc gcacgatatc tgccaccatc agctgttcaa ggaccgatcg atcaacaacg   3000
ccatcggctt gcttttcggg aacgtcttgc aagggttctc tgtgacctgg tggaaggaca   3060
ggcacaatgc acaccactcc gccaccaacg tgcaaggcca cgaccccgac attgacaacc   3120
tgccgctgct ggcatggtcc aaggaggacg tggagagggc cggcccgttc tcacggcgga   3180
tgatcaagta ccagcaatac tacttcttct tcatctgtgc cctcctgagg ttcatctggt   3240
gcttccagag catccacaca gccacgggcc tgaaggatcg cagcaaccag tactaccgca   3300
ggcagtacga gaaagagagc gtgggcctgg ccctccactg gggcctgaag gcgttgttct   3360
actactttta tatgccaagc ttcttgaccg gactcatggt gtttttcgtg tccgagttgc   3420
ttgggggctt cggcatcgcc atcgtggtgt tcatgaacca ctacccccctg gagaagatcc   3480
aggactcggt gtgggacggc cacggctttt gcgccggcca gattcacgaa acgatgaacg   3540
tccagcgggg actcgtcacg gactggttct tcggtgggct gaattaccaa atcgagcacc   3600
acctgtggcc gacgctgccc cggcacaacc tgacggcggc cagcatcaaa gtggagcagt   3660
tgtgcaagaa gcacaacttg ccgtatcgca gcccccccaat gctggagggg gtgggcatcc   3720
tgatcagcta cctgggcacc tttgcccgca tggtggcaaa ggccgacaag gcgtaagtga   3780
catggcaccg ctcaggactc tgatagttgg gctgacgctt tggttgtcat cccttgcccc   3840
ttcatatcac ctctggccct actcggattc tctctagctc taacctgttc aatgtggact   3900
gctacacata tgagttcctc ggatctctgg ggaacagcct ttggaagact cggcattcct   3960
ttatgcttgg aaggcttgag acctcttctg caggactcaa ggcaaccctc ctcagtgtcg   4020
ggaaagagta tttgccttcg gcctgacctg ctatacctca cccaacatgc gtcgtggaat   4080
taatgatcat tgttaagagt ttggtgcgat ttctgattgt gcgcaaattg tgcggaggcg   4140
cggcacacac gttctcctcc ggccatcaca gtccaaggtc aaatttccaa ctctaatcac   4200
catgatgggc cacagctttg cacactattt ctggcagagc tgcaagaaac tcgcnnnnnn   4260
nnnnnnnnnn nnnnnnnnnn nnnnnnnnnn nnnnacccaa ctttctt                 4307
```

-continued

<210> SEQ ID NO 16
<211> LENGTH: 4297
<212> TYPE: DNA
<213> ORGANISM: Artificial Sequence
<220> FEATURE:
<223> OTHER INFORMATION: plasmid pLF118-4
<220> FEATURE:
<221> NAME/KEY: misc_feature
<222> LOCATION: (4245)..(4284)
<223> OTHER INFORMATION: n is a, c, g, or t

<400> SEQUENCE: 16
gtacaaagtt ggcattataa gaaagcattg cttatcaatt tgttgcaacg aacaggtcac 60
tatcagtcaa aataaaatca ttatttgcca tccagctgat atcccctata gtgagtcgta 120
ttacatggtc atagctgttt cctggcagct ctggcccgtg tctcaaaatc tctgatgtta 180
cattgcacaa gataaaaata tatcatcatg ttagaaaaac tcatcgagca tcaaatgaaa 240
ctgcaattta ttcatatcag gattatcaat accatatttt tgaaaaagcc gtttctgtaa 300
tgaaggagaa aactcaccga ggcagttcca taggatggca agatcctggt atcggtctgc 360
gattccgact cgtccaacat caatacaacc tattaatttc ccctcgtcaa aaataaggtt 420
atcaagtgag aaatcaccat gagtgacgac tgaatccggt gagaatggca aaagcttatg 480
catttctttc cagacttgtt caacaggcca gccattacgc tcgtcatcaa aatcactcgc 540
atcaaccaaa ccgttattca ttcgtgattg cgcctgagcg agacgaaata cgcgatcgct 600
gttaaaagga caattacaaa caggaatcga atgcaaccgg cgcaggaaca ctgccagcgc 660
atcaacaata ttttcacctg aatcaggata ttcttctaat acctggaatg ctgttttccc 720
ggggatcgca gtggtgagta accatgcatc atcaggagta cggataaaat gcttgatggt 780
cggaagaggc ataaattccg tcagccagtt tagtctgacc atctcatctg taacatcatt 840
ggcaacgcta cctttgccat gtttcagaaa caactctggc gcatcgggct tcccatacaa 900
tcgatagatt gtcgcacctg attgcccgac attatcgcga gcccatttat acccatataa 960
atcagcatcc atgttggaat ttaatcgcgg cctcgagcaa gacgtttccc gttgaatatg 1020
gctcatagat cttttctcca tcactgatag ggagtggtaa aataactcca tcaatgatag 1080
agtgtcaaca acatgaccaa aatcccttaa cgtgagttac gcgtattaat tgcgttgcgc 1140
tcactgcccg ctttccagtc gggaaacctg tcgtgccagc tgcattaatg aatcggccaa 1200
cgcgcgggga gaggcggttt gcgtattggg cgctcttccg cttcctcgct cactgactcg 1260
ctgcgctcgg tcgttcggct gcggcgagcg gtatcagctc actcaaaggc ggtaatacgg 1320
ttatccacag aatcagggga taacgcagga aagaacatgt gagcaaaagg ccagcaaaag 1380
gccaggaacc gtaaaaaggc cgcgttgctg gcgtttttcc ataggctccg cccccctgac 1440
gagcatcaca aaaatcgacg ctcaagtcag aggtggcgaa acccgacagg actataaaga 1500
taccaggcgt ttccccctgg aagctccctc gtgcgctctc ctgttccgac cctgccgctt 1560
accggatacc tgtccgcctt tctcccttcg ggaagcgtgg cgctttctca atgctcacgc 1620
tgtaggtatc tcagttcggt gtaggtcgtt cgctccaagc tgggctgtgt gcacgaaccc 1680
cccgttcagc ccgaccgctg cgccttatcc ggtaactatc gtcttgagtc caacccggta 1740
agacacgact tatcgccact ggcagcagcc actggtaaca ggattagcag agcgaggtat 1800
gtaggcggtg ctacagagtt cttgaagtgg tggcctaact acggttacac tagaagaaca 1860
gtatttggta tctgcgctct gctgaagcca gttaccttcg gaaaaagagt tggtagctct 1920

-continued

```
tgatccggca aacaaaccac cgctggtagc ggtggttttt ttgtttgcaa gcagcagatt   1980
acgcgcagaa aaaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca aataatgatt   2400
ttattttgac tgatagtgac ctgttcgttg caacaaattg atgagcaatg ctttttata    2460
atgccaactt tgtacaaaaa agttggtttc aggcccacga tctcacatgg tgaaaaggcc   2520
agcacttccg ctgaccgttg atggtgtcac ctatgatgtg tctgcctggt tgaaccatca   2580
tccagggggt gctgacatca ttgagaacta ccgcggtcgt gatgccactg atgtctttat   2640
ggttatgcac tctgaaaatg ctgtgagtaa actaagaagg atgcctatca tggaaccatc   2700
atctccactg acgcctacgc caccgaaacc caactcagac gaaccgcagg aggatttccg   2760
caagctccga gatgagctca tcgcagcagg aatgttcgac gcatcaccga tgtggtacgc   2820
atataagacg ctcagtacgc tgggcctcgg ggtcctcgcg gtgctattga tgacccagtg   2880
gcactggtac ctcgtcgggg caatcgtgtt gggcattcac ttccaacaaa tgggttggtt   2940
gtcgcacgat atctgccacc atcagctgtt caaggaccga tcgatcaaca acgccatcgg   3000
cttgcttttc gggaacgtct tgcaagggtt ctctgtgacc tggtggaagg acaggcacaa   3060
tgcacaccac tccgccacca acgtgcaagg ccacgacccc gacattgaca acctgccgct   3120
gctggcatgg tccaaggagg acgtggagag ggccggcccg ttctcacggc ggatgatcaa   3180
gtaccagcaa tactacttct tcttcatctg tgccctcctg aggttcatct ggtgcttcca   3240
gagcatccac acagccaagg gcctgaagga tcgcagcaac cagtactacc gcaggcagta   3300
cgagaaagag agcgtgggcc tggccctcca ctggggcctg aaggcgttgt tctactactt   3360
ttatatgcca agcttcttga ccggactcat ggtgtttttc gtgtccgagt tgcttggggg   3420
cttcggcatc gccatcgtgg tgttcatgaa ccactacccc ctggagaaga tccaggactc   3480
ggtgtgggac ggccacggct tttgcgccgg ccagattcac gaaacgatga acgtccagcg   3540
gggactcgtc acggactggt tcttcggtgg gctgaattac caaatcgagc accacctgtg   3600
gccgacgctg ccccggcaca acctgacggc ggccagcatc aaagtggagc agttgtgcaa   3660
gaagcacaac ttgccgtatc gcagcccccc aatgctggag gggggtgggca tcctgatcag  3720
ctacctgggc acctttgccc gcatggtggc aaaggccgac aaggcgtaag tgacatggca   3780
ccgctcagga ctctgatagt tgggctgacg ctttggttgt catcccttgc cccttcatat   3840
cacctctggc ccgactcgga ttctctctgg agctctaacc tgttcaatgt ggactgctac   3900
acatatgagt tcctcggatc tcgggggaac agcctttgga agactcggca ttcctttatg   3960
cttggaaggc ttgagacctc ttctgcagga ctcaaggcaa ccctcctcag tgtcgggaaa   4020
gagtatttgc cttcggcctg acctgctata cctcacccaa catgcgtcgt ggaattaatg   4080
atcatcgtta agagtttggt gcgatttctg attgtgcgca aattgtgcgg aggcgcggca   4140
cacacgttct cctccagcca tcacagtcca aggtcaaatt tccaactcta atcaccatga   4200
tgggccacag ctttgcacac tatttctggc agagctgcaa gaaannnnnn nnnnnnnnnn   4260
nnnnnnnnnn nnnnnnnnnn nnnnacccaa ctttctt                            4297
```

-continued

<210> SEQ ID NO 17
<211> LENGTH: 1260
<212> TYPE: DNA
<213> ORGANISM: Euglena anabaena

<400> SEQUENCE: 17
atggtgaaaa ggccagcact tccgctgacc gttgatggtg tcacctatga tgtgtctgcc 60
tggttgaacc atcatccagg gggtgctgac atcattgaga actaccgcgg tcgtgatgcc 120
actgatgtct ttatggttat gcactctgaa aatgctgtga gtaaactaag aaggatgcct 180
atcatggaac catcatctcc actgacgcct acgccaccga aacccaactc agacgaaccg 240
caggaggatt tccgcaagct ccgagatgag ctcatcgcag caggaatgtt cgacgcatca 300
ccgatgtggt acgcatataa gacgctcact acgctgggcc tcggggtcct cgcggtgcta 360
ttgatgaccc agtggcactg gtacctcgtc ggggcaatcg tgttgggcat tcacttccaa 420
caaatgggtt ggttgtcgca cgatatctgc caccatcagc tgttcaagga ccgatcgatc 480
aacaacgcca tcggcttgct ttcgggaac gtcttgcaag ggttctctgt gacctggtgg 540
aaggacaggc acaatgcaca ccactccgcc accaacgtgc aaggccacga ccccgacatt 600
gacaacctgc cgctgctggc atggtccaag gaggacgtgg agagggccgg cccgttctca 660
cggcggatga tcaagtacca gcaatactac ttcttcttca tctgtgccct cctgaggttc 720
atctggtgct tccagagcat ccacacagcc aagggcctga aggatcgcag caaccagtac 780
taccgcaggc agtacgagaa agagagcgtg ggcctggccc tccactgggg cctgaaggcg 840
ttgttctact acttttatat gccaagcttc ttgaccggac tcatggtgtt tttcgtgtcc 900
gagttgcttg gggcttcgg catcgccatc gtggtgttca tgaaccacta cccccctggag 960 aagatccagg actcggtgtg ggacggccac ggcttttgcg ccggccagat tcacgaaacg 1020
atgaacgtcc agcggggact cgtcacggac tggttcttcg gtgggctgaa ttaccaaatc 1080
gagcaccacc tgtggccgac gctgccccgg cacaacctga cggcggccag catcaaagtg 1140
gagcagttgt gcaagaagca caacttgccg tatcgcagcc ccccaatgct ggaggggtg 1200 ggcatcctga tcagctacct gggcaccttt gcccgcatgg tggcaaaggc cgacaaggcg 1260

<210> SEQ ID NO 18
<211> LENGTH: 1260
<212> TYPE: DNA
<213> ORGANISM: Euglena anabaena

<400> SEQUENCE: 18
atggtgaaaa ggccagcact tccgctgacc gttgatggtg tcacctatga tgtgtctgcc 60
tggttgaacc atcatccagg gggtgctgac atcattgaga actaccgcgg tcgtgatgcc 120
actgatgtct ttatggttat gcactctgaa aatgctgtga gtaaactaag aaggatgcct 180
atcatggaac catcatctcc actgacgcct acgccaccga aacccaactc agacgaaccg 240
caggaggatt tccgcaagct ccgagatgag ctcatcgcag caggaatgtt cgacgcatca 300
ccgatgtggt acgcatataa gacgctcagt acgctgggcc tcggggtcct cgcggtgcta 360
ttgatgaccc agtggcactg gtacctcgtc ggggcaatcg tgttgggcat tcacttccaa 420
caaatgggtt ggttgtcgca cgatatctgc caccatcagc tgttcaagga ccgatcgatc 480
aacaacgcca tcggcttgct ttcgggaac gtcttgcaag ggttctctgt gacctggtgg 540
aaggacaggc acaatgcaca ccactccgcc accaacgtgc aaggccacga ccccgacatt 600

-continued

```
gacaacctgc cgctgctggc atggtccaag gaggacgtgg agagggccgg cccgttctca    660

cggcggatta tcaagtacca gcaatactac ttcttcttca tctgtgccct cctgaggttc    720

atctggtgct tccagagcat ccacacagcc acgggcctga aggatcgcag caaccagtac    780

taccgcaggc agtacgagaa agagagcgtg ggcctggccc tccactgggg cctgaaggcg    840

ttgttctact acttttatat gccaagcttc ttgaccggac tcatggtgtt tttcgtgtcc    900

gagttgcttg gggcttcgg catcgccatc gtggtgttca tgaaccacta ccccctggag    960

aagatccagg actcggtgtg ggacggccac ggcttttgcg ccggccagat tcacgaaacg   1020

atgaacgtcc agcggggact cgtcacggac tggttcttcg gtgggctgaa ttaccaaatc   1080

gagcaccacc tgtggccgac gctgccccgg cacaacctga cggcggccag catcaaagtg   1140

gagcagttgt gcaagaagca caacttgccg tatcgcagcc ccccaatgct ggagggggtg   1200

ggcatcctga tcagctacct gggcaccttt gcccgcatgg tggcaaaggc cgacaaggcg   1260
```

<210> SEQ ID NO 19
<211> LENGTH: 1260
<212> TYPE: DNA
<213> ORGANISM: Euglena anabaena

<400> SEQUENCE: 19

```
atggtgaaaa ggccagcact tccgctgacc gttgatggtg tcacctatga tgtgtctgcc     60

tggttgaacc atcatccagg gggtgctgac atcattgaga actaccgcgg tcgtgatgcc    120

actgatgtct ttatggttat gcactctgaa aatgctgtga gtaaactaag aaggatgcct    180

atcatggaac catcatctcc actgacgcct acgccaccga aacccaactc agacgaaccg    240

caggaggatt tccgcaagct ccgagatgag ctcatcgcag caggaatgtt cgacgcatca    300

ccgatgtggt acgcatataa gacgctcagt acgctgggcc tcggggtcct cgcggtgcta    360

ttgatgaccc agtggcactg gtacctcgtc ggggcaatcg tgttgggcat tcacttccaa    420

caaatgggtt ggttgtcgca cgatatctgc caccatcagc tgttcaagga ccgatcgatc    480

aacaacgcca tcggcttgct tttcgggaac gtcttgcaag ggttctctgt gacctggtgg    540

aaggacaggc acaatgcaca ccactccgcc accaacgtgc aaggccacga ccccgacatt    600

gacaacctgc cgctgctggc atggtccaag gaggacgtgg agagggccgg cccgttctca    660

cggcggatga tcaagtacca gcaatactac ttcttcttca tctgtgccct cctgaggttc    720

atctggtgct tccagagcat ccacacagcc acgggcctga aggatcgcag caaccagtac    780

taccgcaggc agtacgagaa agagagcgtg ggcctggccc tccactgggg cctgaaggcg    840

ttgttctact acttttatat gccaagcttc ttgaccggac tcatggtgtt tttcgtgtcc    900

gagttgcttg gggcttcgg catcgccatc gtggtgttca tgaaccacta ccccctggag    960

aagatccagg actcggtgtg ggacggccac ggcttttgcg ccggccagat tcacgaaacg   1020

atgaacgtcc agcggggact cgtcacggac tggttcttcg gtgggctgaa ttaccaaatc   1080

gagcaccacc tgtggccgac gctgccccgg cacaacctga cggcggccag catcaaagtg   1140

gagcagttgt gcaagaagca caacttgccg tatcgcagcc ccccaatgct ggagggggtg   1200

ggcatcctga tcagctacct gggcaccttt gcccgcatgg tggcaaaggc cgacaaggcg   1260
```

<210> SEQ ID NO 20
<211> LENGTH: 1260
<212> TYPE: DNA
<213> ORGANISM: Euglena anabaena

<400> SEQUENCE: 20

-continued

```
atggtgaaaa ggccagcact tccgctgacc gttgatggtg tcacctatga tgtgtctgcc     60
tggttgaacc atcatccagg gggtgctgac atcattgaga actaccgcgg tcgtgatgcc    120
actgatgtct ttatggttat gcactctgaa aatgctgtga gtaaactaag aaggatgcct    180
atcatggaac catcatctcc actgacgcct acgccaccga aacccaactc agacgaaccg    240
caggaggatt tccgcaagct ccgagatgag ctcatcgcag caggaatgtt cgacgcatca    300
ccgatgtggt acgcatataa gacgctcagt acgctgggcc tcggggtcct cgcggtgcta    360
ttgatgaccc agtggcactg gtacctcgtc ggggcaatcg tgttgggcat tcacttccaa    420
caaatgggtt ggttgtcgca cgatatctgc caccatcagc tgttcaagga ccgatcgatc    480
aacaacgcca tcggcttgct tttcgggaac gtcttgcaag ggttctctgt gacctggtgg    540
aaggacaggc acaatgcaca ccactccgcc accaacgtgc aaggccacga ccccgacatt    600
gacaacctgc cgctgctggc atggtccaag gaggacgtgg agagggccgg cccgttctca    660
cggcggatga tcaagtacca gcaatactac ttcttcttca tctgtgccct cctgaggttc    720
atctggtgct tccagagcat ccacacagcc aagggcctga aggatcgcag caaccagtac    780
taccgcaggc agtacgagaa agagagcgtg ggcctggccc tccactgggg cctgaaggcg    840
ttgttctact acttttatat gccaagcttc ttgaccggac tcatggtgtt tttcgtgtcc    900
gagttgcttg gggcttcgg catcgccatc gtggtgttca tgaaccacta cccccctggag    960
aagatccagg actcggtgtg ggacggccac ggcttttgcg ccggccagat tcacgaaacg   1020
atgaacgtcc agcggggact cgtcacggac tggttcttcg gtgggctgaa ttaccaaatc   1080
gagcaccacc tgtggccgac gctgccccgg cacaacctga cggcggccag catcaaagtg   1140
gagcagttgt gcaagaagca caacttgccg tatcgcagcc ccccaatgct ggagggggtg   1200
ggcatcctga tcagctacct gggcaccttt gcccgcatgg tggcaaaggc cgacaaggcg   1260
```

<210> SEQ ID NO 21
<211> LENGTH: 420
<212> TYPE: PRT
<213> ORGANISM: Euglena anabaena

<400> SEQUENCE: 21

```
Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Thr Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
```

-continued

```
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Phe Ile Cys Ala Leu Leu Arg Phe
225                 230                 235                 240

Ile Trp Cys Phe Gln Ser Ile His Thr Ala Lys Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420


<210> SEQ ID NO 22
<211> LENGTH: 420
<212> TYPE: PRT
<213> ORGANISM: Euglena anabaena

<400> SEQUENCE: 22

Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95
```

-continued

```
Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Ile Ile
    210                 215                 220

Lys Tyr Gln Gln Tyr Tyr Phe Phe Phe Ile Cys Ala Leu Leu Arg Phe
225                 230                 235                 240

Ile Trp Cys Phe Gln Ser Ile His Thr Ala Thr Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420


<210> SEQ ID NO 23
<211> LENGTH: 420
<212> TYPE: PRT
<213> ORGANISM: Euglena anabaena

<400> SEQUENCE: 23

Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45
```

-continued

```
Ser Glu Asn Ala Val Ser Lys Leu Arg Arg Met Pro Ile Met Glu Pro
    50                  55                  60

Ser Ser Pro Leu Thr Pro Thr Pro Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Phe Ile Cys Ala Leu Leu Arg Phe
225                 230                 235                 240

Ile Trp Cys Phe Gln Ser Ile His Thr Ala Thr Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420
```

<210> SEQ ID NO 24
<211> LENGTH: 420
<212> TYPE: PRT
<213> ORGANISM: Euglena anabaena -continued

<400> SEQUENCE: 24

```
Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Phe Ile Cys Ala Leu Leu Arg Phe
225                 230                 235                 240

Ile Trp Cys Phe Gln Ser Ile His Thr Ala Lys Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415
```

```
Ala Asp Lys Ala
            420


<210> SEQ ID NO 25
<211> LENGTH: 421
<212> TYPE: PRT
<213> ORGANISM: Euglena gracilis
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(421)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: U.S. 7,256,033
<311> PATENT FILING DATE: 2005-06-24
<312> PUBLICATION DATE: 2007-08-14
<313> RELEVANT RESIDUES IN SEQ ID NO: (1)..(421)

<400> SEQUENCE: 25

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285
```

-continued

```
Leu Thr Ser Leu Leu Val Phe Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420
```

<210> SEQ ID NO 26
<211> LENGTH: 34
<212> TYPE: DNA
<213> ORGANISM: Artificial Sequence
<220> FEATURE:
<223> OTHER INFORMATION: oligonucleotide EaD8-5

<400> SEQUENCE: 26
gcggccgcac catggtgaaa aggccagcac ttcc 34

<210> SEQ ID NO 27
<211> LENGTH: 30
<212> TYPE: DNA
<213> ORGANISM: Artificial Sequence
<220> FEATURE:
<223> OTHER INFORMATION: oligonucleotide EaD8-3

<400> SEQUENCE: 27
gcggccgctt acgccttgtc ggcctttgcc 30

<210> SEQ ID NO 28
<211> LENGTH: 4794
<212> TYPE: DNA
<213> ORGANISM: Artificial Sequence
<220> FEATURE:
<223> OTHER INFORMATION: plasmid pLF120-1

<400> SEQUENCE: 28
cctgaattcc agcacactgg cggccgttac tagtggatcc gagctcggta ccaagcttga 60
tgcatagctt gagtattcta acgcgtcacc taaatagctt ggcgtaatca tggtcatagc 120
tgtttcctgt gtgaaattgt tatccgctca caattccaca caacatacga gccggaagca 180
taaagtgtaa agcctggggt gcctaatgag tgagctaact cacattaatt gcgttgcgct 240
cactgcccgc tttccagtcg ggaaacctgt cgtgccagct gcattaatga atcggccaac 300
gcgcggggag aggcggtttg cgtattgggc gctcttccgc ttcctcgctc actgactcgc 360
tgcgctcggt cgttcggctg cggcgagcgg tatcagctca ctcaaaggcg gtaatacggt 420
tatccacaga atcaggggat aacgcaggaa agaacatgtg agcaaaaggc cagcaaaagg 480
ccaggaaccg taaaaaggcc gcgttgctgg cgtttttcca taggctccgc ccccctgacg 540

-continued

```
agcatcacaa aaatcgacgc tcaagtcaga ggtggcgaaa cccgacagga ctataaagat    600
accaggcgtt tccccctgga agctccctcg tgcgctctcc tgttccgacc ctgccgctta    660
ccggatacct gtccgccttt ctcccttcgg gaagcgtggc gctttctcat agctcacgct    720
gtaggtatct cagttcggtg taggtcgttc gctccaagct gggctgtgtg cacgaacccc    780
ccgttcagcc cgaccgctgc gccttatccg gtaactatcg tcttgagtcc aacccggtaa    840
gacacgactt atcgccactg gcagcagcca ctggtaacag gattagcaga gcgaggtatg    900
taggcggtgc tacagagttc ttgaagtggt ggcctaacta cggctacact agaagaacag    960
tatttggtat ctgcgctctg ctgaagccag ttaccttcgg aaaaagagtt ggtagctctt   1020
gatccggcaa acaaaccacc gctggtagcg gtggtttttt tgtttgcaag cagcagatta   1080
cgcgcagaaa aaaaggatct caagaagatc ctttgatctt ttctacgggg tctgacgctc   1140
agtggaacga aaactcacgt taagggattt tggtcatgag attatcaaaa aggatcttca   1200
cctagatcct tttaaattaa aaatgaagtt ttagcacgtg tcagtcctgc tcctcggcca   1260
cgaagtgcac gcagttgccg gccgggtcgc gcagggcgaa ctcccgcccc cacggctgct   1320
cgccgatctc ggtcatggcc ggcccggagg cgtcccggaa gttcgtggac acgacctccg   1380
accactcggc gtacagctcg tccaggccgc gcacccacac ccaggccagg gtgttgtccg   1440
gcaccacctg gtcctggacc gcgctgatga acagggtcac gtcgtcccgg accacaccgg   1500
cgaagtcgtc ctccacgaag tcccgggaga acccgagccg gtcggtccag aactcgaccg   1560
ctccggcgac gtcgcgcgcg gtgagcaccg gaacggcact ggtcaacttg gccatggtgg   1620
ccctcctcac gtgctattat tgaagcattt atcagggtta ttgtctcatg agcggataca   1680
tatttgaatg tatttagaaa aataaacaaa taggggttcc gcgcacattt ccccgaaaag   1740
tgccacctga tgcggtgtga aataccgcac agatgcgtaa ggagaaaata ccgcatcagg   1800
aaattgtaag cgttaatatt tcagaagaac tcgtcaagaa ggcgatagaa ggcgatgcgc   1860
tgcgaatcgg gagcggcgat accgtaaagc acgaggaagc ggtcagccca ttcgccgcca   1920
agctcttcag caatatcacg ggtagccaac gctatgtcct gatagcggtc cgccacaccc   1980
agccggccac agtcgatgaa tccagaaaag cggccatttt ccaccatgat attcggcaag   2040
caggcatcgc catgggtcac gacgagatcc tcgccgtcgg gcatgctcgc cttgagcctg   2100
gcgaacagtt cggctggcgc gagcccctga tgctcttcgt ccagatcatc ctgatcgaca   2160
agaccggctt ccatccgagt acgtgctcgc tcgatgcgat gtttcgcttg gtggtcgaat   2220
gggcaggtag ccggatcaag cgtatgcagc cgccgcattg catcagccat gatggatact   2280
ttctcggcag gagcaaggtg agatgacagg agatcctgcc ccggcacttc gcccaatagc   2340
agccagtccc ttcccgcttc agtgacaacg tcgagcacag ctgcgcaagg aacgcccgtc   2400
gtggccagcc acgatagccg cgctgcctcg tcttgcagtt cattcagggc accggacagg   2460
tcggtcttga caaaaagaac cgggcgcccc tgcgctgaca gccggaacac ggcggcatca   2520
gagcagccga ttgtctgttg tgcccagtca tagccgaata gcctctccac ccaagcggcc   2580
ggagaacctg cgtgcaatcc atcttgttca atcatgcgaa acgatcctca tcctgtctct   2640
tgatcagagc ttgatcccct gcgccatcag atccttggcg gcaagaaagc catccagttt   2700
actttgcagg gcttcccaac cttaccagag ggcgccccag ctggcaattc cggttcgctt   2760
gctgtccata aaaccgccca gtctagctat cgccatgtaa gcccactgca agctacctgc   2820
tttctctttg cgcttgcgtt ttcccttgtc cagatagccc agtagctgac attcatccgg   2880
```

-continued

```
ggtcagcacc gtttctgcgg actggctttc tacgtgaaaa ggatctaggt gaagatcctt   2940

tttgataatc tcatgcctga catttatatt ccccagaaca tcaggttaat ggcgtttttg   3000

atgtcatttt cgcggtggct gagatcagcc acttcttccc cgataacgga gaccggcaca   3060

ctggccatat cggtggtcat catgcgccag ctttcatccc cgatatgcac caccgggtaa   3120

agttcacggg agactttatc tgacagcaga cgtgcactgg ccagggggat caccatccgt   3180

cgccccggcg tgtcaataat atcactctgt acatccacaa acagacgata acggctctct   3240

cttttatagg tgtaaacctt aaactgccgt acgtataggc tgcgcaactg ttgggaaggg   3300

cgatcggtgc gggcctcttc gctattacgc cagctggcga aagggggatg tgctgcaagg   3360

cgattaagtt gggtaacgcc agggttttcc cagtcacgac gttgtaaaac gacggccagt   3420

gaattgtaat acgactcact atagggcgaa ttgggccctc tagatgcatg ctcgagcggc   3480

cgccagtgtg atggatatct gcagaattca gggcggccgc accatggtga aaaggccagc   3540

acttccgctg accgttgatg gtgtcaccta tgatgtgtct gcctggttga accatcatcc   3600

agggggtgct gacatcattg agaactaccg cggtcgtgat gccactgatg tctttatggt   3660

tatgcactct gaaaatgctg tgagtaaact aagaaggatg cctatcatgg aaccatcatc   3720

tccactgacg cctacgccac cgaaacccaa ctcagacgaa ccgcaggagg atttccgcaa   3780

gctccgagat gagctcatcg cagcaggaat gttcgacgca tcaccgatgt ggtacgcata   3840

taagacgctc actacgctgg gcctcggggt cctcgcggtg ctattgatga cccagtggca   3900

ctggtacctc gtcggggcaa tcgtgttggg cattcacttc caacaaatgg gttggttgtc   3960

gcacgatatc tgccaccatc agctgttcaa ggaccgatcg atcaacaacg ccatcggctt   4020

gcttttcggg aacgtcttgc aagggttctc tgtgacctgg tggaaggaca ggcacaatgc   4080

acaccactcc gccaccaacg tgcaaggcca cgaccccgac attgacaacc tgccgctgct   4140

ggcatggtcc aaggaggacg tggagagggc cggcccgttc tcacggcgga tgatcaagta   4200

ccagcaatac tacttcttct tcatctgtgc cctcctgagg ttcatctggt gcttccagag   4260

catccacaca gccaagggcc tgaaggatcg cagcaaccag tactaccgca ggcagtacga   4320

gaaagagagc gtgggcctgg ccctccactg gggcctgaag gcgttgttct actactttta   4380

tatgccaagc ttcttgaccg gactcatggt gtttttcgtg tccgagttgc ttgggggctt   4440

cggcatcgcc atcgtggtgt tcatgaacca ctaccccctg gagaagatcc aggactcggt   4500

gtgggacggc cacggctttt gcgccggcca gattcacgaa acgatgaacg tccagcgggg   4560

actcgtcacg gactggttct tcggtgggct gaattaccaa atcgagcacc acctgtggcc   4620

gacgctgccc cggcacaacc tgacggcggc cagcatcaaa gtggagcagt tgtgcaagaa   4680

gcacaacttg ccgtatcgca gccccccaat gctggagggg gtgggcatcc tgatcagcta   4740

cctgggcacc tttgcccgca tggtggcaaa ggccgacaag gcgtaagcgg ccgc         4794
```

<210> SEQ ID NO 29
<211> LENGTH: 4794
<212> TYPE: DNA
<213> ORGANISM: Artificial Sequence
<220> FEATURE:
<223> OTHER INFORMATION: plasmid pLF120-2

<400> SEQUENCE: 29

```
ttgtaatacg actcactata gggcgaattg ggccctctag atgcatgctc gagcggccgc     60

cagtgtgatg gatatctgca gaattcaggc ctgaattcca gcacactggc ggccgttact    120

agtggatccg agctcggtac caagcttgat gcatagcttg agtattctaa cgcgtcacct    180
```

-continued

```
aaatagcttg gcgtaatcat ggtcatagct gtttcctgtg tgaaattgtt atccgctcac    240
aattccacac aacatacgag ccggaagcat aaagtgtaaa gcctggggtg cctaatgagt    300
gagctaactc acattaattg cgttgcgctc actgcccgct ttccagtcgg gaaacctgtc    360
gtgccagctg cattaatgaa tcggccaacg cgcggggaga ggcggtttgc gtattgggcg    420
ctcttccgct tcctcgctca ctgactcgct gcgctcggtc gttcggctgc ggcgagcggt    480
atcagctcac tcaaaggcgg taatacggtt atccacagaa tcaggggata acgcaggaaa    540
gaacatgtga gcaaaaggcc agcaaaaggc caggaaccgt aaaaaggccg cgttgctggc    600
gtttttccat aggctccgcc cccctgacga gcatcacaaa aatcgacgct caagtcagag    660
gtggcgaaac ccgacaggac tataaagata ccaggcgttt ccccctggaa gctccctcgt    720
gcgctctcct gttccgaccc tgccgcttac cggatacctg tccgcctttc tcccttcggg    780
aagcgtggcg ctttctcata gctcacgctg taggtatctc agttcggtgt aggtcgttcg    840
ctccaagctg ggctgtgtgc acgaaccccc cgttcagccc gaccgctgcg ccttatccgg    900
taactatcgt cttgagtcca acccggtaag acacgactta tcgccactgg cagcagccac    960
tggtaacagg attagcagag cgaggtatgt aggcggtgct acagagttct tgaagtggtg   1020
gcctaactac ggctacacta gaagaacagt atttggtatc tgcgctctgc tgaagccagt   1080
taccttcgga aaaagagttg gtagctcttg atccggcaaa caaaccaccg ctggtagcgg   1140
tggttttttt gtttgcaagc agcagattac gcgcagaaaa aaaggatctc aagaagatcc   1200
tttgatcttt tctacggggt ctgacgctca gtggaacgaa aactcacgtt aagggatttt   1260
ggtcatgaga ttatcaaaaa ggatcttcac ctagatcctt ttaaattaaa aatgaagttt   1320
tagcacgtgt cagtcctgct cctcggccac gaagtgcacg cagttgccgg ccgggtcgcg   1380
cagggcgaac tcccgccccc acggctgctc gccgatctcg gtcatggccg gcccggaggc   1440
gtcccggaag ttcgtggaca cgacctccga ccactcggcg tacagctcgt ccaggccgcg   1500
cacccacacc caggccaggg tgttgtccgg caccacctgg tcctggaccg cgctgatgaa   1560
cagggtcacg tcgtcccgga ccacaccggc gaagtcgtcc tccacgaagt cccgggagaa   1620
cccgagccgg tcggtccaga actcgaccgc tccggcgacg tcgcgcgcgg tgagcaccgg   1680
aacggcactg gtcaacttgg ccatggtggc cctcctcacg tgctattatt gaagcattta   1740
tcagggttat tgtctcatga gcggatacat atttgaatgt atttagaaaa ataaacaaat   1800
aggggttccg cgcacatttc cccgaaaagt gccacctgat gcggtgtgaa ataccgcaca   1860
gatgcgtaag gagaaaatac cgcatcagga aattgtaagc gttaataatt cagaagaact   1920
cgtcaagaag gcgatagaag gcgatgcgct gcgaatcggg agcggcgata ccgtaaagca   1980
cgaggaagcg gtcagcccat tcgccgccaa gctcttcagc aatatcacgg gtagccaacg   2040
ctatgtcctg atagcggtcc gccacaccca gccggccaca gtcgatgaat ccagaaaagc   2100
ggccattttc caccatgata ttcggcaagc aggcatcgcc atgggtcacg acgagatcct   2160
cgccgtcggg catgctcgcc ttgagcctgg cgaacagttc ggctggcgcg agcccctgat   2220
gctcttcgtc cagatcatcc tgatcgacaa gaccggcttc catccgagta cgtgctcgct   2280
cgatgcgatg tttcgcttgg tggtcgaatg ggcaggtagc cggatcaagc gtatgcagcc   2340
gccgcattgc atcagccatg atggatactt tctcggcagg agcaaggtga gatgacagga   2400
gatcctgccc cggcacttcg cccaatagca gccagtccct tcccgcttca gtgacaacgt   2460
cgagcacagc tgcgcaagga acgcccgtcg tggccagcca cgatagccgc gctgcctcgt   2520
```

-continued

```
cttgcagttc attcagggca ccggacaggt cggtcttgac aaaaagaacc gggcgcccct   2580
gcgctgacag ccggaacacg gcggcatcag agcagccgat tgtctgttgt gcccagtcat   2640
agccgaatag cctctccacc caagcggccg gagaacctgc gtgcaatcca tcttgttcaa   2700
tcatgcgaaa cgatcctcat cctgtctctt gatcagagct tgatcccctg cgccatcaga   2760
tccttggcgg caagaaagcc atccagttta ctttgcaggg cttcccaacc ttaccagagg   2820
gcgccccagc tggcaattcc ggttcgcttg ctgtccataa aaccgcccag tctagctatc   2880
gccatgtaag cccactgcaa gctacctgct ttctctttgc gcttgcgttt tcccttgtcc   2940
agatagccca gtagctgaca ttcatccggg gtcagcaccg tttctgcgga ctggctttct   3000
acgtgaaaag gatctaggtg aagatccttt ttgataatct catgcctgac atttatattc   3060
cccagaacat caggttaatg gcgtttttga tgtcattttc gcggtggctg agatcagcca   3120
cttcttcccc gataacggag accggcacac tggccatatc ggtggtcatc atgcgccagc   3180
tttcatcccc gatatgcacc accgggtaaa gttcacggga gactttatct gacagcagac   3240
gtgcactggc cagggggatc accatccgtc gccccggcgt gtcaataata tcactctgta   3300
catccacaaa cagacgataa cggctctctc ttttataggt gtaaacctta aactgccgta   3360
cgtataggct gcgcaactgt tgggaagggc gatcggtgcg ggcctcttcg ctattacgcc   3420
agctggcgaa agggggatgt gctgcaaggc gattaagttg ggtaacgcca gggttttccc   3480
agtcacgacg ttgtaaaacg acggccagtg aagcggccgc accatggtga aaaggccagc   3540
acttccgctg accgttgatg gtgtcaccta tgatgtgtct gcctggttga accatcatcc   3600
agggggtgct gacatcattg agaactaccg cggtcgtgat gccactgatg tctttatggt   3660
tatgcactct gaaaatgctg tgagtaaact aagaaggatg cctatcatgg aaccatcatc   3720
tccactgacg cctacgccac cgaaacccaa ctcagacgaa ccgcaggagg atttccgcaa   3780
gctccgagat gagctcatcg cagcaggaat gttcgacgca tcaccgatgt ggtacgcata   3840
taagacgctc agtacgctgg gcctcggggt cctcgcggtg ctattgatga cccagtggca   3900
ctggtacctc gtcggggcaa tcgtgttggg cattcacttc caacaaatgg gttggttgtc   3960
gcacgatatc tgccaccatc agctgttcaa ggaccgatcg atcaacaacg ccatcggctt   4020
gcttttcggg aacgtcttgc aagggttctc tgtgacctgg tggaaggaca ggcacaatgc   4080
acaccactcc gccaccaacg tgcaaggcca cgaccccgac attgacaacc tgccgctgct   4140
ggcatggtcc aaggaggacg tggagagggc cggcccgttc tcacggcgga ttatcaagta   4200
ccagcaatac tacttcttct tcatctgtgc cctcctgagg ttcatctggt gcttccagag   4260
catccacaca gccacgggcc tgaaggatcg cagcaaccag tactaccgca ggcagtacga   4320
gaaagagagc gtgggcctgg ccctccactg gggcctgaag gcgttgttct actactttta   4380
tatgccaagc ttcttgaccg gactcatggt gtttttcgtg tccgagttgc ttgggggctt   4440
cggcatcgcc atcgtggtgt tcatgaacca ctacccctg gagaagatcc aggactcggt   4500
gtgggacggc cacggctttt gcgccggcca gattcacgaa acgatgaacg tccagcgggg   4560
actcgtcacg gactggttct tcggtgggct gaattaccaa atcgagcacc acctgtggcc   4620
gacgctgccc cggcacaacc tgacggcggc cagcatcaaa gtggagcagt tgtgcaagaa   4680
gcacaacttg ccgtatcgca gcccccccaat gctggagggg gtgggcatcc tgatcagcta   4740
cctgggcacc tttgcccgca tggtggcaaa ggccgacaag gcgtaagcgg ccgc         4794
```

<210> SEQ ID NO 30
<211> LENGTH: 4794

-continued

<212> TYPE: DNA
<213> ORGANISM: Artificial Sequence
<220> FEATURE:
<223> OTHER INFORMATION: plasmid pLF120-3

<400> SEQUENCE: 30
ttgtaatacg actcactata gggcgaattg ggccctctag atgcatgctc gagcggccgc 60
cagtgtgatg gatatctgca gaattcaggc ctgaattcca gcacactggc ggccgttact 120
agtggatccg agctcggtac caagcttgat gcatagcttg agtattctaa cgcgtcacct 180
aaatagcttg gcgtaatcat ggtcatagct gtttcctgtg tgaaattgtt atccgctcac 240
aattccacac aacatacgag ccggaagcat aaagtgtaaa gcctggggtg cctaatgagt 300
gagctaactc acattaattg cgttgcgctc actgcccgct ttccagtcgg gaaacctgtc 360
gtgccagctg cattaatgaa tcggccaacg cgcggggaga ggcggtttgc gtattgggcg 420
ctcttccgct tcctcgctca ctgactcgct gcgctcggtc gttcggctgc ggcgagcggt 480
atcagctcac tcaaaggcgg taatacggtt atccacagaa tcaggggata acgcaggaaa 540
gaacatgtga gcaaaaggcc agcaaaaggc caggaaccgt aaaaaggccg cgttgctggc 600
gtttttccat aggctccgcc cccctgacga gcatcacaaa aatcgacgct caagtcagag 660
gtggcgaaac ccgacaggac tataaagata ccaggcgttt ccccctggaa gctccctcgt 720
gcgctctcct gttccgaccc tgccgcttac cggatacctg tccgcctttc tcccttcggg 780
aagcgtggcg ctttctcata gctcacgctg taggtatctc agttcggtgt aggtcgttcg 840
ctccaagctg ggctgtgtgc acgaaccccc cgttcagccc gaccgctgcg ccttatccgg 900
taactatcgt cttgagtcca acccggtaag acacgactta tcgccactgg cagcagccac 960
tggtaacagg attagcagag cgaggtatgt aggcggtgct acagagttct tgaagtggtg 1020
gcctaactac ggctacacta gaagaacagt atttggtatc tgcgctctgc tgaagccagt 1080
taccttcgga aaaagagttg gtagctcttg atccggcaaa caaaccaccg ctggtagcgg 1140
tggttttttt gtttgcaagc agcagattac gcgcagaaaa aaaggatctc aagaagatcc 1200
tttgatcttt tctacggggt ctgacgctca gtggaacgaa aactcacgtt aagggatttt 1260
ggtcatgaga ttatcaaaaa ggatcttcac ctagatcctt ttaaattaaa aatgaagttt 1320
tagcacgtgt cagtcctgct cctcggccac gaagtgcacg cagttgccgg ccgggtcgcg 1380
cagggcgaac tcccgccccc acggctgctc gccgatctcg gtcatggccg gcccggaggc 1440
gtcccggaag ttcgtggaca cgacctccga ccactcggcg tacagctcgt ccaggccgcg 1500
cacccacacc caggccaggg tgttgtccgg caccacctgg tcctggaccg cgctgatgaa 1560
cagggtcacg tcgtcccgga ccacaccggc gaagtcgtcc tccacgaagt cccgggagaa 1620
cccgagccgg tcggtccaga actcgaccgc tccggcgacg tcgcgcgcgg tgagcaccgg 1680
aacggcactg gtcaacttgg ccatggtggc cctcctcacg tgctattatt gaagcattta 1740
tcagggttat tgtctcatga gcggatacat atttgaatgt atttagaaaa ataaacaaat 1800
aggggttccg cgcacatttc cccgaaaagt gccacctgat gcggtgtgaa ataccgcaca 1860
gatgcgtaag gagaaaatac cgcatcagga aattgtaagc gttaatattt cagaagaact 1920
cgtcaagaag gcgatagaag gcgatgcgct gcgaatcggg agcggcgata ccgtaaagca 1980
cgaggaagcg gtcagcccat tcgccgccaa gctcttcagc aatatcacgg gtagccaacg 2040
ctatgtcctg atagcggtcc gccacaccca gccggccaca gtcgatgaat ccagaaaagc 2100
ggccattttc caccatgata ttcggcaagc aggcatcgcc atgggtcacg acgagatcct 2160

-continued

```
cgccgtcggg catgctcgcc ttgagcctgg cgaacagttc ggctggcgcg agcccctgat   2220
gctcttcgtc cagatcatcc tgatcgacaa gaccggcttc catccgagta cgtgctcgct   2280
cgatgcgatg tttcgcttgg tggtcgaatg ggcaggtagc cggatcaagc gtatgcagcc   2340
gccgcattgc atcagccatg atggatactt tctcggcagg agcaaggtga gatgacagga   2400
gatcctgccc cggcacttcg cccaatagca gccagtccct tcccgcttca gtgacaacgt   2460
cgagcacagc tgcgcaagga acgcccgtcg tggccagcca cgatagccgc gctgcctcgt   2520
cttgcagttc attcagggca ccggacaggt cggtcttgac aaaaagaacc gggcgcccct   2580
gcgctgacag ccggaacacg gcggcatcag agcagccgat tgtctgttgt gcccagtcat   2640
agccgaatag cctctccacc caagcggccg gagaacctgc gtgcaatcca tcttgttcaa   2700
tcatgcgaaa cgatcctcat cctgtctctt gatcagagct tgatcccctg cgccatcaga   2760
tccttggcgg caagaaagcc atccagttta ctttgcaggg cttcccaacc ttaccagagg   2820
gcgccccagc tggcaattcc ggttcgcttg ctgtccataa aaccgcccag tctagctatc   2880
gccatgtaag cccactgcaa gctacctgct ttctctttgc gcttgcgttt tcccttgtcc   2940
agatagccca gtagctgaca ttcatccggg gtcagcaccg tttctgcgga ctggctttct   3000
acgtgaaaag gatctaggtg aagatccttt ttgataatct catgcctgac atttatattc   3060
cccagaacat caggttaatg gcgtttttga tgtcattttc gcggtggctg agatcagcca   3120
cttcttcccc gataacggag accggcacac tggccatatc ggtggtcatc atgcgccagc   3180
tttcatcccc gatatgcacc accgggtaaa gttcacggga gactttatct gacagcagac   3240
gtgcactggc caggggggatc accatccgtc gccccggcgt gtcaataata tcactctgta   3300
catccacaaa cagacgataa cggctctctc ttttataggt gtaaacctta aactgccgta   3360
cgtataggct gcgcaactgt tgggaagggc gatcggtgcg ggcctcttcg ctattacgcc   3420
agctggcgaa agggggatgt gctgcaaggc gattaagttg ggtaacgcca gggttttccc   3480
agtcacgacg ttgtaaaacg acggccagtg aagcggccgc accatggtga aaaggccagc   3540
acttccgctg accgttgatg gtgtcaccta tgatgtgtct gcctggttga accatcatcc   3600
agggggtgct gacatcattg agaactaccg cggtcgtgat gccactgatg tctttatggt   3660
tatgcactct gaaaatgctg tgagtaaact aagaaggatg cctatcatgg aaccatcatc   3720
tccactgacg cctacgccac cgaaacccaa ctcagacgaa ccgcaggagg atttccgcaa   3780
gctccgagat gagctcatcg cagcaggaat gttcgacgca tcaccgatgt ggtacgcata   3840
taagacgctc agtacgctgg gcctcggggt cctcgcggtg ctattgatga cccagtggca   3900
ctggtacctc gtcggggcaa tcgtgttggg cattcacttc caacaaatgg gttggttgtc   3960
gcacgatatc tgccaccatc agctgttcaa ggaccgatcg atcaacaacg ccatcggctt   4020
gcttttcggg aacgtcttgc aagggttctc tgtgacctgg tggaaggaca ggcacaatgc   4080
acaccactcc gccaccaacg tgcaaggcca cgaccccgac attgacaacc tgccgctgct   4140
ggcatggtcc aaggaggacg tggagagggc cggcccgttc tcacggcgga tgatcaagta   4200
ccagcaatac tacttcttct tcatctgtgc cctcctgagg ttcatctggt gcttccagag   4260
catccacaca gccacgggcc tgaaggatcg cagcaaccag tactaccgca ggcagtacga   4320
gaaagagagc gtgggcctgg ccctccactg gggcctgaag gcgttgttct actactttta   4380
tatgccaagc ttcttgaccg gactcatggt gtttttcgtg tccgagttgc ttgggggctt   4440
cggcatcgcc atcgtggtgt tcatgaacca ctacccccctg gagaagatcc aggactcggt   4500
gtgggacggc cacggctttt gcgccggcca gattcacgaa acgatgaacg tccagcgggg   4560
```

-continued actcgtcacg gactggttct tcggtgggct gaattaccaa atcgagcacc acctgtggcc 4620
gacgctgccc cggcacaacc tgacggcggc cagcatcaaa gtggagcagt tgtgcaagaa 4680
gcacaacttg ccgtatcgca gccccccaat gctggagggg gtgggcatcc tgatcagcta 4740
cctgggcacc tttgcccgca tggtggcaaa ggccgacaag gcgtaagcgg ccgc 4794

<210> SEQ ID NO 31
<211> LENGTH: 4794
<212> TYPE: DNA
<213> ORGANISM: Artificial Sequence
<220> FEATURE:
<223> OTHER INFORMATION: plasmid pLF120-4

<400> SEQUENCE: 31
ttgtaatacg actcactata gggcgaattg ggccctctag atgcatgctc gagcggccgc 60
cagtgtgatg gatatctgca gaattcaggc ctgaattcca gcacactggc ggccgttact 120
agtggatccg agctcggtac caagcttgat gcatagcttg agtattctaa cgcgtcacct 180
aaatagcttg gcgtaatcat ggtcatagct gtttcctgtg tgaaattgtt atccgctcac 240
aattccacac aacatacgag ccggaagcat aaagtgtaaa gcctggggtg cctaatgagt 300
gagctaactc acattaattg cgttgcgctc actgcccgct ttccagtcgg gaaacctgtc 360
gtgccagctg cattaatgaa tcggccaacg cgcggggaga ggcggtttgc gtattgggcg 420
ctcttccgct tcctcgctca ctgactcgct gcgctcggtc gttcggctgc ggcgagcggt 480
atcagctcac tcaaaggcgg taatacggtt atccacagaa tcaggggata acgcaggaaa 540
gaacatgtga gcaaaaggcc agcaaaaggc caggaaccgt aaaaaggccg cgttgctggc 600
gtttttccat aggctccgcc cccctgacga gcatcacaaa aatcgacgct caagtcagag 660
gtggcgaaac ccgacaggac tataaagata ccaggcgttt ccccctggaa gctccctcgt 720
gcgctctcct gttccgaccc tgccgcttac cggatacctg tccgcctttc tcccttcggg 780
aagcgtggcg ctttctcata gctcacgctg taggtatctc agttcggtgt aggtcgttcg 840
ctccaagctg ggctgtgtgc acgaaccccc cgttcagccc gaccgctgcg ccttatccgg 900
taactatcgt cttgagtcca acccggtaag acacgactta tcgccactgg cagcagccac 960
tggtaacagg attagcagag cgaggtatgt aggcggtgct acagagttct tgaagtggtg 1020
gcctaactac ggctacacta gaagaacagt atttggtatc tgcgctctgc tgaagccagt 1080
taccttcgga aaaagagttg gtagctcttg atccggcaaa caaaccaccg ctggtagcgg 1140
tggttttttt gtttgcaagc agcagattac gcgcagaaaa aaaggatctc aagaagatcc 1200
tttgatcttt tctacggggt ctgacgctca gtggaacgaa aactcacgtt aagggatttt 1260
ggtcatgaga ttatcaaaaa ggatcttcac ctagatcctt ttaaattaaa aatgaagttt 1320
tagcacgtgt cagtcctgct cctcggccac gaagtgcacg cagttgccgg ccgggtcgcg 1380
cagggcgaac tcccgccccc acggctgctc gccgatctcg gtcatggccg gcccggaggc 1440
gtcccggaag ttcgtggaca cgacctccga ccactcggcg tacagctcgt ccaggccgcg 1500
cacccacacc caggccaggg tgttgtccgg caccacctgg tcctggaccg cgctgatgaa 1560
cagggtcacg tcgtcccgga ccacaccggc gaagtcgtcc tccacgaagt cccgggagaa 1620
cccgagccgg tcggtccaga actcgaccgc tccggcgacg tcgcgcgcgg tgagcaccgg 1680
aacggcactg gtcaacttgg ccatggtggc cctcctcacg tgctattatt gaagcattta 1740
tcagggttat tgtctcatga gcggatacat atttgaatgt atttagaaaa ataaacaaat 1800

-continued

```
aggggttccg cgcacatttc cccgaaaagt gccacctgat gcggtgtgaa ataccgcaca   1860
gatgcgtaag gagaaaatac cgcatcagga aattgtaagc gttaatattt cagaagaact   1920
cgtcaagaag gcgatagaag gcgatgcgct gcgaatcggg agcggcgata ccgtaaagca   1980
cgaggaagcg gtcagcccat tcgccgccaa gctcttcagc aatatcacgg gtagccaacg   2040
ctatgtcctg atagcggtcc gccacaccca gccggccaca gtcgatgaat ccagaaaagc   2100
ggccattttc caccatgata ttcggcaagc aggcatcgcc atgggtcacg acgagatcct   2160
cgccgtcggg catgctcgcc ttgagcctgg cgaacagttc ggctggcgcg agcccctgat   2220
gctcttcgtc cagatcatcc tgatcgacaa gaccggcttc catccgagta cgtgctcgct   2280
cgatgcgatg tttcgcttgg tggtcgaatg ggcaggtagc cggatcaagc gtatgcagcc   2340
gccgcattgc atcagccatg atggatactt tctcggcagg agcaaggtga gatgacagga   2400
gatcctgccc cggcacttcg cccaatagca gccagtccct tcccgcttca gtgacaacgt   2460
cgagcacagc tgcgcaagga acgcccgtcg tggccagcca cgatagccgc gctgcctcgt   2520
cttgcagttc attcagggca ccggacaggt cggtcttgac aaaaagaacc gggcgcccct   2580
gcgctgacag ccggaacacg gcggcatcag agcagccgat tgtctgttgt gcccagtcat   2640
agccgaatag cctctccacc caagcggccg gagaacctgc gtgcaatcca tcttgttcaa   2700
tcatgcgaaa cgatcctcat cctgtctctt gatcagagct tgatcccctg cgccatcaga   2760
tccttggcgg caagaaagcc atccagttta ctttgcaggg cttcccaacc ttaccagagg   2820
gcgccccagc tggcaattcc ggttcgcttg ctgtccataa aaccgcccag tctagctatc   2880
gccatgtaag cccactgcaa gctacctgct ttctctttgc gcttgcgttt tcccttgtcc   2940
agatagccca gtagctgaca ttcatccggg gtcagcaccg tttctgcgga ctggctttct   3000
acgtgaaaag gatctaggtg aagatccttt ttgataatct catgcctgac atttatattc   3060
cccagaacat caggttaatg gcgtttttga tgtcattttc gcggtggctg agatcagcca   3120
cttcttcccc gataacggag accggcacac tggccatatc ggtggtcatc atgcgccagc   3180
tttcatcccc gatatgcacc accgggtaaa gttcacggga gactttatct gacagcagac   3240
gtgcactggc cagggggatc accatccgtc gccccggcgt gtcaataata tcactctgta   3300
catccacaaa cagacgataa cggctctctc ttttataggt gtaaacctta aactgccgta   3360
cgtataggct gcgcaactgt tgggaagggc gatcggtgcg ggcctcttcg ctattacgcc   3420
agctggcgaa agggggatgt gctgcaaggc gattaagttg ggtaacgcca gggttttccc   3480
agtcacgacg ttgtaaaacg acggccagtg aagcggccgc accatggtga aaaggccagc   3540
acttccgctg accgttgatg gtgtcaccta tgatgtgtct gcctggttga accatcatcc   3600
agggggtgct gacatcattg agaactaccg cggtcgtgat gccactgatg tctttatggt   3660
tatgcactct gaaaatgctg tgagtaaact aagaaggatg cctatcatgg aaccatcatc   3720
tccactgacg cctacgccac cgaaacccaa ctcagacgaa ccgcaggagg atttccgcaa   3780
gctccgagat gagctcatcg cagcaggaat gttcgacgca tcaccgatgt ggtacgcata   3840
taagacgctc agtacgctgg gcctcggggt cctcgcggtg ctattgatga cccagtggca   3900
ctggtacctc gtcggggcaa tcgtgttggg cattcacttc caacaaatgg gttggttgtc   3960
gcacgatatc tgccaccatc agctgttcaa ggaccgatcg atcaacaacg ccatcggctt   4020
gcttttcggg aacgtcttgc aagggttctc tgtgacctgg tggaaggaca ggcacaatgc   4080
acaccactcc gccaccaacg tgcaaggcca cgaccccgac attgacaacc tgccgctgct   4140
ggcatggtcc aaggaggacg tggagagggc cggcccgttc tcacggcgga tgatcaagta   4200
```

-continued ccagcaatac tacttcttct tcatctgtgc cctcctgagg ttcatctggt gcttccagag 4260
catccacaca gccacgggcc tgaaggatcg cagcaaccag tactaccgca ggcagtacga 4320
gaaagagagc gtgggcctgg ccctccactg gggcctgaag gcgttgttct actactttta 4380
tatgccaagc ttcttgaccg gactcatggt gtttttcgtg tccgagttgc ttgggggctt 4440
cggcatcgcc atcgtggtgt tcatgaacca ctacccccctg gagaagatcc aggactcggt 4500
gtgggacggc cacggctttt gcgccggcca gattcacgaa acgatgaacg tccagcgggg 4560
actcgtcacg gactggttct tcggtgggct gaattaccaa atcgagcacc acctgtggcc 4620
gacgctgccc cggcacaacc tgacggcggc cagcatcaaa gtggagcagt tgtgcaagaa 4680
gcacaacttg ccgtatcgca gccccccaat gctggagggg gtgggcatcc tgatcagcta 4740
cctgggcacc tttgcccgca tggtggcaaa ggccgacaag gcgtaagcgg ccgc 4794

<210> SEQ ID NO 32
<211> LENGTH: 9472
<212> TYPE: DNA
<213> ORGANISM: Artificial Sequence
<220> FEATURE:
<223> OTHER INFORMATION: plsmid pDMW263

<400> SEQUENCE: 32
catggcatgg atggtacgtc ctgtagaaac cccaacccgt gaaatcaaaa aactcgacgg 60
cctgtgggca ttcagtctgg atcgcgaaaa ctgtggaatt gatcagcgtt ggtgggaaag 120
cgcgttacaa gaaagccggg caattgctgt gccaggcagt tttaacgatc agttcgccga 180
tgcagatatt cgtaattatg cgggcaacgt ctggtatcag cgcgaagtct ttataccgaa 240
aggttgggca ggccagcgta tcgtgctgcg tttcgatgcg gtcactcatt acggcaaagt 300
gtgggtcaat aatcaggaag tgatggagca tcagggcggc tatacgccat ttgaagccga 360
tgtcacgccg tatgttattg ccgggaaaag tgtacgtatc accgtttgtg tgaacaacga 420
actgaactgg cagactatcc cgccgggaat ggtgattacc gacgaaaacg gcaagaaaaa 480
gcagtcttac ttccatgatt tctttaacta tgccgggatc catcgcagcg taatgctcta 540
caccacgccg aacacctggg tggacgatat caccgtggtg acgcatgtcg cgcaagactg 600
taaccacgcg tctgttgact ggcaggtggt ggccaatggt gatgtcagcg ttgaactgcg 660
tgatgcggat caacaggtgg ttgcaactgg acaaggcact agcgggactt tgcaagtggt 720
gaatccgcac ctctggcaac cgggtgaagg ttatctctat gaactgtgcg tcacagccaa 780
aagccagaca gagtgtgata tctacccgct tcgcgtcggc atccggtcag tggcagtgaa 840
gggcgaacag ttcctgatta accacaaacc gttctacttt actggctttg gtcgtcatga 900
agatgcggac ttacgtggca aaggattcga taacgtgctg atggtgcacg accacgcatt 960
aatggactgg attggggcca actcctaccg tacctcgcat taccccttacg ctgaagagat 1020 gctcgactgg gcagatgaac atggcatcgt ggtgattgat gaaactgctg ctgtcggctt 1080
taacctctct ttaggcattg gtttcgaagc gggcaacaag ccgaaagaac tgtacagcga 1140
agaggcagtc aacggggaaa ctcagcaagc gcacttacag gcgattaaag agctgatagc 1200
gcgtgacaaa aaccacccaa gcgtggtgat gtggagtatt gccaacgaac cggatacccg 1260
tccgcaagtg cacgggaata tttcgccact ggcggaagca acgcgtaaac tcgacccgac 1320
gcgtccgatc acctgcgtca atgtaatgtt ctgcgacgct cacaccgata ccatcagcga 1380
tctctttgat gtgctgtgcc tgaaccgtta ttacggatgg tatgtccaaa gcggcgattt 1440

-continued ggaaacggca gagaaggtac tggaaaaaga acttctggcc tggcaggaga aactgcatca 1500
gccgattatc atcaccgaat acggcgtgga tacgttagcc gggctgcact caatgtacac 1560
cgacatgtgg agtgaagagt atcagtgtgc atggctggat atgtatcacc gcgtctttga 1620
tcgcgtcagc gccgtcgtcg gtgaacaggt atggaatttc gccgattttg cgacctcgca 1680
aggcatattg cgcgttggcg gtaacaagaa agggatcttc actcgcgacc gcaaaccgaa 1740
gtcggcggct tttctgctgc aaaaacgctg gactggcatg aacttcggtg aaaaaccgca 1800
gcagggaggc aaacaatgat taattaacta gagcggccgc caccgcggcc cgagattccg 1860
gcctcttcgg ccgccaagcg acccgggtgg acgtctagag gtacctagca attaacagat 1920
agtttgccgg tgataattct cttaacctcc cacactcctt tgacataacg atttatgtaa 1980
cgaaactgaa atttgaccag atattgtgtc cgcggtggag ctccagcttt tgttcccttt 2040
agtgagggtt aatttcgagc ttggcgtaat catggtcata gctgtttcct gtgtgaaatt 2100
gttatccgct cacaattcca cacaacatac gagccggaag cataaagtgt aaagcctggg 2160
gtgcctaatg agtgagctaa ctcacattaa ttgcgttgcg ctcactgccc gctttccagt 2220
cgggaaacct gtcgtgccag ctgcattaat gaatcggcca acgcgcgggg agaggcggtt 2280
tgcgtattgg gcgctcttcc gcttcctcgc tcactgactc gctgcgctcg gtcgttcggc 2340
tgcggcgagc ggtatcagct cactcaaagg cggtaatacg gttatccaca gaatcagggg 2400
ataacgcagg aaagaacatg tgagcaaaag gccagcaaaa ggccaggaac cgtaaaaagg 2460
ccgcgttgct ggcgtttttc cataggctcc gcccccctga cgagcatcac aaaaatcgac 2520
gctcaagtca gaggtggcga aacccgacag gactataaag ataccaggcg tttccccctg 2580
gaagctccct cgtgcgctct cctgttccga ccctgccgct taccggatac ctgtccgcct 2640
ttctcccttc gggaagcgtg gcgctttctc atagctcacg ctgtaggtat ctcagttcgg 2700
tgtaggtcgt tcgctccaag ctgggctgtg tgcacgaacc ccccgttcag cccgaccgct 2760
gcgccttatc cggtaactat cgtcttgagt ccaacccggt aagacacgac ttatcgccac 2820
tggcagcagc cactggtaac aggattagca gagcgaggta tgtaggcggt gctacagagt 2880
tcttgaagtg gtggcctaac tacggctaca ctagaaggac agtatttggt atctgcgctc 2940
tgctgaagcc agttaccttc ggaaaaagag ttggtagctc ttgatccggc aaacaaacca 3000
ccgctggtag cggtggtttt tttgtttgca agcagcagat tacgcgcaga aaaaaaggat 3060
ctcaagaaga tcctttgatc ttttctacgg ggtctgacgc tcagtggaac gaaaactcac 3120
gttaagggat tttggtcatg agattatcaa aaaggatctt cacctagatc cttttaaatt 3180
aaaaatgaag ttttaaatca atctaaagta tatatgagta aacttggtct gacagttacc 3240
aatgcttaat cagtgaggca cctatctcag cgatctgtct atttcgttca tccatagttg 3300
cctgactccc cgtcgtgtag ataactacga tacgggaggg cttaccatct ggccccagtg 3360
ctgcaatgat accgcgagac ccacgctcac cggctccaga tttatcagca ataaaccagc 3420
cagccggaag ggccgagcgc agaagtggtc ctgcaacttt atccgcctcc atccagtcta 3480
ttaattgttg ccgggaagct agagtaagta gttcgccagt taatagtttg cgcaacgttg 3540
ttgccattgc tacaggcatc gtggtgtcac gctcgtcgtt tggtatggct tcattcagct 3600
ccggttccca acgatcaagg cgagttacat gatcccccat gttgtgcaaa aaagcggtta 3660
gctccttcgg tcctccgatc gttgtcagaa gtaagttggc cgcagtgtta tcactcatgg 3720
ttatggcagc actgcataat tctcttactg tcatgccatc cgtaagatgc ttttctgtga 3780
ctggtgagta ctcaaccaag tcattctgag aatagtgtat gcggcgaccg agttgctctt 3840

-continued gcccggcgtc aatacgggat aataccgcgc cacatagcag aactttaaaa gtgctcatca 3900
ttggaaaacg ttcttcgggg cgaaaactct caaggatctt accgctgttg agatccagtt 3960
cgatgtaacc cactcgtgca cccaactgat cttcagcatc ttttactttc accagcgttt 4020
ctgggtgagc aaaaacagga aggcaaaatg ccgcaaaaaa gggaataagg gcgacacgga 4080
aatgttgaat actcatactc ttcctttttc aatattattg aagcatttat cagggttatt 4140
gtctcatgag cggatacata tttgaatgta tttagaaaaa taaacaaata ggggttccgc 4200
gcacatttcc ccgaaaagtg ccacctgacg cgccctgtag cggcgcatta agcgcggcgg 4260
gtgtggtggt tacgcgcagc gtgaccgcta cacttgccag cgccctagcg cccgctcctt 4320
tcgctttctt cccttccttt ctcgccacgt tcgccggctt tccccgtcaa gctctaaatc 4380
gggggctccc tttagggttc cgatttagtg ctttacggca cctcgacccc aaaaaacttg 4440
attagggtga tggttcacgt agtgggccat cgccctgata gacggttttt cgccctttga 4500
cgttggagtc cacgttcttt aatagtggac tcttgttcca aactggaaca acactcaacc 4560
ctatctcggt ctattctttt gatttataag ggattttgcc gatttcggcc tattggttaa 4620
aaaatgagct gatttaacaa aaatttaacg cgaattttaa caaaatatta acgcttacaa 4680
tttccattcg ccattcaggc tgcgcaactg ttgggaaggg cgatcggtgc gggcctcttc 4740
gctattacgc cagctggcga aagggggatg tgctgcaagg cgattaagtt gggtaacgcc 4800
agggttttcc cagtcacgac gttgtaaaac gacggccagt gaattgtaat acgactcact 4860
atagggcgaa ttgggtaccg ggcccccct cgaggtcgat ggtgtcgata agcttgatat 4920
cgaattcatg tcacacaaac cgatcttcgc ctcaaggaaa cctaattcta catccgagag 4980
actgccgaga tccagtctac actgattaat tttcgggcca ataatttaaa aaaatcgtgt 5040
tatataatat tatatgtatt atatatatac atcatgatga tactgacagt catgtcccat 5100
tgctaaatag acagactcca tctgccgcct ccaactgatg ttctcaatat ttaaggggtc 5160
atctcgcatt gtttaataat aaacagactc catctaccgc ctccaaatga tgttctcaaa 5220
atatattgta tgaacttatt tttattactt agtattatta gacaacttac ttgctttatg 5280
aaaaacactt cctatttagg aaacaattta taatggcagt tcgttcattt aacaatttat 5340
gtagaataaa tgttataaat gcgtatggga aatcttaaat atggatagca taaatgatat 5400
ctgcattgcc taattcgaaa tcaacagcaa cgaaaaaaat cccttgtaca acataaatag 5460
tcatcgagaa atatcaacta tcaaagaaca gctattcaca cgttactatt gagattatta 5520
ttggacgaga atcacacact caactgtctt tctctcttct agaaatacag gtacaagtat 5580
gtactattct cattgttcat acttctagtc atttcatccc acatattcct tggatttctc 5640
tccaatgaat gacattctat cttgcaaatt caacaattat aataagatat accaaagtag 5700
cggtatagtg gcaatcaaaa agcttctctg gtgtgcttct cgtatttatt tttattctaa 5760
tgatccatta aaggtatata tttatttctt gttatataat ccttttgttt attacatggg 5820
ctggatacat aaaggtattt tgatttaatt ttttgcttaa attcaatccc ccctcgttca 5880
gtgtcaactg taatggtagg aaattaccat acttttgaag aagcaaaaaa aatgaaagaa 5940
aaaaaaaatc gtatttccag gttagacgtt ccgcagaatc tagaatgcgg tatgcggtac 6000
attgttcttc gaacgtaaaa gttgcgctcc ctgagatatt gtacattttt gcttttacaa 6060
gtacaagtac atcgtacaac tatgtactac tgttgatgca tccacaacag tttgttttgt 6120
ttttttttgt tttttttttt tctaatgatt cattaccgct atgtatacct acttgtactt 6180

-continued

```
gtagtaagcc gggttattgg cgttcaatta atcatagact tatgaatctg cacggtgtgc   6240
gctgcgagtt acttttagct tatgcatgct acttgggtgt aatattggga tctgttcgga   6300
aatcaacgga tgctcaaccg atttcgacag taataatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
taaaacaaat gaaaagaaat acagttcttt gtatcatttg taacaattac cctgtacaaa   6600
ctaaggtatt gaaatcccac aatattccca aagtccaccc ctttccaaat tgtcatgcct   6660
acaactcata taccaagcac taacctacca aacaccacta aaaccccaca aaatatatct   6720
taccgaatat acagtaacaa gctaccacca cactcgttgg gtgcagtcgc cagcttaaag   6780
atatctatcc acatcagcca caactccctt cctttaataa accgactaca cccttggcta   6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg ccctttttat agagtcttat   7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
ttgagcatca tggcggcaga cagaatggtg gcaatggggt tgaccttctg cttgccgaga   7320
tcgggggcag atccgtgaca gggctcgtac agaccgaacg cctcgttggt gtcgggcaga   7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg   7800
atgaagtcgg tgccctcaac gtttcggatg gggagagat cggcgagctt gggcgacagc   7860
agctggcagg gtcgcaggtt ggcgtacagg ttcaggtcct ttcgcagctt gaggagaccc   7920
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaacagt   8520
gtacgcagat ctactataga ggaacattta aattgccccg gagaagacgg ccaggccgcc   8580
```

-continued

```
tagatgacaa attcaacaac tcacagctga ctttctgcca ttgccactag ggggggcct   8640

ttttatatgg ccaagccaag ctctccacgt cggttgggct gcacccaaca ataaatgggt   8700

agggttgcac caacaaaggg atgggatggg gggtagaaga tacgaggata acggggctca   8760

atggcacaaa taagaacgaa tactgccatt aagactcgtg atccagcgac tgacaccatt   8820

gcatcatcta agggcctcaa aactacctcg gaactgctgc gctgatctgg acaccacaga   8880

ggttccgagc actttaggtt gcaccaaatg tcccaccagg tgcaggcaga aaacgctgga   8940

acagcgtgta cagtttgtct taacaaaaag tgagggcgct gaggtcgagc agggtggtgt   9000

gacttgttat agcctttaga gctgcgaaag cgcgtatgga tttggctcat caggccagat   9060

tgagggtctg tggacacatg tcatgttagt gtacttcaat cgccccctgg atatagcccc   9120

gacaataggc cgtggcctca tttttttgcc ttccgcacat ttccattgct cgatacccac   9180

accttgcttc tcctgcactt gccaacctta atactggttt acattgacca acatcttaca   9240

agcggggggc ttgtctaggg tatatataaa cagtggctct cccaatcggt tgccagtctc   9300

ttttttcctt tctttcccca cagattcgaa atctaaacta cacatcacag aattccgagc   9360

cgtgagtatc cacgacaaga tcagtgtcga gacgacgcgt tttgtgtaat gacacaatcc   9420

gaaagtcgct agcaacacac actctctaca caaactaacc cagctctggt ac           9472
```

<210> SEQ ID NO 33
<211> LENGTH: 7879
<212> TYPE: DNA
<213> ORGANISM: Artificial Sequence
<220> FEATURE:
<223> OTHER INFORMATION: plasmid pDMW237

<400> SEQUENCE: 33

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc gggcaacggt ttcacttgag tgcagtggct    240

agtgctctta ctcgtacagt gtgcaatact gcgtatcata gtctttgatg tatatcgtat    300

tcattcatgt tagttgcgta cgagccggaa gcataaagtg taaagcctgg ggtgcctaat    360

gagtgagcta actcacatta attgcgttgc gctcactgcc cgctttccag tcgggaaacc    420

tgtcgtgcca gctgcattaa tgaatcggcc aacgcgcggg gagaggcggt ttgcgtattg    480

ggcgctcttc cgcttcctcg ctcactgact cgctgcgctc ggtcgttcgg ctgcggcgag    540

cggtatcagc tcactcaaag gcggtaatac ggttatccac agaatcaggg gataacgcag    600

gaaagaacat gtgagcaaaa ggccagcaaa aggccaggaa ccgtaaaaag gccgcgttgc    660

tggcgttttt ccataggctc cgcccccctg acgagcatca caaaaatcga cgctcaagtc    720

agaggtggcg aaacccgaca ggactataaa gataccaggc gtttccccct ggaagctccc    780

tcgtgcgctc tcctgttccg accctgccgc ttaccggata cctgtccgcc tttctccctt    840

cgggaagcgt ggcgctttct catagctcac gctgtaggta tctcagttcg gtgtaggtcg    900

ttcgctccaa gctgggctgt gtgcacgaac cccccgttca gcccgaccgc tgcgccttat    960

ccggtaacta tcgtcttgag tccaacccgg taagacacga cttatcgcca ctggcagcag   1020

ccactggtaa caggattagc agagcgaggt atgtaggcgg tgctacagag ttcttgaagt   1080

ggtggcctaa ctacggctac actagaagga cagtatttgg tatctgcgct ctgctgaagc   1140
```

-continued

```
cagttacctt cggaaaaaga gttggtagct cttgatccgg caaacaaacc accgctggta   1200

gcggtggttt ttttgtttgc aagcagcaga ttacgcgcag aaaaaaagga tctcaagaag   1260

atcctttgat cttttctacg gggtctgacg ctcagtggaa cgaaaactca cgttaaggga   1320

ttttggtcat gagattatca aaaaggatct tcacctagat ccttttaaat taaaaatgaa   1380

gttttaaatc aatctaaagt atatatgagt aaacttggtc tgacagttac caatgcttaa   1440

tcagtgaggc acctatctca gcgatctgtc tatttcgttc atccatagtt gcctgactcc   1500

ccgtcgtgta gataactacg atacgggagg gcttaccatc tggccccagt gctgcaatga   1560

taccgcgaga cccacgctca ccggctccag atttatcagc aataaaccag ccagccggaa   1620

gggccgagcg cagaagtggt cctgcaactt tatccgcctc catccagtct attaattgtt   1680

gccgggaagc tagagtaagt agttcgccag ttaatagttt gcgcaacgtt gttgccattg   1740

ctacaggcat cgtggtgtca cgctcgtcgt ttggtatggc ttcattcagc tccggttccc   1800

aacgatcaag gcgagttaca tgatccccca tgttgtgcaa aaaagcggtt agctccttcg   1860

gtcctccgat cgttgtcaga agtaagttgg ccgcagtgtt atcactcatg gttatggcag   1920

cactgcataa ttctcttact gtcatgccat ccgtaagatg cttttctgtg actggtgagt   1980

actcaaccaa gtcattctga gaatagtgta tgcggcgacc gagttgctct tgcccggcgt   2040

caatacggga taataccgcg ccacatagca gaactttaaa agtgctcatc attggaaaac   2100

gttcttcggg gcgaaaactc tcaaggatct taccgctgtt gagatccagt tcgatgtaac   2160

ccactcgtgc acccaactga tcttcagcat cttttacttt caccagcgtt tctgggtgag   2220

caaaaacagg aaggcaaaat gccgcaaaaa agggaataag ggcgacacgg aaatgttgaa   2280

tactcatact cttccttttt caatattatt gaagcattta tcagggttat tgtctcatga   2340

gcggatacat atttgaatgt atttagaaaa ataaacaaat aggggttccg cgcacatttc   2400

cccgaaaagt gccacctgac gcgccctgta gcggcgcatt aagcgcggcg ggtgtggtgg   2460

ttacgcgcag cgtgaccgct acacttgcca gcgccctagc gcccgctcct ttcgctttct   2520

tcccttcctt tctcgccacg ttcgccggct ttccccgtca agctctaaat cgggggctcc   2580

ctttagggtt ccgatttagt gctttacggc acctcgaccc caaaaaactt gattagggtg   2640

atggttcacg tagtgggcca tcgccctgat agacggtttt tcgccctttg acgttggagt   2700

ccacgttctt taatagtgga ctcttgttcc aaactggaac aacactcaac cctatctcgg   2760

tctattcttt tgatttataa gggattttgc cgatttcggc ctattggtta aaaaatgagc   2820

tgatttaaca aaaatttaac gcgaatttta acaaaatatt aacgcttaca atttccattc   2880

gccattcagg ctgcgcaact gttgggaagg gcgatcggtg cgggcctctt cgctattacg   2940

ccagctggcg aaagggggat gtgctgcaag gcgattaagt tgggtaacgc cagggttttc   3000

ccagtcacga cgttgtaaaa cgacggccag tgaattgtaa tacgactcac tatagggcga   3060

attgggtacc gggccccccc tcgaggtcga tggtgtcgat aagcttgata tcgaattcat   3120

gtcacacaaa ccgatcttcg cctcaaggaa acctaattct acatccgaga gactgccgag   3180

atccagtcta cactgattaa ttttcgggcc aataatttaa aaaaatcgtg ttatataata   3240

ttatatgtat tatatatata catcatgatg atactgacag tcatgtccca ttgctaaata   3300

gacagactcc atctgccgcc tccaactgat gttctcaata tttaaggggt catctcgcat   3360

tgtttaataa taaacagact ccatctaccg cctccaaatg atgttctcaa aatatattgt   3420

atgaacttat ttttattact tagtattatt agacaactta cttgctttat gaaaaacact   3480

tcctatttag gaaacaattt ataatggcag ttcgttcatt taacaattta tgtagaataa   3540
```

-continued

```
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
ttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
```

-continued

```
ttgttgtcgg ccaaccgcgc cgaaaacgca gctgtcagac ccacagcctc caacgaagaa   5940

tgtatcgtca aagtgatcca agcacactca tagttggagt cgtactccaa aggcggcaat   6000

gacgagtcag acagatactc gtcgactcag gcgacgacgg aattcctgca gcccatctgc   6060

agaattcagg agagaccggg ttggcggcgt atttgtgtcc caaaaaacag ccccaattgc   6120

cccggagaag acggccaggc cgcctagatg acaaattcaa caactcacag ctgactttct   6180

gccattgcca ctaggggggg gcctttttat atggccaagc caagctctcc acgtcggttg   6240

ggctgcaccc aacaataaat gggtagggtt gcaccaacaa agggatggga tgggggtag    6300

aagatacgag gataacgggg ctcaatggca caaataagaa cgaatactgc cattaagact   6360

cgtgatccag cgactgacac cattgcatca tctaagggcc tcaaaactac ctcggaactg   6420

ctgcgctgat ctggacacca cagaggttcc gagcacttta ggttgcacca aatgtcccac   6480

caggtgcagg cagaaaacgc tggaacagcg tgtacagttt gtcttaacaa aaagtgaggg   6540

cgctgaggtc gagcagggtg gtgtgacttg ttatagcctt tagagctgcg aaagcgcgta   6600

tggatttggc tcatcaggcc agattgaggg tctgtggaca catgtcatgt tagtgtactt   6660

caatcgcccc ctggatatag ccccgacaat aggccgtggc ctcatttttt tgccttccgc   6720

acatttccat tgctcggtac ccacaccttg cttctcctgc acttgccaac cttaatactg   6780

gtttacattg accaacatct tacaagcggg gggcttgtct agggtatata taaacagtgg   6840

ctctcccaat cggttgccag tctctttttt cctttctttc cccacagatt cgaaatctaa   6900

actacacatc acacaatgcc tgttactgac gtccttaagc gaaagtccgg tgtcatcgtc   6960

ggcgacgatg tccgagccgt gagtatccac gacaagatca gtgtcgagac gacgcgtttt   7020

gtgtaatgac acaatccgaa agtcgctagc aacacacact ctctacacaa actaacccag   7080

ctctccatgg ctctggccaa cgacgctggc gagcgaatct gggctgccgt caccgatccc   7140

gaaatcctca ttggcacctt ctcctacctg ctcctgaagc ctctcctgcg aaactctggt   7200

ctcgtggacg agaagaaagg agcctaccga acctccatga tctggtacaa cgtcctcctg   7260

gctctcttct ctgccctgtc cttctacgtg actgccaccg ctctcggctg ggactacggt   7320

actggagcct ggctgcgaag acagaccggt gatactcccc agcctctctt tcagtgtccc   7380

tctcctgtct gggactccaa gctgttcacc tggactgcca aggccttcta ctattctaag   7440

tacgtggagt acctcgacac cgcttggctg gtcctcaagg gcaagcgagt gtcctttctg   7500

caggccttcc atcactttgg agctccctgg gacgtctacc tcggcattcg actgcacaac   7560

gagggtgtgt ggatcttcat gttctttaac tcgttcattc acaccatcat gtacacctac   7620

tatggactga ctgccgctgg ctacaagttc aaggccaagc ctctgatcac tgccatgcag   7680

atttgccagt tcgtcggtgg ctttctcctg gtctgggact acatcaacgt tccctgcttc   7740

aactctgaca agggcaagct gttctcctgg gctttcaact acgcctacgt cggatctgtc   7800

tttctcctgt tctgtcactt cttttaccag gacaacctgg ccaccaagaa atccgctaag   7860

gctggtaagc agctttagc                                                7879
```

<210> SEQ ID NO 34
<211> LENGTH: 7783
<212> TYPE: DNA
<213> ORGANISM: Artificial Sequence
<220> FEATURE:
<223> OTHER INFORMATION: plasmid pY115

<400> SEQUENCE: 34

```
catggctctg gccaacgacg ctggcgagcg aatctgggct gccgtcaccg atcccgaaat     60
```

-continued

```
cctcattggc accttctcct acctgctcct gaagcctctc ctgcgaaact ctggtctcgt    120
ggacgagaag aaaggagcct accgaacctc catgatctgg tacaacgtcc tcctggctct    180
cttctctgcc ctgtccttct acgtgactgc caccgctctc ggctgggact acggtactgg    240
agcctggctg cgaagacaga ccggtgatac tccccagcct ctctttcagt gtccctctcc    300
tgtctgggac tccaagctgt tcacctggac tgccaaggcc ttctactatt ctaagtacgt    360
ggagtacctc gacaccgctt ggctggtcct caagggcaag cgagtgtcct ttctgcaggc    420
cttccatcac tttggagctc cctgggacgt ctacctcggc attcgactgc acaacgaggg    480
tgtgtggatc ttcatgttct ttaactcgtt cattcacacc atcatgtaca cctactatgg    540
actgactgcc gctggctaca agttcaaggc caagcctctg atcactgcca tgcagatttg    600
ccagttcgtc ggtggctttc tcctggtctg ggactacatc aacgttccct gcttcaactc    660
tgacaagggc aagctgttct cctgggcttt caactacgcc tacgtcggat ctgtctttct    720
cctgttctgt cacttctttt accaggacaa cctggccacc aagaaatccg ctaaggctgg    780
taagcagctt tagcggccgc aagtgtggat ggggaagtga gtgcccggtt ctgtgtgcac    840
aattggcaat ccaagatgga tggattcaac acagggatat agcgagctac gtggtggtgc    900
gaggatatag caacggatat ttatgtttga cacttgagaa tgtacgatac aagcactgtc    960
caagtacaat actaaacata ctgtacatac tcatactcgt acccgggcaa cggtttcact   1020
tgagtgcagt ggctagtgct cttactcgta cagtgtgcaa tactgcgtat catagtcttt   1080
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta aagtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
```

-continued

```
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg tttttcgccc   3480
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttatttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct taaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
agtagcggta tagtggcaat caaaaagctt ctctggtgtg cttctcgtat ttatttttat   4740
tctaatgatc cattaaaggt atatatttat ttcttgttat ataatccttt tgtttattac   4800
```

-continued

```
atgggctgga tacataaagg tattttgatt taatttttg cttaaattca atcccccctc   4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca tttttgcttt   5040
tacaagtaca agtacatcgt acaactatgt actactgttg atgcatccac aacagtttgt   5100
tttgtttttt tttgtttttt ttttttctaa tgattcatta ccgctatgta tacctacttg   5160
tacttgtagt aagccgggtt attggcgttc aattaatcat agacttatga atctgcacgg   5220
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
tctaacagtt aatcttctgg taagcctccc agccagcctt ctggtatcgc ttggcctcct   5640
caataggatc tcggttctgg ccgtacagac ctcggccgac aattatgata tccgttccgg   5700
tagacatgac atcctcaaca gttcggtact gctgtccgag agcgtctccc ttgtcgtcaa   5760
gacccacccc gggggtcaga ataagccagt cctcagagtc gcccttaggt cggttctggg   5820
caatgaagcc aaccacaaac tcggggtcgg atcgggcaag ctcaatggtc tgcttggagt   5880
actcgccagt ggccagagag cccttgcaag acagctcggc cagcatgagc agacctctgg   5940
ccagcttctc gttgggagag gggactagga actccttgta ctgggagttc tcgtagtcag   6000
agacgtcctc cttcttctgt tcagagacag tttcctcggc accagctcgc aggccagcaa   6060
tgattccggt tccgggtaca ccgtgggcgt tggtgatatc ggaccactcg gcgattcggt   6120
gacaccggta ctggtgcttg acagtgttgc caatatctgc gaactttctg tcctcgaaca   6180
ggaagaaacc gtgcttaaga gcaagttcct tgaggggggag cacagtgccg gcgtaggtga   6240
agtcgtcaat gatgtcgata tgggttttga tcatgcacac ataaggtccg accttatcgg   6300
caagctcaat gagctccttg gtggtggtaa catccagaga agcacacagg ttggttttct   6360
tggctgccac gagcttgagc actcgagcgg caaaggcgga cttgtggacg ttagctcgag   6420
cttcgtagga gggcattttg gtggtgaaga ggagactgaa ataaatttag tctgcagaac   6480
tttttatcgg aaccttatct ggggcagtga agtatatgtt atggtaatag ttacgagtta   6540
gttgaactta tagatagact ggactatacg gctatcggtc caaattagaa agaacgtcaa   6600
tggctctctg ggcgtcgcct ttgccgacaa aaatgtgatc atgatgaaag ccagcaatga   6660
cgttgcagct gatattgttg tcggccaacc gcgccgaaaa cgcagctgtc agacccacag   6720
cctccaacga agaatgtatc gtcaaagtga tccaagcaca ctcatagttg gagtcgtact   6780
ccaaaggcgg caatgacgag tcagacagat actcgtcgac gtttaaacag tgtacgcaga   6840
tctactatag aggaacattt aaattgcccc ggagaagacg gccaggccgc ctagatgaca   6900
aattcaacaa ctcacagctg actttctgcc attgccacta gggggggcc tttttatatg   6960
gccaagccaa gctctccacg tcggttgggc tgcacccaac aataaatggg tagggttgca   7020
ccaacaaagg gatgggatgg ggggtagaag atacgaggat aacggggctc aatggcacaa   7080
ataagaacga atactgccat taagactcgt gatccagcga ctgacaccat tgcatcatct   7140
```

-continued

```
aagggcctca aaactacctc ggaactgctg cgctgatctg gacaccacag aggttccgag   7200

cactttaggt tgcaccaaat gtcccaccag gtgcaggcag aaaacgctgg aacagcgtgt   7260

acagtttgtc ttaacaaaaa gtgagggcgc tgaggtcgag cagggtggtg tgacttgtta   7320

tagcctttag agctgcgaaa gcgcgtatgg atttggctca tcaggccaga ttgagggtct   7380

gtggacacat gtcatgttag tgtacttcaa tcgcccctg gatatagccc cgacaatagg    7440

ccgtggcctc attttttgc cttccgcaca tttccattgc tcgataccca caccttgctt    7500

ctcctgcact tgccaacctt aatactggtt tacattgacc aacatcttac aagcgggggg   7560

cttgtctagg gtatatataa acagtggctc tcccaatcgg ttgccagtct cttttttcct   7620

ttctttcccc acagattcga aatctaaact acacatcaca gaattccgag ccgtgagtat   7680

ccacgacaag atcagtgtcg agacgacgcg ttttgtgtaa tgacacaatc cgaaagtcgc   7740

tagcaacaca cactctctac acaaactaac ccagctctgg tac                     7783
```

<210> SEQ ID NO 35
<211> LENGTH: 8254
<212> TYPE: DNA
<213> ORGANISM: Artificial Sequence
<220> FEATURE:
<223> OTHER INFORMATION: plasmid pY175

<400> SEQUENCE: 35

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc ggcaacggtt tcacttgagt gcagtggcta    240

gtgctcttac tcgtacagtg tgcaatactg cgtatcatag tctttgatgt atatcgtatt    300

cattcatgtt agttgcgtac gagccggaag cataaagtgt aaagcctggg gtgcctaatg    360

agtgagctaa ctcacattaa ttgcgttgcg ctcactgccc gctttccagt cgggaaacct    420

gtcgtgccag ctgcattaat gaatcggcca acgcgcgggg agaggcggtt tgcgtattgg    480

gcgctcttcc gcttcctcgc tcactgactc gctgcgctcg gtcgttcggc tgcggcgagc    540

ggtatcagct cactcaaagg cggtaatacg gttatccaca gaatcagggg ataacgcagg    600

aaagaacatg tgagcaaaag gccagcaaaa ggccaggaac cgtaaaaagg ccgcgttgct    660

ggcgtttttc cataggctcc gcccccctga cgagcatcac aaaaatcgac gctcaagtca    720

gaggtggcga aacccgacag gactataaag ataccaggcg tttccccctg gaagctccct    780

cgtgcgctct cctgttccga ccctgccgct taccggatac ctgtccgcct ttctcccttc    840

gggaagcgtg gcgctttctc atagctcacg ctgtaggtat ctcagttcgg tgtaggtcgt    900

tcgctccaag ctgggctgtg tgcacgaacc ccccgttcag cccgaccgct gcgccttatc    960

cggtaactat cgtcttgagt ccaacccggt aagacacgac ttatcgccac tggcagcagc   1020

cactggtaac aggattagca gagcgaggta tgtaggcggt gctacagagt tcttgaagtg   1080

gtggcctaac tacggctaca ctagaaggac agtatttggt atctgcgctc tgctgaagcc   1140

agttaccttc ggaaaaagag ttggtagctc ttgatccggc aaacaaacca ccgctggtag   1200

cggtggtttt tttgtttgca agcagcagat tacgcgcaga aaaaaaggat ctcaagaaga   1260

tcctttgatc ttttctacgg ggtctgacgc tcagtggaac gaaaactcac gttaagggat   1320

tttggtcatg agattatcaa aaaggatctt cacctagatc cttttaaatt aaaaatgaag   1380

ttttaaatca atctaaagta tatatgagta aacttggtct gacagttacc aatgcttaat   1440
```

-continued

```
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aagggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggccccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat tttcgggcca ataatttaaa aaaatcgtgt tatataatat   3240
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
tgaacttatt tttattactt agtattatta gacaacttac ttgctttatg aaaaacactt   3480
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat cccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct   3780
```

-continued

```
cattgttcat acttctagtc atttcatccc acatattcct tggatttctc tccaatgaat   3840
gacattctat cttgcaaatt caacaattat aataagatat accaaagtag cggtatagtg   3900
gcaatcaaaa agcttctctg gtgtgcttct cgtatttatt tttattctaa tgatccatta   3960
aaggtatata tttatttctt gttatataat ccttttgttt attacatggg ctggatacat   4020
aaaggtattt tgatttaatt ttttgcttaa attcaatccc ccctcgttca gtgtcaactg   4080
taatggtagg aaattaccat acttttgaag aagcaaaaaa aatgaaagaa aaaaaaaatc   4140
gtatttccag gttagacgtt ccgcagaatc tagaatgcgg tatgcggtac attgttcttc   4200
gaacgtaaaa gttgcgctcc ctgagatatt gtacattttt gcttttacaa gtacaagtac   4260
atcgtacaac tatgtactac tgttgatgca tccacaacag tttgttttgt tttttttgt   4320
ttttttttt tctaatgatt cattaccgct atgtatacct acttgtactt gtagtaagcc   4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt tcttcgagcc   4560
tcatataagt ataagtagtt caacgtatta gcactgtacc cagcatctcc gtatcgagaa   4620
acacaacaac atgccccatt ggacagatca tgcggataca caggttgtgc agtatcatac   4680
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
caacagttcg gtactgctgt ccgagagcgt ctcccttgtc gtcaagaccc accccggggg   4980
tcagaataag ccagtcctca gagtcgccct taggtcggtt ctgggcaatg aagccaacca   5040
caaactcggg gtcggatcgg gcaagctcaa tggtctgctt ggagtactcg ccagtggcca   5100
gagagccctt gcaagacagc tcggccagca tgagcagacc tctggccagc ttctcgttgg   5160
gagaggggac taggaactcc ttgtactggg agttctcgta gtcagagacg tcctccttct   5220
tctgttcaga gacagtttcc tcggcaccag ctcgcaggcc agcaatgatt ccggttccgg   5280
gtacaccgtg ggcgttggtg atatcggacc actcggcgat tcggtgacac cggtactggt   5340
gcttgacagt gttgccaata tctgcgaact ttctgtcctc gaacaggaag aaaccgtgct   5400
taagagcaag ttccttgagg gggagcacag tgccggcgta ggtgaagtcg tcaatgatgt   5460
cgatatgggt tttgatcatg cacacataag gtccgacctt atcggcaagc tcaatgagct   5520
ccttggtggt ggtaacatcc agagaagcac acaggttggt tttcttggct gccacgagct   5580
tgagcactcg agcggcaaag gcggacttgt ggacgttagc tcgagcttcg taggagggca   5640
ttttggtggt gaagaggaga ctgaaataaa tttagtctgc agaacttttt atcggaacct   5700
tatctggggc agtgaagtat atgttatggt aatagttacg agttagttga acttatagat   5760
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
tgttgtcggc caaccgcgcc gaaaacgcag ctgtcagacc cacagcctcc aacgaagaat   5940
gtatcgtcaa agtgatccaa gcacactcat agttggagtc gtactccaaa ggcggcaatg   6000
acgagtcaga cagatactcg tcgacgttta aacagtgtac gcagatctac tatagaggaa   6060
catttaaatt gccccggaga agacggccag gccgcctaga tgacaaattc aacaactcac   6120
agctgacttt ctgccattgc cactaggggg gggccttttt atatggccaa gccaagctct   6180
```

-continued

```
ccacgtcggt tgggctgcac ccaacaataa atgggtaggg ttgcaccaac aaagggatgg   6240

gatggggggt agaagatacg aggataacgg ggctcaatgg cacaaataag aacgaatact   6300

gccattaaga ctcgtgatcc agcgactgac accattgcat catctaaggg cctcaaaact   6360

acctcggaac tgctgcgctg atctggacac cacagaggtt ccgagcactt taggttgcac   6420

caaatgtccc accaggtgca ggcagaaaac gctggaacag cgtgtacagt ttgtcttaac   6480

aaaaagtgag ggcgctgagg tcgagcaggg tggtgtgact tgttatagcc tttagagctg   6540

cgaaagcgcg tatggatttg gctcatcagg ccagattgag ggtctgtgga cacatgtcat   6600

gttagtgtac ttcaatcgcc ccctggatat agccccgaca ataggccgtg gcctcatttt   6660

tttgccttcc gcacatttcc attgctcgat acccacacct tgcttctcct gcacttgcca   6720

accttaatac tggtttacat tgaccaacat cttacaagcg gggggcttgt ctagggtata   6780

tataaacagt ggctctccca atcggttgcc agtctctttt ttcctttctt tccccacaga   6840

ttcgaaatct aaactacaca tcacagaatt ccgagccgtg agtatccacg acaagatcag   6900

tgtcgagacg acgcgttttg tgtaatgaca caatccgaaa gtcgctagca acacacactc   6960

tctacacaaa ctaacccagc tctggtacca tggtgaaaag gccagcactt ccgctgaccg   7020

ttgatggtgt cacctatgat gtgtctgcct ggttgaacca tcatccaggg ggtgctgaca   7080

tcattgagaa ctaccgcggt cgtgatgcca ctgatgtctt tatggttatg cactctgaaa   7140

atgctgtgag taaactaaga aggatgccta tcatggaacc atcatctcca ctgacgccta   7200

cgccaccgaa acccaactca gacgaaccgc aggaggattt ccgcaagctc cgagatgagc   7260

tcatcgcagc aggaatgttc gacgcatcac cgatgtggta cgcatataag acgctcacta   7320

cgctgggcct cggggtcctc gcggtgctat tgatgaccca gtggcactgg tacctcgtcg   7380

gggcaatcgt gttgggcatt cacttccaac aaatgggttg gttgtcgcac gatatctgcc   7440

accatcagct gttcaaggac cgatcgatca acaacgccat cggcttgctt ttcgggaacg   7500

tcttgcaagg gttctctgtg acctggtgga aggacaggca caatgcacac cactccgcca   7560

ccaacgtgca aggccacgac cccgacattg acaacctgcc gctgctggca tggtccaagg   7620

aggacgtgga gagggccggc ccgttctcac ggcggatgat caagtaccag caatactact   7680

tcttcttcat ctgtgccctc ctgaggttca tctggtgctt ccagagcatc cacacagcca   7740

agggcctgaa ggatcgcagc aaccagtact accgcaggca gtacgagaaa gagagcgtgg   7800

gcctggccct ccactggggc ctgaaggcgt tgttctacta cttttatatg ccaagcttct   7860

tgaccggact catggtgttt ttcgtgtccg agttgcttgg gggcttcggc atcgccatcg   7920

tggtgttcat gaaccactac cccctggaga agatccagga ctcggtgtgg gacggccacg   7980

gcttttgcgc cggccagatt cacgaaacga tgaacgtcca gcggggactc gtcacggact   8040

ggttcttcgg tgggctgaat taccaaatcg agcaccacct gtggccgacg ctgccccggc   8100

acaacctgac ggcggccagc atcaaagtgg agcagttgtg caagaagcac aacttgccgt   8160

atcgcagccc ccccaatgctg gagggggtgg gcatcctgat cagctacctg ggcacctttg   8220

cccgcatggt ggcaaaggcc gacaaggcgt aagc                               8254
```

<210> SEQ ID NO 36
<211> LENGTH: 8254
<212> TYPE: DNA
<213> ORGANISM: Artificial Sequence
<220> FEATURE:
<223> OTHER INFORMATION: plasmid pY176

-continued

<400> SEQUENCE: 36

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc ggcaacggtt tcacttgagt gcagtggcta    240
gtgctcttac tcgtacagtg tgcaatactg cgtatcatag tctttgatgt atatcgtatt    300
cattcatgtt agttgcgtac gagccggaag cataaagtgt aaagcctggg gtgcctaatg    360
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg gtcgttcggc tgcggcgagc    540
ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660
ggcgtttttc cataggctcc gcccccctga cgagcatcac aaaaatcgac gctcaagtca    720
gaggtggcga aacccgacag gactataaag ataccaggcg tttccccctg gaagctccct    780
cgtgcgctct cctgttccga ccctgccgct taccggatac ctgtccgcct ttctcccttc    840
gggaagcgtg gcgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc   1020
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaaggat ctcaagaaga   1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
```

-continued

```
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aagggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggccccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat tttcgggcca ataatttaaa aaaatcgtgt tatataatat   3240
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
tgaacttatt tttattactt agtattatta gacaacttac ttgctttatg aaaaacactt   3480
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat ccccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct   3780
cattgttcat acttctagtc atttcatccc acatattcct tggatttctc tccaatgaat   3840
gacattctat cttgcaaatt caacaattat aataagatat accaaagtag cggtatagtg   3900
gcaatcaaaa agcttctctg gtgtgcttct cgtatttatt tttattctaa tgatccatta   3960
aaggtatata tttatttctt gttatataat cctttttgttt attacatggg ctggatacat   4020
aaaggtattt tgatttaatt ttttgcttaa attcaatccc ccctcgttca gtgtcaactg   4080
taatggtagg aaattaccat acttttgaag aagcaaaaaa aatgaaagaa aaaaaaaatc   4140
gtatttccag gttagacgtt ccgcagaatc tagaatgcgg tatgcggtac attgttcttc   4200
gaacgtaaaa gttgcgctcc ctgagatatt gtacattttt gcttttacaa gtacaagtac   4260
atcgtacaac tatgtactac tgttgatgca tccacaacag tttgttttgt tttttttgt    4320
ttttttttt tctaatgatt cattaccgct atgtatacct acttgtactt gtagtaagcc   4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt tcttcgagcc   4560
tcatataagt ataagtagtt caacgtatta gcactgtacc cagcatctcc gtatcgagaa   4620
acacaacaac atgccccatt ggacagatca tgcggataca caggttgtgc agtatcatac   4680
```

-continued

```
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
caacagttcg gtactgctgt ccgagagcgt ctcccttgtc gtcaagaccc accccggggg   4980
tcagaataag ccagtcctca gagtcgccct taggtcggtt ctgggcaatg aagccaacca   5040
caaactcggg gtcggatcgg gcaagctcaa tggtctgctt ggagtactcg ccagtggcca   5100
gagagccctt gcaagacagc tcggccagca tgagcagacc tctggccagc ttctcgttgg   5160
gagaggggac taggaactcc ttgtactggg agttctcgta gtcagagacg tcctccttct   5220
tctgttcaga gacagtttcc tcggcaccag ctcgcaggcc agcaatgatt ccggttccgg   5280
gtacaccgtg ggcgttggtg atatcggacc actcggcgat tcggtgacac cggtactggt   5340
gcttgacagt gttgccaata tctgcgaact ttctgtcctc gaacaggaag aaaccgtgct   5400
taagagcaag ttccttgagg gggagcacag tgccggcgta ggtgaagtcg tcaatgatgt   5460
cgatatgggt tttgatcatg cacacataag gtccgacctt atcggcaagc tcaatgagct   5520
ccttggtggt ggtaacatcc agagaagcac acaggttggt tttcttggct gccacgagct   5580
tgagcactcg agcggcaaag gcggacttgt ggacgttagc tcgagcttcg taggagggca   5640
ttttggtggt gaagaggaga ctgaaataaa tttagtctgc agaacttttt atcggaacct   5700
tatctggggc agtgaagtat atgttatggt aatagttacg agttagttga acttatagat   5760
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
tgttgtcggc caaccgcgcc gaaaacgcag ctgtcagacc cacagcctcc aacgaagaat   5940
gtatcgtcaa agtgatccaa gcacactcat agttggagtc gtactccaaa ggcggcaatg   6000
acgagtcaga cagatactcg tcgacgttta aacagtgtac gcagatctac tatagaggaa   6060
catttaaatt gccccggaga agacggccag gccgcctaga tgacaaattc aacaactcac   6120
agctgacttt ctgccattgc cactaggggg gggccttttt atatggccaa gccaagctct   6180
ccacgtcggt tgggctgcac ccaacaataa atgggtaggg ttgcaccaac aaagggatgg   6240
gatgggggt agaagatacg aggataacgg ggctcaatgg cacaaataag aacgaatact   6300
gccattaaga ctcgtgatcc agcgactgac accattgcat catctaaggg cctcaaaact   6360
acctcggaac tgctgcgctg atctggacac cacagaggtt ccgagcactt taggttgcac   6420
caaatgtccc accaggtgca ggcagaaaac gctggaacag cgtgtacagt ttgtcttaac   6480
aaaaagtgag ggcgctgagg tcgagcaggg tggtgtgact tgttatagcc tttagagctg   6540
cgaaagcgcg tatggatttg gctcatcagg ccagattgag ggtctgtgga cacatgtcat   6600
gttagtgtac ttcaatcgcc ccctggatat agccccgaca ataggccgtg gcctcatttt   6660
tttgccttcc gcacatttcc attgctcgat acccacacct tgcttctcct gcacttgcca   6720
accttaatac tggtttacat tgaccaacat cttacaagcg gggggcttgt ctagggtata   6780
tataaacagt ggctctccca atcggttgcc agtctctttt ttcctttctt tccccacaga   6840
ttcgaaatct aaactacaca tcacagaatt ccgagccgtg agtatccacg acaagatcag   6900
tgtcgagacg acgcgttttg tgtaatgaca caatccgaaa gtcgctagca acacacactc   6960
tctacacaaa ctaacccagc tctggtacca tggtgaaaag gccagcactt ccgctgaccg   7020
ttgatggtgt cacctatgat gtgtctgcct ggttgaacca tcatccaggg ggtgctgaca   7080
```

-continued

```
tcattgagaa ctaccgcggt cgtgatgcca ctgatgtctt tatggttatg cactctgaaa   7140
atgctgtgag taaactaaga aggatgccta tcatggaacc atcatctcca ctgacgccta   7200
cgccaccgaa acccaactca gacgaaccgc aggaggattt ccgcaagctc cgagatgagc   7260
tcatcgcagc aggaatgttc gacgcatcac cgatgtggta cgcatataag acgctcagta   7320
cgctgggcct cggggtcctc gcggtgctat tgatgaccca gtggcactgg tacctcgtcg   7380
gggcaatcgt gttgggcatt cacttccaac aaatgggttg gttgtcgcac gatatctgcc   7440
accatcagct gttcaaggac cgatcgatca acaacgccat cggcttgctt ttcgggaacg   7500
tcttgcaagg gttctctgtg acctggtgga aggacaggca caatgcacac cactccgcca   7560
ccaacgtgca aggccacgac cccgacattg acaacctgcc gctgctggca tggtccaagg   7620
aggacgtgga gagggccggc ccgttctcac ggcggattat caagtaccag caatactact   7680
tcttcttcat ctgtgccctc ctgaggttca tctggtgctt ccagagcatc cacacagcca   7740
cgggcctgaa ggatcgcagc aaccagtact accgcaggca gtacgagaaa gagagcgtgg   7800
gcctggccct ccactggggc ctgaaggcgt tgttctacta cttttatatg ccaagcttct   7860
tgaccggact catggtgttt ttcgtgtccg agttgcttgg gggcttcggc atcgccatcg   7920
tggtgttcat gaaccactac cccctggaga agatccagga ctcggtgtgg gacggccacg   7980
gcttttgcgc cggccagatt cacgaaacga tgaacgtcca gcggggactc gtcacggact   8040
ggttcttcgg tgggctgaat taccaaatcg agcaccacct gtggccgacg ctgccccggc   8100
acaacctgac ggcggccagc atcaaagtgg agcagttgtg caagaagcac aacttgccgt   8160
atcgcagccc cccaatgctg gagggggtgg gcatcctgat cagctacctg ggcacctttg   8220
cccgcatggt ggcaaaggcc gacaaggcgt aagc                               8254
```

<210> SEQ ID NO 37
<211> LENGTH: 8254
<212> TYPE: DNA
<213> ORGANISM: Artificial Sequence
<220> FEATURE:
<223> OTHER INFORMATION: plasmid pY177

<400> SEQUENCE: 37

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc ggcaacggtt tcacttgagt gcagtggcta    240
gtgctcttac tcgtacagtg tgcaatactg cgtatcatag tctttgatgt atatcgtatt    300
cattcatgtt agttgcgtac gagccggaag cataaagtgt aaagcctggg gtgcctaatg    360
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg gtcgttcggc tgcggcgagc    540
ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660
ggcgtttttc cataggctcc gcccccctga cgagcatcac aaaaatcgac gctcaagtca    720
gaggtggcga aacccgacag gactataaag ataccaggcg tttccccctg gaagctccct    780
cgtgcgctct cctgttccga ccctgccgct taccggatac ctgtccgcct ttctcccttc    840
```

-continued

```
gggaagcgtg gcgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc   1020
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaaggat ctcaagaaga   1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aagggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggcccccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat tttcgggcca ataatttaaa aaaatcgtgt tatataatat   3240
```

-continued

```
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
tgaacttatt tttattactt agtattatta gacaacttac ttgctttatg aaaaacactt   3480
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat cccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct   3780
cattgttcat acttctagtc atttcatccc acatattcct tggatttctc tccaatgaat   3840
gacattctat cttgcaaatt caacaattat aataagatat accaaagtag cggtatagtg   3900
gcaatcaaaa agcttctctg gtgtgcttct cgtatttatt tttattctaa tgatccatta   3960
aaggtatata tttatttctt gttatataat ccttttgttt attacatggg ctggatacat   4020
aaaggtattt tgatttaatt ttttgcttaa attcaatccc ccctcgttca gtgtcaactg   4080
taatggtagg aaattaccat acttttgaag aagcaaaaaa aatgaaagaa aaaaaaaatc   4140
gtatttccag gttagacgtt ccgcagaatc tagaatgcgg tatgcggtac attgttcttc   4200
gaacgtaaaa gttgcgctcc ctgagatatt gtacattttt gcttttacaa gtacaagtac   4260
atcgtacaac tatgtactac tgttgatgca tccacaacag tttgttttgt tttttttgt   4320
tttttttttt tctaatgatt cattaccgct atgtatacct acttgtactt gtagtaagcc   4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt tcttcgagcc   4560
tcatataagt ataagtagtt caacgtatta gcactgtacc cagcatctcc gtatcgagaa   4620
acacaacaac atgccccatt ggacagatca tgcggataca caggttgtgc agtatcatac   4680
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
caacagttcg gtactgctgt ccgagagcgt ctcccttgtc gtcaagaccc accccggggg   4980
tcagaataag ccagtcctca gagtcgccct taggtcggtt ctgggcaatg aagccaacca   5040
caaactcggg gtcggatcgg gcaagctcaa tggtctgctt ggagtactcg ccagtggcca   5100
gagagccctt gcaagacagc tcggccagca tgagcagacc tctggccagc ttctcgttgg   5160
gagaggggac taggaactcc ttgtactggg agttctcgta gtcagagacg tcctccttct   5220
tctgttcaga gacagtttcc tcggcaccag ctcgcaggcc agcaatgatt ccggttccgg   5280
gtacaccgtg ggcgttggtg atatcggacc actcggcgat tcggtgacac cggtactggt   5340
gcttgacagt gttgccaata tctgcgaact ttctgtcctc gaacaggaag aaaccgtgct   5400
taagagcaag ttccttgagg gggagcacag tgccggcgta ggtgaagtcg tcaatgatgt   5460
cgatatgggt tttgatcatg cacacataag gtccgacctt atcggcaagc tcaatgagct   5520
ccttggtggt ggtaacatcc agagaagcac acaggttggt tttcttggct gccacgagct   5580
```

-continued

```
tgagcactcg agcggcaaag gcggacttgt ggacgttagc tcgagcttcg taggagggca   5640
ttttggtggt gaagaggaga ctgaaataaa tttagtctgc agaacttttt atcggaacct   5700
tatctggggc agtgaagtat atgttatggt aatagttacg agttagttga acttatagat   5760
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
tgttgtcggc caaccgcgcc gaaaacgcag ctgtcagacc cacagcctcc aacgaagaat   5940
gtatcgtcaa agtgatccaa gcacactcat agttggagtc gtactccaaa ggcggcaatg   6000
acgagtcaga cagatactcg tcgacgttta aacagtgtac gcagatctac tatagaggaa   6060
catttaaatt gccccggaga agacggccag gccgcctaga tgacaaattc aacaactcac   6120
agctgacttt ctgccattgc cactaggggg gggccttttt atatggccaa gccaagctct   6180
ccacgtcggt tgggctgcac ccaacaataa atgggtaggg ttgcaccaac aaagggatgg   6240
gatgggggt agaagatacg aggataacgg ggctcaatgg cacaaataag aacgaatact   6300
gccattaaga ctcgtgatcc agcgactgac accattgcat catctaaggg cctcaaaact   6360
acctcggaac tgctgcgctg atctggacac cacagaggtt ccgagcactt taggttgcac   6420
caaatgtccc accaggtgca ggcagaaaac gctggaacag cgtgtacagt ttgtcttaac   6480
aaaaagtgag ggcgctgagg tcgagcaggg tggtgtgact tgttatagcc tttagagctg   6540
cgaaagcgcg tatggatttg gctcatcagg ccagattgag ggtctgtgga cacatgtcat   6600
gttagtgtac ttcaatcgcc ccctggatat agccccgaca ataggccgtg gcctcatttt   6660
tttgccttcc gcacatttcc attgctcgat acccacacct tgcttctcct gcacttgcca   6720
accttaatac tggtttacat tgaccaacat cttacaagcg gggggcttgt ctagggtata   6780
tataaacagt ggctctccca atcggttgcc agtctctttt ttcctttctt tccccacaga   6840
ttcgaaatct aaactacaca tcacagaatt ccgagccgtg agtatccacg acaagatcag   6900
tgtcgagacg acgcgttttg tgtaatgaca caatccgaaa gtcgctagca acacacactc   6960
tctacacaaa ctaacccagc tctggtacca tggtgaaaag gccagcactt ccgctgaccg   7020
ttgatggtgt cacctatgat gtgtctgcct ggttgaacca tcatccaggg ggtgctgaca   7080
tcattgagaa ctaccgcggt cgtgatgcca ctgatgtctt tatggttatg cactctgaaa   7140
atgctgtgag taaactaaga aggatgccta tcatggaacc atcatctcca ctgacgccta   7200
cgccaccgaa acccaactca gacgaaccgc aggaggattt ccgcaagctc cgagatgagc   7260
tcatcgcagc aggaatgttc gacgcatcac cgatgtggta cgcatataag acgctcagta   7320
cgctgggcct cggggtcctc gcggtgctat tgatgaccca gtggcactgg tacctcgtcg   7380
gggcaatcgt gttgggcatt cacttccaac aaatgggttg gttgtcgcac gatatctgcc   7440
accatcagct gttcaaggac cgatcgatca acaacgccat cggcttgctt ttcgggaacg   7500
tcttgcaagg gttctctgtg acctggtgga aggacaggca caatgcacac cactccgcca   7560
ccaacgtgca aggccacgac cccgacattg acaacctgcc gctgctggca tggtccaagg   7620
aggacgtgga gagggccggc ccgttctcac ggcggatgat caagtaccag caatactact   7680
tcttcttcat ctgtgccctc ctgaggttca tctggtgctt ccagagcatc cacacagcca   7740
cgggcctgaa ggatcgcagc aaccagtact accgcaggca gtacgagaaa gagagcgtgg   7800
gcctggccct ccactggggc ctgaaggcgt tgttctacta cttttatatg ccaagcttct   7860
tgaccggact catggtgttt ttcgtgtccg agttgcttgg gggcttcggc atcgccatcg   7920
tggtgttcat gaaccactac cccctggaga agatccagga ctcggtgtgg gacggccacg   7980
```

-continued gcttttgcgc cggccagatt cacgaaacga tgaacgtcca gcggggactc gtcacggact 8040
ggttcttcgg tgggctgaat taccaaatcg agcaccacct gtggccgacg ctgccccggc 8100
acaacctgac ggcggccagc atcaaagtgg agcagttgtg caagaagcac aacttgccgt 8160
atcgcagccc cccaatgctg gagggggtgg gcatcctgat cagctacctg ggcacctttg 8220
cccgcatggt ggcaaaggcc gacaaggcgt aagc 8254

<210> SEQ ID NO 38
<211> LENGTH: 8254
<212> TYPE: DNA
<213> ORGANISM: Artificial Sequence
<220> FEATURE:
<223> OTHER INFORMATION: plasmid pY178

<400> SEQUENCE: 38
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc ggcaacggtt tcacttgagt gcagtggcta 240
gtgctcttac tcgtacagtg tgcaatactg cgtatcatag tctttgatgt atatcgtatt 300
cattcatgtt agttgcgtac gagccggaag cataaagtgt aaagcctggg gtgcctaatg 360
agtgagctaa ctcacattaa ttgcgttgcg ctcactgccc gctttccagt cgggaaacct 420
gtcgtgccag ctgcattaat gaatcggcca acgcgcgggg agaggcggtt tgcgtattgg 480
gcgctcttcc gcttcctcgc tcactgactc gctgcgctcg gtcgttcggc tgcggcgagc 540
ggtatcagct cactcaaagg cggtaatacg gttatccaca gaatcagggg ataacgcagg 600
aaagaacatg tgagcaaaag gccagcaaaa ggccaggaac cgtaaaaagg ccgcgttgct 660
ggcgtttttc cataggctcc gcccccctga cgagcatcac aaaaatcgac gctcaagtca 720
gaggtggcga aacccgacag gactataaag ataccaggcg tttccccctg gaagctccct 780
cgtgcgctct cctgttccga ccctgccgct taccggatac ctgtccgcct ttctcccttc 840
gggaagcgtg gcgctttctc atagctcacg ctgtaggtat ctcagttcgg tgtaggtcgt 900
tcgctccaag ctgggctgtg tgcacgaacc ccccgttcag cccgaccgct gcgccttatc 960
cggtaactat cgtcttgagt ccaacccggt aagacacgac ttatcgccac tggcagcagc 1020
cactggtaac aggattagca gagcgaggta tgtaggcggt gctacagagt tcttgaagtg 1080
gtggcctaac tacggctaca ctagaaggac agtatttggt atctgcgctc tgctgaagcc 1140
agttaccttc ggaaaaagag ttggtagctc ttgatccggc aaacaaacca ccgctggtag 1200
cggtggtttt tttgtttgca agcagcagat tacgcgcaga aaaaaaggat ctcaagaaga 1260
tcctttgatc ttttctacgg ggtctgacgc tcagtggaac gaaaactcac gttaagggat 1320
tttggtcatg agattatcaa aaaggatctt cacctagatc cttttaaatt aaaaatgaag 1380
ttttaaatca atctaaagta tatatgagta aacttggtct gacagttacc aatgcttaat 1440
cagtgaggca cctatctcag cgatctgtct atttcgttca tccatagttg cctgactccc 1500
cgtcgtgtag ataactacga tacgggaggg cttaccatct ggccccagtg ctgcaatgat 1560
accgcgagac ccacgctcac cggctccaga tttatcagca ataaaccagc cagccggaag 1620
ggccgagcgc agaagtggtc ctgcaacttt atccgcctcc atccagtcta ttaattgttg 1680
ccgggaagct agagtaagta gttcgccagt taatagtttg cgcaacgttg ttgccattgc 1740

-continued

```
tacaggcatc gtggtgtcac gctcgtcgtt tggtatggct tcattcagct ccggttccca   1800
acgatcaagg cgagttacat gatcccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc gggggctccc   2580
tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
ctattctttt gatttataag ggattttgcc gatttcggcc tattggttaa aaaatgagct   2820
gatttaacaa aaatttaacg cgaattttaa caaaatatta acgcttacaa tttccattcg   2880
ccattcaggc tgcgcaactg ttgggaaggg cgatcggtgc gggcctcttc gctattacgc   2940
cagctggcga aagggggatg tgctgcaagg cgattaagtt gggtaacgcc agggttttcc   3000
cagtcacgac gttgtaaaac gacggccagt gaattgtaat acgactcact atagggcgaa   3060
ttgggtaccg ggccccccct cgaggtcgat ggtgtcgata agcttgatat cgaattcatg   3120
tcacacaaac cgatcttcgc ctcaaggaaa cctaattcta catccgagag actgccgaga   3180
tccagtctac actgattaat tttcgggcca ataatttaaa aaaatcgtgt tatataatat   3240
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacagactc catctaccgc ctccaaatga tgttctcaaa atatattgta   3420
tgaacttatt tttattactt agtattatta gacaacttac ttgctttatg aaaaacactt   3480
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat ccccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct   3780
cattgttcat acttctagtc atttcatccc acatattcct tggatttctc tccaatgaat   3840
gacattctat cttgcaaatt caacaattat aataagatat accaaagtag cggtatagtg   3900
gcaatcaaaa agcttctctg gtgtgcttct cgtatttatt tttattctaa tgatccatta   3960
aaggtatata tttatttctt gttatataat ccttttgttt attacatggg ctggatacat   4020
aaaggtattt tgatttaatt ttttgcttaa attcaatccc ccctcgttca gtgtcaactg   4080
taatggtagg aaattaccat acttttgaag aagcaaaaaa aatgaaagaa aaaaaaaatc   4140
```

-continued

```
gtatttccag gttagacgtt ccgcagaatc tagaatgcgg tatgcggtac attgttcttc   4200
gaacgtaaaa gttgcgctcc ctgagatatt gtacattttt gcttttacaa gtacaagtac   4260
atcgtacaac tatgtactac tgttgatgca tccacaacag tttgttttgt tttttttgt   4320
ttttttttt tctaatgatt cattaccgct atgtatacct acttgtactt gtagtaagcc   4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt tcttcgagcc   4560
tcatataagt ataagtagtt caacgtatta gcactgtacc cagcatctcc gtatcgagaa   4620
acacaacaac atgccccatt ggacagatca tgcggataca caggttgtgc agtatcatac   4680
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
caacagttcg gtactgctgt ccgagagcgt ctcccttgtc gtcaagaccc accccggggg   4980
tcagaataag ccagtcctca gagtcgccct taggtcggtt ctgggcaatg aagccaacca   5040
caaactcggg gtcggatcgg gcaagctcaa tggtctgctt ggagtactcg ccagtggcca   5100
gagagccctt gcaagacagc tcggccagca tgagcagacc tctggccagc ttctcgttgg   5160
gagaggggac taggaactcc ttgtactggg agttctcgta gtcagagacg tcctccttct   5220
tctgttcaga gacagtttcc tcggcaccag ctcgcaggcc agcaatgatt ccggttccgg   5280
gtacaccgtg ggcgttggtg atatcggacc actcggcgat tcggtgacac cggtactggt   5340
gcttgacagt gttgccaata tctgcgaact ttctgtcctc gaacaggaag aaaccgtgct   5400
taagagcaag ttccttgagg gggagcacag tgccggcgta ggtgaagtcg tcaatgatgt   5460
cgatatgggt tttgatcatg cacacataag gtccgacctt atcggcaagc tcaatgagct   5520
ccttggtggt ggtaacatcc agagaagcac acaggttggt tttcttggct gccacgagct   5580
tgagcactcg agcggcaaag gcggacttgt ggacgttagc tcgagcttcg taggagggca   5640
ttttggtggt gaagaggaga ctgaaataaa tttagtctgc agaacttttt atcggaacct   5700
tatctggggc agtgaagtat atgttatggt aatagttacg agttagttga acttatagat   5760
agactggact atacggctat cggtccaaat tagaaagaac gtcaatggct ctctgggcgt   5820
cgcctttgcc gacaaaaatg tgatcatgat gaaagccagc aatgacgttg cagctgatat   5880
tgttgtcggc caaccgcgcc gaaaacgcag ctgtcagacc cacagcctcc aacgaagaat   5940
gtatcgtcaa agtgatccaa gcacactcat agttggagtc gtactccaaa ggcggcaatg   6000
acgagtcaga cagatactcg tcgacgttta aacagtgtac gcagatctac tatagaggaa   6060
catttaaatt gccccggaga agacggccag gccgcctaga tgacaaattc aacaactcac   6120
agctgacttt ctgccattgc cactaggggg gggcctttt atatggccaa gccaagctct   6180
ccacgtcggt tgggctgcac ccaacaataa atgggtaggg ttgcaccaac aaagggatgg   6240
gatgggggt agaagatacg aggataacgg ggctcaatgg cacaaataag aacgaatact   6300
gccattaaga ctcgtgatcc agcgactgac accattgcat catctaaggg cctcaaaact   6360
acctcggaac tgctgcgctg atctggacac cacagaggtt ccgagcactt taggttgcac   6420
caaatgtccc accaggtgca ggcagaaaac gctggaacag cgtgtacagt ttgtcttaac   6480
```

-continued

```
aaaaagtgag ggcgctgagg tcgagcaggg tggtgtgact tgttatagcc tttagagctg   6540

cgaaagcgcg tatggatttg gctcatcagg ccagattgag ggtctgtgga cacatgtcat   6600

gttagtgtac ttcaatcgcc ccctggatat agccccgaca ataggccgtg gcctcatttt   6660

tttgccttcc gcacatttcc attgctcgat acccacacct tgcttctcct gcacttgcca   6720

accttaatac tggtttacat tgaccaacat cttacaagcg gggggcttgt ctagggtata   6780

tataaacagt ggctctccca atcggttgcc agtctctttt ttcctttctt tccccacaga   6840

ttcgaaatct aaactacaca tcacagaatt ccgagccgtg agtatccacg acaagatcag   6900

tgtcgagacg acgcgttttg tgtaatgaca caatccgaaa gtcgctagca acacacactc   6960

tctacacaaa ctaacccagc tctggtacca tggtgaaaag gccagcactt ccgctgaccg   7020

ttgatggtgt cacctatgat gtgtctgcct ggttgaacca tcatccaggg ggtgctgaca   7080

tcattgagaa ctaccgcggt cgtgatgcca ctgatgtctt tatggttatg cactctgaaa   7140

atgctgtgag taaactaaga aggatgccta tcatggaacc atcatctcca ctgacgccta   7200

cgccaccgaa acccaactca gacgaaccgc aggaggattt ccgcaagctc cgagatgagc   7260

tcatcgcagc aggaatgttc gacgcatcac cgatgtggta cgcatataag acgctcagta   7320

cgctgggcct cggggtcctc gcggtgctat tgatgaccca gtggcactgg tacctcgtcg   7380

gggcaatcgt gttgggcatt cacttccaac aaatgggttg gttgtcgcac gatatctgcc   7440

accatcagct gttcaaggac cgatcgatca acaacgccat cggcttgctt ttcgggaacg   7500

tcttgcaagg gttctctgtg acctggtgga aggacaggca caatgcacac cactccgcca   7560

ccaacgtgca aggccacgac cccgacattg acaacctgcc gctgctggca tggtccaagg   7620

aggacgtgga gagggccggc ccgttctcac ggcggatgat caagtaccag caatactact   7680

tcttcttcat ctgtgccctc ctgaggttca tctggtgctt ccagagcatc cacacagcca   7740

agggcctgaa ggatcgcagc aaccagtact accgcaggca gtacgagaaa gagagcgtgg   7800

gcctggccct ccactggggc ctgaaggcgt tgttctacta cttttatatg ccaagcttct   7860

tgaccggact catggtgttt ttcgtgtccg agttgcttgg gggcttcggc atcgccatcg   7920

tggtgttcat gaaccactac cccctggaga agatccagga ctcggtgtgg gacggccacg   7980

gcttttgcgc cggccagatt cacgaaacga tgaacgtcca gcggggactc gtcacggact   8040

ggttcttcgg tgggctgaat taccaaatcg agcaccacct gtggccgacg ctgccccggc   8100

acaacctgac ggcggccagc atcaaagtgg agcagttgtg caagaagcac aacttgccgt   8160

atcgcagccc ccccaatgctg gagggggtgg gcatcctgat cagctacctg ggcacctttg   8220

cccgcatggt ggcaaaggcc gacaaggcgt aagc                                8254


<210> SEQ ID NO 39
<211> LENGTH: 1260
<212> TYPE: DNA
<213> ORGANISM: Euglena anabaena
<220> FEATURE:
<221> NAME/KEY: CDS
<222> LOCATION: (1)..(1260)
<223> OTHER INFORMATION: delta-8 desaturase gene (codon-optimized for
      Yarrowia lipolytica and designated "EaD8S")

<400> SEQUENCE: 39

atg gtc aag cga ccc gct ctg cct ctc acc gtg gac ggt gtc acc tac       48
Met Val Lys Arg Pro Ala Leu Pro Leu Thr Val Asp Gly Val Thr Tyr
1               5                   10                  15

gac gtt tct gcc tgg ctc aac cac cat ccc gga ggt gcc gac att atc       96
Asp Val Ser Ala Trp Leu Asn His His Pro Gly Gly Ala Asp Ile Ile
```

-continued

```
            20                  25                  30

gag aac tac cga ggt cgg gat gct acc gac gtc ttc atg gtt atg cac      144
Glu Asn Tyr Arg Gly Arg Asp Ala Thr Asp Val Phe Met Val Met His
        35                  40                  45

tcc gag aac gcc gtg tcc aaa ctc aga cga atg ccc atc atg gaa cct      192
Ser Glu Asn Ala Val Ser Lys Leu Arg Arg Met Pro Ile Met Glu Pro
    50                  55                  60

tcc tct ccc ctg act cca aca cct ccc aag cca aac tcc gac gaa cct      240
Ser Ser Pro Leu Thr Pro Thr Pro Pro Lys Pro Asn Ser Asp Glu Pro
65                  70                  75                  80

cag gag gat ttc cga aag ctg cga gac gag ctc att gct gca ggc atg      288
Gln Glu Asp Phe Arg Lys Leu Arg Asp Glu Leu Ile Ala Ala Gly Met
                85                  90                  95

ttc gat gcc tct ccc atg tgg tac gct tac aag acc ctg tcg act ctc      336
Phe Asp Ala Ser Pro Met Trp Tyr Ala Tyr Lys Thr Leu Ser Thr Leu
            100                 105                 110

gga ctg ggt gtc ctt gcc gtg ctg ttg atg acc cag tgg cac tgg tac      384
Gly Leu Gly Val Leu Ala Val Leu Leu Met Thr Gln Trp His Trp Tyr
        115                 120                 125

ctg gtt ggt gct atc gtc ctc ggc att cac ttt caa cag atg gga tgg      432
Leu Val Gly Ala Ile Val Leu Gly Ile His Phe Gln Gln Met Gly Trp
    130                 135                 140

ctc tcg cac gac att tgc cat cac cag ctg ttc aag gac cga tcc atc      480
Leu Ser His Asp Ile Cys His His Gln Leu Phe Lys Asp Arg Ser Ile
145                 150                 155                 160

aac aat gcc att ggc ctg ctc ttc gga aac gtg ctt cag ggc ttt tct      528
Asn Asn Ala Ile Gly Leu Leu Phe Gly Asn Val Leu Gln Gly Phe Ser
                165                 170                 175

gtc act tgg tgg aag gac cga cac aac gct cat cac tcc gcc acc aac      576
Val Thr Trp Trp Lys Asp Arg His Asn Ala His His Ser Ala Thr Asn
            180                 185                 190

gtg cag ggt cac gat ccc gac atc gac aac ctg cct ctc ctg gcg tgg      624
Val Gln Gly His Asp Pro Asp Ile Asp Asn Leu Pro Leu Leu Ala Trp
        195                 200                 205

tcc aag gag gac gtc gag cga gct ggc ccg ttt tct cga cgg atg atc      672
Ser Lys Glu Asp Val Glu Arg Ala Gly Pro Phe Ser Arg Arg Met Ile
    210                 215                 220

aag tac caa cag tat tac ttc ttt ttc atc tgt gcc ctt ctg cga ttc      720
Lys Tyr Gln Gln Tyr Tyr Phe Phe Phe Ile Cys Ala Leu Leu Arg Phe
225                 230                 235                 240

atc tgg tgc ttt cag tcc att cat act gcc acg ggt ctc aag gat cga      768
Ile Trp Cys Phe Gln Ser Ile His Thr Ala Thr Gly Leu Lys Asp Arg
                245                 250                 255

agc aat cag tac tat cga aga cag tac gag aag gag tcc gtc ggt ctg      816
Ser Asn Gln Tyr Tyr Arg Arg Gln Tyr Glu Lys Glu Ser Val Gly Leu
            260                 265                 270

gca ctc cac tgg ggt ctc aag gcc ttg ttc tac tat ttc tac atg ccc      864
Ala Leu His Trp Gly Leu Lys Ala Leu Phe Tyr Tyr Phe Tyr Met Pro
        275                 280                 285

tcg ttt ctc acc gga ctc atg gtg ttc ttt gtc tcc gag ctg ctt ggt      912
Ser Phe Leu Thr Gly Leu Met Val Phe Phe Val Ser Glu Leu Leu Gly
    290                 295                 300

ggc ttc gga att gcc atc gtt gtc ttc atg aac cac tac cct ctg gag      960
Gly Phe Gly Ile Ala Ile Val Val Phe Met Asn His Tyr Pro Leu Glu
305                 310                 315                 320

aag att cag gac tcc gtg tgg gat ggt cat ggc ttc tgt gct gga cag     1008
Lys Ile Gln Asp Ser Val Trp Asp Gly His Gly Phe Cys Ala Gly Gln
                325                 330                 335

att cac gag acc atg aac gtt cag cga ggc ctc gtc aca gac tgg ttt     1056
```

-continued

```
Ile His Glu Thr Met Asn Val Gln Arg Gly Leu Val Thr Asp Trp Phe
            340                 345                 350

ttc ggt ggc ctc aac tac cag atc gaa cat cac ctg tgg cct act ctt      1104
Phe Gly Gly Leu Asn Tyr Gln Ile Glu His His Leu Trp Pro Thr Leu
        355                 360                 365

ccc aga cac aac ctc acc gct gcc tcc atc aaa gtg gag cag ctg tgc      1152
Pro Arg His Asn Leu Thr Ala Ala Ser Ile Lys Val Glu Gln Leu Cys
    370                 375                 380

aag aag cac aac ctg ccc tac cga tct cct ccc atg ctc gaa ggt gtc      1200
Lys Lys His Asn Leu Pro Tyr Arg Ser Pro Pro Met Leu Glu Gly Val
385                 390                 395                 400

ggc att ctt atc tcc tac ctg ggc acc ttc gct cga atg gtt gcc aag      1248
Gly Ile Leu Ile Ser Tyr Leu Gly Thr Phe Ala Arg Met Val Ala Lys
                405                 410                 415

gca gac aag gcc                                                      1260
Ala Asp Lys Ala
            420


<210> SEQ ID NO 40
<211> LENGTH: 420
<212> TYPE: PRT
<213> ORGANISM: Euglena anabaena

<400> SEQUENCE: 40

Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Phe Ile Cys Ala Leu Leu Arg Phe
225                 230                 235                 240

Ile Trp Cys Phe Gln Ser Ile His Thr Ala Thr Gly Leu Lys Asp Arg
                245                 250                 255
```

-continued

```
Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420


<210> SEQ ID NO 41
<211> LENGTH: 3983
<212> TYPE: DNA
<213> ORGANISM: Artificial Sequence
<220> FEATURE:
<223> OTHER INFORMATION: plasmid pEaD8S

<400> SEQUENCE: 41

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accatatgcg gtgtgaaata ccgcacagat gcgtaaggag aaaataccgc atcaggcgcc     240

attcgccatt caggctgcgc aactgttggg aagggcgatc ggtgcgggcc tcttcgctat     300

tacgccagct ggcgaaaggg ggatgtgctg caaggcgatt aagttgggta acgccagggt     360

tttcccagtc acgacgttgt aaaacgacgg ccagtgaatt cgagctcggt acctcgcgaa     420

tgcatctaga tccatggtca agcgacccgc tctgcctctc accgtggacg gtgtcaccta     480

cgacgtttct gcctggctca accaccatcc cggaggtgcc gacattatcg agaactaccg     540

aggtcgggat gctaccgacg tcttcatggt tatgcactcc gagaacgccg tgtccaaact     600

cagacgaatg cccatcatgg aaccttcctc tcccctgact ccaacacctc ccaagccaaa     660

ctccgacgaa cctcaggagg atttccgaaa gctgcgagac gagctcattg ctgcaggcat     720

gttcgatgcc tctcccatgt ggtacgctta caagaccctg tcgactctcg gactgggtgt     780

ccttgccgtg ctgttgatga cccagtggca ctggtacctg gttggtgcta tcgtcctcgg     840

cattcacttt caacagatgg gatggctctc gcacgacatt tgccatcacc agctgttcaa     900

ggaccgatcc atcaacaatg ccattggcct gctcttcgga aacgtgcttc agggcttttc     960

tgtcacttgg tggaaggacc gacacaacgc tcatcactcc gccaccaacg tgcagggtca    1020

cgatcccgac atcgacaacc tgcctctcct ggcgtggtcc aaggaggacg tcgagcgagc    1080
```

-continued

```
tggcccgttt tctcgacgga tgatcaagta ccaacagtat tacttctttt tcatctgtgc   1140
ccttctgcga ttcatctggt gctttcagtc cattcatact gccacgggtc tcaaggatcg   1200
aagcaatcag tactatcgaa gacagtacga gaaggagtcc gtcggtctgg cactccactg   1260
gggtctcaag gccttgttct actatttcta catgccctcg tttctcaccg gactcatggt   1320
gttctttgtc tccgagctgc ttggtggctt cggaattgcc atcgttgtct tcatgaacca   1380
ctaccctctg gagaagattc aggactccgt gtgggatggt catggcttct gtgctggaca   1440
gattcacgag accatgaacg ttcagcgagg cctcgtcaca gactggtttt tcggtggcct   1500
caactaccag atcgaacatc acctgtggcc tactcttccc agacacaacc tcaccgctgc   1560
ctccatcaaa gtggagcagc tgtgcaagaa gcacaacctg ccctaccgat ctcctcccat   1620
gctcgaaggt gtcggcattc ttatctccta cctgggcacc ttcgctcgaa tggttgccaa   1680
ggcagacaag gcctaagcgg ccgcatcgga tcccgggccc gtcgactgca gaggcctgca   1740
tgcaagcttg gcgtaatcat ggtcatagct gtttcctgtg tgaaattgtt atccgctcac   1800
aattccacac aacatacgag ccggaagcat aaagtgtaaa gcctggggtg cctaatgagt   1860
gagctaactc acattaattg cgttgcgctc actgcccgct ttccagtcgg gaaacctgtc   1920
gtgccagctg cattaatgaa tcggccaacg cgcggggaga ggcggtttgc gtattgggcg   1980
ctcttccgct tcctcgctca ctgactcgct gcgctcggtc gttcggctgc ggcgagcggt   2040
atcagctcac tcaaaggcgg taatacggtt atccacagaa tcaggggata acgcaggaaa   2100
gaacatgtga gcaaaaggcc agcaaaaggc caggaaccgt aaaaaggccg cgttgctggc   2160
gtttttccat aggctccgcc cccctgacga gcatcacaaa aatcgacgct caagtcagag   2220
gtggcgaaac ccgacaggac tataaagata ccaggcgttt ccccctggaa gctccctcgt   2280
gcgctctcct gttccgaccc tgccgcttac cggatacctg tccgcctttc tcccttcggg   2340
aagcgtggcg ctttctcata gctcacgctg taggtatctc agttcggtgt aggtcgttcg   2400
ctccaagctg ggctgtgtgc acgaaccccc cgttcagccc gaccgctgcg ccttatccgg   2460
taactatcgt cttgagtcca acccggtaag acacgactta tcgccactgg cagcagccac   2520
tggtaacagg attagcagag cgaggtatgt aggcggtgct acagagttct tgaagtggtg   2580
gcctaactac ggctacacta gaagaacagt atttggtatc tgcgctctgc tgaagccagt   2640
taccttcgga aaaagagttg gtagctcttg atccggcaaa caaaccaccg ctggtagcgg   2700
tggttttttt gtttgcaagc agcagattac gcgcagaaaa aaaggatctc aagaagatcc   2760
tttgatcttt tctacggggt ctgacgctca gtggaacgaa aactcacgtt aagggatttt   2820
ggtcatgaga ttatcaaaaa ggatcttcac ctagatcctt ttaaattaaa aatgaagttt   2880
taaatcaatc taaagtatat atgagtaaac ttggtctgac agttaccaat gcttaatcag   2940
tgaggcacct atctcagcga tctgtctatt tcgttcatcc atagttgcct gactccccgt   3000
cgtgtagata actacgatac gggagggctt accatctggc cccagtgctg caatgatacc   3060
gcgagaccca cgctcaccgg ctccagattt atcagcaata aaccagccag ccggaagggc   3120
cgagcgcaga agtggtcctg caactttatc cgcctccatc cagtctatta attgttgccg   3180
ggaagctaga gtaagtagtt cgccagttaa tagtttgcgc aacgttgttg ccattgctac   3240
aggcatcgtg gtgtcacgct cgtcgtttgg tatggcttca ttcagctccg gttcccaacg   3300
atcaaggcga gttacatgat cccccatgtt gtgcaaaaaa gcggttagct ccttcggtcc   3360
tccgatcgtt gtcagaagta agttggccgc agtgttatca ctcatggtta tggcagcact   3420
gcataattct cttactgtca tgccatccgt aagatgcttt tctgtgactg gtgagtactc   3480
```

-continued aaccaagtca ttctgagaat agtgtatgcg gcgaccgagt tgctcttgcc cggcgtcaat 3540
acgggataat accgcgccac atagcagaac tttaaaagtg ctcatcattg gaaaacgttc 3600
ttcggggcga aaactctcaa ggatcttacc gctgttgaga tccagttcga tgtaacccac 3660
tcgtgcaccc aactgatctt cagcatcttt tactttcacc agcgtttctg ggtgagcaaa 3720
aacaggaagg caaaatgccg caaaaaaggg aataagggcg acacggaaat gttgaatact 3780
catactcttc ctttttcaat attattgaag catttatcag ggttattgtc tcatgagcgg 3840
atacatattt gaatgtattt agaaaaataa acaaataggg gttccgcgca catttccccg 3900
aaaagtgcca cctgacgtct aagaaaccat tattatcatg acattaacct ataaaaatag 3960
gcgtatcacg aggccctttc gtc 3983

<210> SEQ ID NO 42
<211> LENGTH: 14688
<212> TYPE: DNA
<213> ORGANISM: Artificial Sequence
<220> FEATURE:
<223> OTHER INFORMATION: Plasmid pZKLeuN-29E3

<400> SEQUENCE: 42
cgattgttgt ctactaacta tcgtacgata acttcgtata gcatacatta tacgaagtta 60
tcgcgtcgac gagtatctgt ctgactcgtc attgccgcct ttggagtacg actccaacta 120
tgagtgtgct tggatcactt tgacgataca ttcttcgttg gaggctgtgg gtctgacagc 180
tgcgttttcg gcgcggttgg ccgacaacaa tatcagctgc aacgtcattg ctggctttca 240
tcatgatcac atttttgtcg gcaaaggcga cgcccagaga gccattgacg ttctttctaa 300
tttggaccga tagccgtata gtccagtcta tctataagtt caactaactc gtaactatta 360
ccataacata tacttcactg ccccagataa ggttccgata aaaagttctg cagactaaat 420
ttatttcagt ctcctcttca ccaccaaaat gccctcctac gaagctcgag ctaacgtcca 480
caagtccgcc tttgccgctc gagtgctcaa gctcgtggca gccaagaaaa ccaacctgtg 540
tgcttctctg gatgttacca ccaccaagga gctcattgag cttgccgata aggtcggacc 600
ttatgtgtgc atgatcaaaa cccatatcga catcattgac gacttcacct acgccggcac 660
tgtgctcccc ctcaaggaac ttgctcttaa gcacggtttc ttcctgttcg aggacagaaa 720
gttcgcagat attggcaaca ctgtcaagca ccagtaccgg tgtcaccgaa tcgccgagtg 780
gtccgatatc accaacgccc acggtgtacc cggaaccgga atcattgctg gcctgcgagc 840
tggtgccgag gaaactgtct ctgaacagaa gaaggaggac gtctctgact acgagaactc 900
ccagtacaag gagttcctag tcccctctcc caacgagaag ctggccagag gtctgctcat 960
gctggccgag ctgtcttgca agggctctct ggccactggc gagtactcca agcagaccat 1020
tgagcttgcc cgatccgacc ccgagtttgt ggttggcttc attgcccaga accgacctaa 1080
gggcgactct gaggactggc ttattctgac ccccggggtg ggtcttgacg acaagggaga 1140
cgctctcgga cagcagtacc gaactgttga ggatgtcatg tctaccggaa cggatatcat 1200
aattgtcggc cgaggtctgt acggccagaa ccgagatcct attgaggagg ccaagcgata 1260
ccagaaggct ggctgggagg cttaccagaa gattaactgt tagaggttag actatggata 1320
tgtaatttaa ctgtgtatat agagagcgtg caagtatgga gcgcttgttc agcttgtatg 1380
atggtcagac gacctgtctg atcgagtatg tatgatactg cacaacctgt gtatccgcat 1440
gatctgtcca atggggcatg ttgttgtgtt tctcgatacg gagatgctgg gtacagtgct 1500

-continued

```
aatacgttga actacttata cttatatgag gctcgaagaa agctgacttg tgtatgactt   1560
attctcaact acatccccag tcacaatacc accactgcac taccactaca ccaaaaccat   1620
gatcaaacca cccatggact tcctggaggc agaagaactt gttatggaaa agctcaagag   1680
agagatcata acttcgtata gcatacatta tacgaagtta tcctgcaggt aaaggaattc   1740
tggagtttct gagagaaaaa ggcaagatac gtatgtaaca aagcgacgca tggtacaata   1800
ataccggagg catgtatcat agagagttag tggttcgatg atggcactgg tgcctggtat   1860
gactttatac ggctgactac atatttgtcc tcagacatac aattacagtc aagcacttac   1920
ccttggacat ctgtaggtac cccccggcca agacgatctc agcgtgtcgt atgtcggatt   1980
ggcgtagctc cctcgctcgt caattggctc ccatctactt tcttctgctt ggctacaccc   2040
agcatgtctg ctatggctcg ttttcgtgcc ttatctatcc tcccagtatt accaactcta   2100
aatgacatga tgtgattggg tctacacttt catatcagag ataaggagta gcacagttgc   2160
ataaaaagcc caactctaat cagcttcttc ctttcttgta attagtacaa aggtgattag   2220
cgaaatctgg aagcttagtt ggccctaaaa aaatcaaaaa aagcaaaaaa cgaaaaacga   2280
aaaaccacag ttttgagaac agggaggtaa cgaaggatcg tatatatata tatatatata   2340
tatacccacg gatcccgaga ccggcctttg attcttccct acaaccaacc attctcacca   2400
ccctaattca caaccatgga gtctggaccc atgcctgctg gcattccctt ccctgagtac   2460
tatgacttct ttatggactg gaagactccc ctggccatcg ctgccaccta cactgctgcc   2520
gtcggtctct tcaaccccaa ggttggcaag gtctcccgag tggttgccaa gtcggctaac   2580
gcaaagcctg ccgagcgaac ccagtccgga gctgccatga ctgccttcgt ctttgtgcac   2640
aacctcattc tgtgtgtcta ctctggcatc accttctact acatgtttcc tgctatggtc   2700
aagaacttcc gaacccacac actgcacgaa gcctactgcg acacggatca gtccctctgg   2760
aacaacgcac ttggctactg ggggttacctc ttctacctgt ccaagttcta cgaggtcatt   2820
gacaccatca tcatcatcct gaagggacga cggtcctcgc tgcttcagac ctaccaccat   2880
gctggagcca tgattaccat gtggtctggc atcaactacc aagccactcc catttggatc   2940
tttgtggtct tcaactcctt cattcacacc atcatgtact gttactatgc cttcacctct   3000
atcggattcc atcctcctgg caaaaagtac ctgacttcga tgcagattac tcagtttctg   3060
gtcggtatca ccattgccgt gtcctacctc ttcgttcctg gctgcatccg aacacccggt   3120
gctcagatgg ctgtctggat caacgtcggc tacctgtttc ccttgaccta tctgttcgtg   3180
gactttgcca agcgaaccta ctccaagcga tctgccattg ccgctcagaa aaaggctcag   3240
taagcggccg cattgatgat tggaaacaca cacatgggtt atatctaggt gagagttagt   3300
tggacagtta tatattaaat cagctatgcc aacggtaact tcattcatgt caacgaggaa   3360
ccagtgactg caagtaatat agaatttgac caccttgcca ttctcttgca ctcctttact   3420
atatctcatt tatttcttat atacaaatca cttcttcttc ccagcatcga gctcggaaac   3480
ctcatgagca ataacatcgt ggatctcgtc aatagagggc tttttggact ccttgctgtt   3540
ggccaccttg tccttgctgt ctggctcatt ctgtttcaac gccttttaat taacggagta   3600
ggtctcggtg tcggaagcga cgccagatcc gtcatcctcc tttcgctctc caaagtagat   3660
acctccgacg agctctcgga caatgatgaa gtcggtgccc tcaacgtttc ggatgggggga   3720
gagatcggcg agcttgggcg acagcagctg gcagggtcgc aggttggcgt acaggttcag   3780
gtcctttcgc agcttgagga gaccctgctc gggtcgcacg tcggttcgtc cgtcgggagt   3840
ggtccatacg gtgttggcag cgcctccgac agcaccgagc ataatagagt cagcctttcg   3900
```

-continued

```
gcagatgtcg agagtagcgt cggtgatggg ctcgccctcc ttctcaatgg cagctcctcc   3960
aatgagtcgg tcctcaaaca caaactcggt gccggaggcc tcagcaacag acttgagcac   4020
cttgacggcc tcggcaatca cctcggggcc acagaagtcg ccgccgagaa gaacaatctt   4080
cttggagtca gtcttggtct tcttagtttc gggttccatt gtggatgtgt gtggttgtat   4140
gtgtgatgtg gtgtgtggag tgaaaatctg tggctggcaa acgctcttgt atatatacgc   4200
acttttgccc gtgctatgtg gaagactaaa cctccgaaga ttgtgactca ggtagtgcgg   4260
tatcggctag ggacccaaac cttgtcgatg ccgatagcat gcgacgtcgg gcccaattcg   4320
ccctatagtg agtcgtatta caattcactg gccgtcgttt tacaacgtcg tgactgggaa   4380
aaccctggcg ttacccaact taatcgcctt gcagcacatc ccccttcgc cagctggcgt    4440
aatagcgaag aggcccgcac cgatcgccct tcccaacagt tgcgcagcct gaatggcgaa   4500
tggacgcgcc ctgtagcggc gcattaagcg cggcgggtgt ggtggttacg cgcagcgtga   4560
ccgctacact tgccagcgcc ctagcgcccg ctcctttcgc tttcttccct tcctttctcg   4620
ccacgttcgc cggctttccc cgtcaagctc taaatcgggg gctcccttta gggttccgat   4680
ttagtgcttt acggcacctc gaccccaaaa aacttgatta gggtgatggt tcacgtagtg   4740
ggccatcgcc ctgatagacg gtttttcgcc ctttgacgtt ggagtccacg ttctttaata   4800
gtggactctt gttccaaact ggaacaacac tcaaccctat ctcggtctat tcttttgatt   4860
tataagggat tttgccgatt tcggcctatt ggttaaaaaa tgagctgatt taacaaaaat   4920
ttaacgcgaa ttttaacaaa atattaacgc ttacaatttc ctgatgcggt attttctcct   4980
tacgcatctg tgcggtattt cacaccgcat caggtggcac ttttcgggga aatgtgcgcg   5040
gaacccctat ttgtttattt ttctaaatac attcaaatat gtatccgctc atgagacaat   5100
aaccctgata aatgcttcaa taatattgaa aaaggaagag tatgagtatt caacatttcc   5160
gtgtcgccct tattcccttt tttgcggcat tttgccttcc tgtttttgct cacccagaaa   5220
cgctggtgaa agtaaaagat gctgaagatc agttgggtgc acgagtgggt tacatcgaac   5280
tggatctcaa cagcggtaag atccttgaga gttttcgccc cgaagaacgt tttccaatga   5340
tgagcacttt taaagttctg ctatgtggcg cggtattatc ccgtattgac gccgggcaag   5400
agcaactcgg tcgccgcata cactattctc agaatgactt ggttgagtac tcaccagtca   5460
cagaaaagca tcttacggat ggcatgacag taagagaatt atgcagtgct gccataacca   5520
tgagtgataa cactgcggcc aacttacttc tgacaacgat cggaggaccg aaggagctaa   5580
ccgctttttt gcacaacatg ggggatcatg taactcgcct tgatcgttgg gaaccggagc   5640
tgaatgaagc cataccaaac gacgagcgtg acaccacgat gcctgtagca atggcaacaa   5700
cgttgcgcaa actattaact ggcgaactac ttactctagc ttcccggcaa caattaatag   5760
actggatgga ggcggataaa gttgcaggac cacttctgcg ctcggccctt ccggctggct   5820
ggtttattgc tgataaatct ggagccggtg agcgtgggtc tcgcggtatc attgcagcac   5880
tggggccaga tggtaagccc tcccgtatcg tagttatcta cacgacgggg agtcaggcaa   5940
ctatggatga acgaaataga cagatcgctg agataggtgc ctcactgatt aagcattggt   6000
aactgtcaga ccaagtttac tcatatatac tttagattga tttaaaactt catttttaat   6060
ttaaaaggat ctaggtgaag atcctttttg ataatctcat gaccaaaatc ccttaacgtg   6120
agttttcgtt ccactgagcg tcagaccccg tagaaaagat caaaggatct tcttgagatc   6180
cttttttctt gcgcgtaatc tgctgcttgc aaacaaaaaa accaccgcta ccagcggtgg   6240
```

-continued

```
tttgtttgcc ggatcaagag ctaccaactc tttttccgaa ggtaactggc ttcagcagag   6300

cgcagatacc aaatactgtt cttctagtgt agccgtagtt aggccaccac ttcaagaact   6360

ctgtagcacc gcctacatac ctcgctctgc taatcctgtt accagtggct gctgccagtg   6420

gcgataagtc gtgtcttacc gggttggact caagacgata gttaccggat aaggcgcagc   6480

ggtcgggctg aacggggggt tcgtgcacac agcccagctt ggagcgaacg acctacaccg   6540

aactgagata cctacagcgt gagctatgag aaagcgccac gcttcccgaa gggagaaagg   6600

cggacaggta tccggtaagc ggcagggtcg gaacaggaga gcgcacgagg gagcttccag   6660

ggggaaacgc ctggtatctt tatagtcctg tcgggtttcg ccacctctga cttgagcgtc   6720

gatttttgtg atgctcgtca ggggggcgga gcctatggaa aaacgccagc aacgcggcct   6780

ttttacggtt cctggccttt tgctggcctt ttgctcacat gttctttcct gcgttatccc   6840

ctgattctgt ggataaccgt attaccgcct ttgagtgagc tgataccgct cgccgcagcc   6900

gaacgaccga gcgcagcgag tcagtgagcg aggaagcgga agagcgccca atacgcaaac   6960

cgcctctccc cgcgcgttgg ccgattcatt aatgcagctg gcgcgcccac tgagctcgtc   7020

taacggactt gatatacaac caattaaaac aaatgaaaag aaatacagtt ctttgtatca   7080

tttgtaacaa ttaccctgta caaactaagg tattgaaatc ccacaatatt cccaaagtcc   7140

acccctttcc aaattgtcat gcctacaact catataccaa gcactaacct accaaacacc   7200

actaaaaccc cacaaaatat atcttaccga atatacagta acaagctacc accacactcg   7260

ttgggtgcag tcgccagctt aaagatatct atccacatca gccacaactc ccttccttta   7320

ataaaccgac tacacccttg gctattgagg ttatgagtga atatactgta gacaagacac   7380

tttcaagaag actgtttcca aaacgtacca ctgtcctcca ctacaaacac acccaatctg   7440

cttcttctag tcaaggttgc tacaccggta aattataaat catcatttca ttagcagggc   7500

agggcccttt ttatagagtc ttatacacta gcggaccctg ccggtagacc aacccgcagg   7560

cgcgtcagtt tgctccttcc atcaatgcgt cgtagaaacg acttactcct tcttgagcag   7620

ctccttgacc ttgttggcaa caagtctccg acctcggagg tggaggaaga gcctccgata   7680

tcggcggtag tgataccagc ctcgacggac tccttgacgg cagcctcaac agcgtcaccg   7740

gcgggcttca tgttaagaga gaacttgagc atcatggcgg cagacagaat ggtggcgtac   7800

gcaactaaca tgaatgaata cgatatacat caaagactat gatacgcagt attgcacact   7860

gtacgagtaa gagcactagc cactgcactc aagtgaaacc gttgcccggg tacgagtatg   7920

agtatgtaca gtatgtttag tattgtactt ggacagtgct tgtatcgtac attctcaagt   7980

gtcaaacata aatatccgtt gctatatcct cgcaccacca cgtagctcgc tatatccctg   8040

tgttgaatcc atccatcttg gattgccaat tgtgcacaca gaaccgggca ctcacttccc   8100

catccacact tgcggccgct taagcaacgg gcttgataac agcggggggg gtgcccacgt   8160

tgttgcggtt gcggaagaac agaacaccct taccagcacc ctcggcacca gcgctgggct   8220

caacccactg gcacatacgc gcactgcggt acatggcgcg gatgaagcca cgaggaccat   8280

cctggacatc agcccggtag tgcttgccca tgatgggctt aatggcctcg gtggcctcgt   8340

ccgcgttgta gaaggggatg ctgctgacgt agtggtggag gacatgagtc tcgatgatgc   8400

cgtggagaag gtggcggccg atgaagccca tctcacggtc aatggtagca gcggcaccac   8460

ggacgaagtt ccactcgtcg ttggtgtagt ggggaagggt agggtcggtg tgctggagga   8520

aggtgatggc aacgagccag tggttaaccc agaggtaggg aacaaagtac cagatggcca   8580

tgttgtagaa accgaacttc tgaacgagga agtacagagc agtggccatc agaccgatac   8640
```

-continued

```
caatatcgct gaggacgatg agcttagcgt cactgttctc gtacagaggg ctgcggggat   8700
cgaagtggtt aacaccaccg ccgaggccgt tatgcttgcc cttgccgcga ccctcacgct   8760
ggcgctcgtg gtagttgtgg ccggtaacat tggtgatgag gtagttgggc cagccaacga   8820
gctgctgaag gacgagcatg agaagagtga aagcgggggt ctcctcagta agatgagcga   8880
gctcgtgggt catctttccg agacgagtag cctgctgctc gcgggttcgg ggaacgaaga   8940
ccatgtcacg ctccatgttg ccagtggcct tgtggtgctt tcggtgggag atttgccagc   9000
tgaagtaggg gacaaggagg gaagagtgaa gaacccagcc agtaatgtcg ttgatgatgc   9060
gagaatcgga gaaagcaccg tgaccgcact catgggcaat aacccagaga ccagtaccga   9120
aaagaccctg aagaacggtg tacacggccc acagaccagc gcgggcgggg gtggaggga   9180
tatattcggg ggtcacaaag ttgtaccaga tgctgaaagt ggtagtcagg aggacaatgt   9240
cgcggaggat ataaccgtat cccttgagag cggagcgctt gaagcagtgc ttagggatgg   9300
cattgtagat gtccttgatg gtaaagtcgg gaacctcgaa ctggttgccg taggtgtcga   9360
gcatgacacc atactcggac ttgggcttgg cgatatcaac ctcggacatg gacgagagcg   9420
atgtggaaga ggccgagtgg cggggagagt ctgaaggaga gacggcggca gactcagaat   9480
ccgtcacagt agttgaggtg acggtgcgtc taagcgcagg gttctgcttg ggcagagccg   9540
aagtggacgc catggttgat gtgtgtttaa ttcaagaatg aatatagaga agagaagaag   9600
aaaaaagatt caattgagcc ggcgatgcag acccttatat aaatgttgcc ttggacagac   9660
ggagcaagcc cgcccaaacc tacgttcggt ataatatgtt aagcttttta acacaaaggt   9720
ttggcttggg gtaacctgat gtggtgcaaa agaccgggcg ttggcgagcc attgcgcggg   9780
cgaatggggc cgtgactcgt ctcaaattcg agggcgtgcc tcaattcgtg cccccgtggc   9840
tttttcccgc cgtttccgcc ccgtttgcac cactgcagcc gcttctttgg ttcggacacc   9900
ttgctgcgag ctaggtgcct tgtgctactt aaaaagtggc ctcccaacac caacatgaca   9960
tgagtgcgtg ggccaagaca cgttggcggg gtcgcagtcg gctcaatggc ccggaaaaaa  10020
cgctgctgga gctggttcgg acgcagtccg ccgcggcgta tggatatccg caaggttcca  10080
tagcgccatt gccctccgtc ggcgtctatc ccgcaacctc taaatagagc gggaatataa  10140
cccaagcttc tttttttcc tttaacacgc acaccccaa ctatcatgtt gctgctgctg  10200
tttgactcta ctctgtggag ggtgctccc acccaaccca acctacaggt ggatccggcg  10260
ctgtgattgg ctgataagtc tcctatccgg actaattctg accaatggga catgcgcgca  10320
ggacccaaat gccgcaatta cgtaacccca acgaaatgcc taccctctt tggagcccag  10380
cggccccaaa tccccccaag cagcccggtt ctaccggctt ccatctccaa gcacaagcag  10440
cccggttcta ccggcttcca tctccaagca cccctttctc cacaccccac aaaaagaccc  10500
gtgcaggaca tcctactgcg tcgacatcat ttaaattcct tcacttcaag ttcattcttc  10560
atctgcttct gttttacttt gacaggcaaa tgaagacatg gtacgacttg atggaggcca  10620
agaacgccat ttcaccccga gacaccgaag tgcctgaaat cctggctgcc cccattgata  10680
acatcggaaa ctacggtatt ccggaaagtg tatatagaac ctttccccag cttgtgtctg  10740
tggatatgga tggtgtaatc ccctttgagt actcgtcttg gcttctctcc gagcagtatg  10800
aggctctcta atctagcgca tttaatatct caatgtattt atatatttat cttctcatgc  10860
ggccgctcac tgaatctttt tggctccctt gtgcttcctg acgatatacg tttgcacata  10920
gaaattcaag aacaaacaca agactgtgcc aacataaaag taattgaaga accagccaaa  10980
```

-continued

```
catcctcatc ccatcttggc gataacaggg aatgttcctg tacttccaga caatgtagaa  11040
accaacattg aattgaatga tctgcattga tgtaatcagg gattttggca tggggaactt  11100
cagcttgatc aatctggtcc aataataacc gtacatgatc cagtggatga aaccattcaa  11160
cagcacaaaa atccaaacag cttcatttcg gtaattatag aacagccaca tatccatcgg  11220
tgcccccaaa tgatggaaga attgcaacca ggtcagaggc ttgcccatca gtggcaaata  11280
gaaggagtca atatactcca ggaacttgct caaatagaac aactgcgtgg tgatcctgaa  11340
gacgttgttg tcaaaagcct tctcgcagtt gtcagacata acaccgatgg tgtacatggc  11400
atatgccatt gagaggaatg atcccaacga ataaatggac atgagaaggt tgtaattggt  11460
gaaaacaaac ttcatacgag actgaccttt tggaccaagg gggccaagag tgaacttcaa  11520
gatgacaaat gcgatggaca agtaaagcac ctcacagtga ctggcatcac tccagagttg  11580
ggcataatca actggttggg taaaacttcc tgcccaattg agactatttc attcaccacc  11640
tccatggcca ttgctgtaga tatgtcttgt gtgtaagggg gttggggtgg ttgtttgtgt  11700
tcttgacttt tgtgttagca agggaagacg ggcaaaaaag tgagtgtggt tgggagggag  11760
agacgagcct tatatataat gcttgtttgt gtttgtgcaa gtggacgccg aaacgggcag  11820
gagccaaact aaacaaggca gacaatgcga gcttaattgg attgcctgat gggcaggggt  11880
tagggctcga tcaatggggg tgcgaagtga caaaattggg aattaggttc gcaagcaagg  11940
ctgacaagac tttggcccaa acatttgtac gcggtggaca acaggagcca cccatcgtct  12000
gtcacgggct agccggtcgt gcgtcctgtc aggctccacc taggctccat gccactccat  12060
acaatcccac tagtgtaccg ctaggccgct tttagctccc atctaagacc cccccaaaac  12120
ctccactgta cagtgcactg tactgtgtgg cgatcaaggg caagggaaaa aaggcgcaaa  12180
catgcacgca tggaatgacg taggtaaggc gttactagac tgaaaagtgg cacatttcgg  12240
cgtgccaaag ggtcctaggt gcgtttcgcg agctgggcgc caggccaagc cgctccaaaa  12300
cgcctctccg actccctcca gcggcctcca tatccccatc cctctccaca gcaatgttgt  12360
taagccttgc aaacgaaaaa atagaaaggc taataagctt ccaatattgt ggtgtacgct  12420
gcataacgca acaatgagcg ccaaacaaca cacacacaca gcacacagca gcattaacca  12480
cgatgaacag catgacatta caggtgggtg tgtaatcagg gccctgattg ctggtggtgg  12540
gagcccccat catgggcaga tctgcgtaca ctgtttaaac agtgtacgca gatctactat  12600
agaggaacat ttaaattgcc ccggagaaga cggccaggcc gcctagatga caaattcaac  12660
aactcacagc tgactttctg ccattgccac tagggggggg ccttttata tggccaagcc  12720
aagctctcca cgtcggttgg gctgcaccca acaataaatg ggtagggttg caccaacaaa  12780
gggatgggat ggggggtaga agatacgagg ataacggggc tcaatggcac aaataagaac  12840
gaatactgcc attaagactc gtgatccagc gactgacacc attgcatcat ctaagggcct  12900
caaaactacc tcggaactgc tgcgctgatc tggacaccac agaggttccg agcactttag  12960
gttgcaccaa atgtcccacc aggtgcaggc agaaaacgct ggaacagcgt gtacagtttg  13020
tcttaacaaa aagtgagggc gctgaggtcg agcagggtgg tgtgacttgt tatagccttt  13080
agagctgcga aagcgcgtat ggatttggct catcaggcca gattgagggt ctgtggacac  13140
atgtcatgtt agtgtacttc aatcgccccc tggatatagc cccgacaata ggccgtggcc  13200
tcattttttt gccttccgca catttccatt gctcgatacc cacaccttgc ttctcctgca  13260
cttgccaacc ttaatactgg tttacattga ccaacatctt acaagcgggg ggcttgtcta  13320
gggtatatat aaacagtggc tctcccaatc ggttgccagt ctcttttttc ctttctttcc  13380
```

-continued

```
ccacagattc gaaatctaaa ctacacatca cagaattccg agccgtgagt atccacgaca  13440

agatcagtgt cgagacgacg cgttttgtgt aatgacacaa tccgaaagtc gctagcaaca  13500

cacactctct acacaaacta acccagctct ggtaccatgg aggtcgtgaa cgaaatcgtc  13560

tccattggcc aggaggttct tcccaaggtc gactatgctc agctctggtc tgatgcctcg  13620

cactgcgagg tgctgtacct ctccatcgcc ttcgtcatcc tgaagttcac ccttggtcct  13680

ctcggaccca agggtcagtc tcgaatgaag tttgtgttca ccaactacaa cctgctcatg  13740

tccatctact cgctgggctc cttcctctct atggcctacg ccatgtacac cattggtgtc  13800

atgtccgaca actgcgagaa ggctttcgac aacaatgtct tccgaatcac cactcagctg  13860

ttctacctca gcaagttcct cgagtacatt gactccttct atctgcccct catgggcaag  13920

cctctgacct ggttgcagtt ctttcaccat ctcggagctc ctatggacat gtggctgttc  13980

tacaactacc gaaacgaagc cgtttggatc tttgtgctgc tcaacggctt cattcactgg  14040

atcatgtacg gctactattg gacccgactg atcaagctca agttccctat gcccaagtcc  14100

ctgattactt ctatgcagat cattcagttc aacgttggct tctacatcgt ctggaagtac  14160

cggaacattc cctgctaccg acaagatgga atgagaatgt ttggctggtt tttcaactac  14220

ttctacgttg gtactgtcct gtgtctgttc ctcaacttct acgtgcagac ctacatcgtc  14280

cgaaagcaca agggagccaa aaagattcag tgagcggccg catgtacata caagattatt  14340

tatagaaatg aatcgcgatc gaacaaagag tacgagtgta cgagtagggg atgatgataa  14400

aagtggaaga agttccgcat ctttggattt atcaacgtgt aggacgatac ttcctgtaaa  14460

aatgcaatgt ctttaccata ggttctgctg tagatgttat taactaccat taacatgtct  14520

acttgtacag ttgcagacca gttggagtat agaatggtac acttaccaaa aagtgttgat  14580

ggttgtaact acgatatata aaactgttga cgggatcccc gctgatatgc ctaaggaaca  14640

atcaaagagg aagatattaa ttcagaatgc tagtatacag ttagggat              14688
```

```
<210> SEQ ID NO 43
<211> LENGTH: 1434
<212> TYPE: DNA
<213> ORGANISM: Fusarium monoliforme
<220> FEATURE:
<221> NAME/KEY: CDS
<222> LOCATION: (1)..(1434)
<223> OTHER INFORMATION: delta-12 desaturase
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: WO 2005/047485
<311> PATENT FILING DATE: 2004-11-12
<312> PUBLICATION DATE: 2005-05-26
<313> RELEVANT RESIDUES IN SEQ ID NO: (1)..(1434)
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: US 2005-0216975-A1
<311> PATENT FILING DATE: 2004-11-10
<312> PUBLICATION DATE: 2005-09-29
<313> RELEVANT RESIDUES IN SEQ ID NO: (1)..(1434)

<400> SEQUENCE: 43

atg gcg tcc act tcg gct ctg ccc aag cag aac cct gcg ctt aga cgc       48
Met Ala Ser Thr Ser Ala Leu Pro Lys Gln Asn Pro Ala Leu Arg Arg
1               5                   10                  15

acc gtc acc tca act act gtg acg gat tct gag tct gcc gcc gtc tct       96
Thr Val Thr Ser Thr Thr Val Thr Asp Ser Glu Ser Ala Ala Val Ser
            20                  25                  30
```

-continued

```
cct tca gac tct ccc cgc cac tcg gcc tct tcc aca tcg ctc tcg tcc      144
Pro Ser Asp Ser Pro Arg His Ser Ala Ser Ser Thr Ser Leu Ser Ser
        35                  40                  45

atg tcc gag gtt gat atc gcc aag ccc aag tcc gag tat ggt gtc atg      192
Met Ser Glu Val Asp Ile Ala Lys Pro Lys Ser Glu Tyr Gly Val Met
    50                  55                  60

ctc gac acc tac ggc aac cag ttc gag gtt ccc gac ttt acc atc aag      240
Leu Asp Thr Tyr Gly Asn Gln Phe Glu Val Pro Asp Phe Thr Ile Lys
65                  70                  75                  80

gac atc tac aat gcc atc cct aag cac tgc ttc aag cgc tcc gct ctc      288
Asp Ile Tyr Asn Ala Ile Pro Lys His Cys Phe Lys Arg Ser Ala Leu
                85                  90                  95

aag gga tac ggt tat atc ctc cgc gac att gtc ctc ctg act acc act      336
Lys Gly Tyr Gly Tyr Ile Leu Arg Asp Ile Val Leu Leu Thr Thr Thr
            100                 105                 110

ttc agc atc tgg tac aac ttt gtg acc ccc gaa tat atc ccc tcc acc      384
Phe Ser Ile Trp Tyr Asn Phe Val Thr Pro Glu Tyr Ile Pro Ser Thr
        115                 120                 125

ccc gcc cgc gct ggt ctg tgg gcc gtg tac acc gtt ctt cag ggt ctt      432
Pro Ala Arg Ala Gly Leu Trp Ala Val Tyr Thr Val Leu Gln Gly Leu
    130                 135                 140

ttc ggt act ggt ctc tgg gtt att gcc cat gag tgc ggt cac ggt gct      480
Phe Gly Thr Gly Leu Trp Val Ile Ala His Glu Cys Gly His Gly Ala
145                 150                 155                 160

ttc tcc gat tct cgc atc atc aac gac att act ggc tgg gtt ctt cac      528
Phe Ser Asp Ser Arg Ile Ile Asn Asp Ile Thr Gly Trp Val Leu His
                165                 170                 175

tct tcc ctc ctt gtc ccc tac ttc agc tgg caa atc tcc cac cga aag      576
Ser Ser Leu Leu Val Pro Tyr Phe Ser Trp Gln Ile Ser His Arg Lys
            180                 185                 190

cac cac aag gcc act ggc aac atg gag cgt gac atg gtc ttc gtt ccc      624
His His Lys Ala Thr Gly Asn Met Glu Arg Asp Met Val Phe Val Pro
        195                 200                 205

cga acc cgc gag cag cag gct act cgt ctc gga aag atg acc cac gag      672
Arg Thr Arg Glu Gln Gln Ala Thr Arg Leu Gly Lys Met Thr His Glu
    210                 215                 220

ctc gct cat ctt act gag gag acc ccc gct ttc act ctt ctc atg ctc      720
Leu Ala His Leu Thr Glu Glu Thr Pro Ala Phe Thr Leu Leu Met Leu
225                 230                 235                 240

gtc ctt cag cag ctc gtt ggc tgg ccc aac tac ctc atc acc aat gtt      768
Val Leu Gln Gln Leu Val Gly Trp Pro Asn Tyr Leu Ile Thr Asn Val
                245                 250                 255

acc ggc cac aac tac cac gag cgc cag cgt gag ggt cgc ggc aag ggc      816
Thr Gly His Asn Tyr His Glu Arg Gln Arg Glu Gly Arg Gly Lys Gly
            260                 265                 270

aag cat aac ggc ctc ggc ggt ggt gtt aac cac ttc gat ccc cgc agc      864
Lys His Asn Gly Leu Gly Gly Gly Val Asn His Phe Asp Pro Arg Ser
        275                 280                 285

cct ctg tac gag aac agt gac gct aag ctc atc gtc ctc agc gat att      912
Pro Leu Tyr Glu Asn Ser Asp Ala Lys Leu Ile Val Leu Ser Asp Ile
    290                 295                 300

ggt atc ggt ctg atg gcc act gct ctg tac ttc ctc gtt cag aag ttc      960
Gly Ile Gly Leu Met Ala Thr Ala Leu Tyr Phe Leu Val Gln Lys Phe
305                 310                 315                 320

ggt ttc tac aac atg gcc atc tgg tac ttt gtt ccc tac ctc tgg gtt     1008
Gly Phe Tyr Asn Met Ala Ile Trp Tyr Phe Val Pro Tyr Leu Trp Val
                325                 330                 335

aac cac tgg ctc gtt gcc atc acc ttc ctc cag cac acc gac cct acc     1056
Asn His Trp Leu Val Ala Ile Thr Phe Leu Gln His Thr Asp Pro Thr
            340                 345                 350
```

-continued

```
ctt ccc cac tac acc aac gac gag tgg aac ttc gtc cgt ggt gcc gct      1104
Leu Pro His Tyr Thr Asn Asp Glu Trp Asn Phe Val Arg Gly Ala Ala
        355                 360                 365

gct acc att gac cgt gag atg ggc ttc atc ggc cgc cac ctt ctc cac      1152
Ala Thr Ile Asp Arg Glu Met Gly Phe Ile Gly Arg His Leu Leu His
    370                 375                 380

ggc atc atc gag act cat gtc ctc cac cac tac gtc agc agc atc ccc      1200
Gly Ile Ile Glu Thr His Val Leu His His Tyr Val Ser Ser Ile Pro
385                 390                 395                 400

ttc tac aac gcg gac gag gcc acc gag gcc att aag ccc atc atg ggc      1248
Phe Tyr Asn Ala Asp Glu Ala Thr Glu Ala Ile Lys Pro Ile Met Gly
                405                 410                 415

aag cac tac cgg gct gat gtc cag gat ggt cct cgt ggc ttc atc cgc      1296
Lys His Tyr Arg Ala Asp Val Gln Asp Gly Pro Arg Gly Phe Ile Arg
            420                 425                 430

gcc atg tac cgc agt gcg cgt atg tgc cag tgg gtt gag ccc agc gct      1344
Ala Met Tyr Arg Ser Ala Arg Met Cys Gln Trp Val Glu Pro Ser Ala
        435                 440                 445

ggt gcc gag ggt gct ggt aag ggt gtt ctg ttc ttc cgc aac cgc aac      1392
Gly Ala Glu Gly Ala Gly Lys Gly Val Leu Phe Phe Arg Asn Arg Asn
    450                 455                 460

aac gtg ggc acc ccc ccc gct gtt atc aag ccc gtt gct taa              1434
Asn Val Gly Thr Pro Pro Ala Val Ile Lys Pro Val Ala
465                 470                 475


<210> SEQ ID NO 44
<211> LENGTH: 477
<212> TYPE: PRT
<213> ORGANISM: Fusarium monoliforme

<400> SEQUENCE: 44

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205
```

-continued

```
Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475
```

<210> SEQ ID NO 45
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: synthetic delta-9 elongase (codon-optimized for Yarrowia lipolytica)
<300> PUBLICATION INFORMATION:
<302> TITLE: DELTA-9 ELONGASES AND THEIR USE IN MAKING POLYUNSATURATED FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(777)
<300> PUBLICATION INFORMATION:
<302> TITLE: DELTA-9 ELONGASES AND THEIR USE IN MAKING POLYUNSATURATED FATTY ACIDS
<310> PATENT DOCUMENT NUMBER: US-2007-0117190-A1
<311> PATENT FILING DATE: 2006-11-16
<312> PUBLICATION DATE: 2007-05-24
<313> RELEVANT RESIDUES IN SEQ ID NO: (1)..(777)

<400> SEQUENCE: 45

-continued

```
atg gag gtc gtg aac gaa atc gtc tcc att ggc cag gag gtt ctt ccc        48
Met Glu Val Val Asn Glu Ile Val Ser Ile Gly Gln Glu Val Leu Pro
1               5                   10                  15

aag gtc gac tat gct cag ctc tgg tct gat gcc tcg cac tgc gag gtg        96
Lys Val Asp Tyr Ala Gln Leu Trp Ser Asp Ala Ser His Cys Glu Val
            20                  25                  30

ctg tac ctc tcc atc gcc ttc gtc atc ctg aag ttc acc ctt ggt cct       144
Leu Tyr Leu Ser Ile Ala Phe Val Ile Leu Lys Phe Thr Leu Gly Pro
        35                  40                  45

ctc gga ccc aag ggt cag tct cga atg aag ttt gtg ttc acc aac tac       192
Leu Gly Pro Lys Gly Gln Ser Arg Met Lys Phe Val Phe Thr Asn Tyr
    50                  55                  60

aac ctg ctc atg tcc atc tac tcg ctg ggc tcc ttc ctc tct atg gcc       240
Asn Leu Leu Met Ser Ile Tyr Ser Leu Gly Ser Phe Leu Ser Met Ala
65                  70                  75                  80

tac gcc atg tac acc att ggt gtc atg tcc gac aac tgc gag aag gct       288
Tyr Ala Met Tyr Thr Ile Gly Val Met Ser Asp Asn Cys Glu Lys Ala
                85                  90                  95

ttc gac aac aat gtc ttc cga atc acc act cag ctg ttc tac ctc agc       336
Phe Asp Asn Asn Val Phe Arg Ile Thr Thr Gln Leu Phe Tyr Leu Ser
            100                 105                 110

aag ttc ctc gag tac att gac tcc ttc tat ctg ccc ctc atg ggc aag       384
Lys Phe Leu Glu Tyr Ile Asp Ser Phe Tyr Leu Pro Leu Met Gly Lys
        115                 120                 125

cct ctg acc tgg ttg cag ttc ttt cac cat ctc gga gct cct atg gac       432
Pro Leu Thr Trp Leu Gln Phe Phe His His Leu Gly Ala Pro Met Asp
    130                 135                 140

atg tgg ctg ttc tac aac tac cga aac gaa gcc gtt tgg atc ttt gtg       480
Met Trp Leu Phe Tyr Asn Tyr Arg Asn Glu Ala Val Trp Ile Phe Val
145                 150                 155                 160

ctg ctc aac ggc ttc att cac tgg atc atg tac ggc tac tat tgg acc       528
Leu Leu Asn Gly Phe Ile His Trp Ile Met Tyr Gly Tyr Tyr Trp Thr
                165                 170                 175

cga ctg atc aag ctc aag ttc cct atg ccc aag tcc ctg att act tct       576
Arg Leu Ile Lys Leu Lys Phe Pro Met Pro Lys Ser Leu Ile Thr Ser
            180                 185                 190

atg cag atc att cag ttc aac gtt ggc ttc tac atc gtc tgg aag tac       624
Met Gln Ile Ile Gln Phe Asn Val Gly Phe Tyr Ile Val Trp Lys Tyr
        195                 200                 205

cgg aac att ccc tgc tac cga caa gat gga atg aga atg ttt ggc tgg       672
Arg Asn Ile Pro Cys Tyr Arg Gln Asp Gly Met Arg Met Phe Gly Trp
    210                 215                 220

ttt ttc aac tac ttc tac gtt ggt act gtc ctg tgt ctg ttc ctc aac       720
Phe Phe Asn Tyr Phe Tyr Val Gly Thr Val Leu Cys Leu Phe Leu Asn
225                 230                 235                 240

ttc tac gtg cag acc tac atc gtc cga aag cac aag gga gcc aaa aag       768
Phe Tyr Val Gln Thr Tyr Ile Val Arg Lys His Lys Gly Ala Lys Lys
                245                 250                 255

att cag tga                                                            777
Ile Gln
```

<210> SEQ ID NO 46
<211> LENGTH: 258
<212> TYPE: PRT
<213> ORGANISM: Euglena gracilis

<400> SEQUENCE: 46

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
```

-continued

```
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln
```

<210> SEQ ID NO 47
<211> LENGTH: 34
<212> TYPE: DNA
<213> ORGANISM: Escherichia coli

<400> SEQUENCE: 47

```
ataacttcgt ataatgtatg ctatacgaag ttat                               34
```

<210> SEQ ID NO 48
<211> LENGTH: 828
<212> TYPE: DNA
<213> ORGANISM: Mortierella alpina
<220> FEATURE:
<221> NAME/KEY: CDS
<222> LOCATION: (1)..(828)
<223> OTHER INFORMATION: synthetic C16/18 elongase (codon-optimized for Yarrowia lipolytica)
<300> PUBLICATION INFORMATION:
<302> TITLE: A MORTIERELLA ALPINA C16/18 FATTY ACID ELONGASE
<310> PATENT DOCUMENT NUMBER: US 2007-0087420-A1
<311> PATENT FILING DATE: 2005-10-19
<312> PUBLICATION DATE: 2007-04-19
<313> RELEVANT RESIDUES IN SEQ ID NO: (1)..(828)
<300> PUBLICATION INFORMATION:
<302> TITLE: A MORTIERELLA ALPINA C16/18 FATTY ACID ELONGASE
<310> PATENT DOCUMENT NUMBER: WO 2007/046817
<311> PATENT FILING DATE: 2005-11-04
<312> PUBLICATION DATE: 2007-04-26
<313> RELEVANT RESIDUES IN SEQ ID NO: (1)..(828)

-continued

```
<400> SEQUENCE: 48

atg gag tct gga ccc atg cct gct ggc att ccc ttc cct gag tac tat       48
Met Glu Ser Gly Pro Met Pro Ala Gly Ile Pro Phe Pro Glu Tyr Tyr
1               5                   10                  15

gac ttc ttt atg gac tgg aag act ccc ctg gcc atc gct gcc acc tac       96
Asp Phe Phe Met Asp Trp Lys Thr Pro Leu Ala Ile Ala Ala Thr Tyr
            20                  25                  30

act gct gcc gtc ggt ctc ttc aac ccc aag gtt ggc aag gtc tcc cga      144
Thr Ala Ala Val Gly Leu Phe Asn Pro Lys Val Gly Lys Val Ser Arg
        35                  40                  45

gtg gtt gcc aag tcg gct aac gca aag cct gcc gag cga acc cag tcc      192
Val Val Ala Lys Ser Ala Asn Ala Lys Pro Ala Glu Arg Thr Gln Ser
    50                  55                  60

gga gct gcc atg act gcc ttc gtc ttt gtg cac aac ctc att ctg tgt      240
Gly Ala Ala Met Thr Ala Phe Val Phe Val His Asn Leu Ile Leu Cys
65                  70                  75                  80

gtc tac tct ggc atc acc ttc tac tac atg ttt cct gct atg gtc aag      288
Val Tyr Ser Gly Ile Thr Phe Tyr Tyr Met Phe Pro Ala Met Val Lys
                85                  90                  95

aac ttc cga acc cac aca ctg cac gaa gcc tac tgc gac acg gat cag      336
Asn Phe Arg Thr His Thr Leu His Glu Ala Tyr Cys Asp Thr Asp Gln
            100                 105                 110

tcc ctc tgg aac aac gca ctt ggc tac tgg ggt tac ctc ttc tac ctg      384
Ser Leu Trp Asn Asn Ala Leu Gly Tyr Trp Gly Tyr Leu Phe Tyr Leu
        115                 120                 125

tcc aag ttc tac gag gtc att gac acc atc atc atc atc ctg aag gga      432
Ser Lys Phe Tyr Glu Val Ile Asp Thr Ile Ile Ile Ile Leu Lys Gly
    130                 135                 140

cga cgg tcc tcg ctg ctt cag acc tac cac cat gct gga gcc atg att      480
Arg Arg Ser Ser Leu Leu Gln Thr Tyr His His Ala Gly Ala Met Ile
145                 150                 155                 160

acc atg tgg tct ggc atc aac tac caa gcc act ccc att tgg atc ttt      528
Thr Met Trp Ser Gly Ile Asn Tyr Gln Ala Thr Pro Ile Trp Ile Phe
                165                 170                 175

gtg gtc ttc aac tcc ttc att cac acc atc atg tac tgt tac tat gcc      576
Val Val Phe Asn Ser Phe Ile His Thr Ile Met Tyr Cys Tyr Tyr Ala
            180                 185                 190

ttc acc tct atc gga ttc cat cct cct ggc aaa aag tac ctg act tcg      624
Phe Thr Ser Ile Gly Phe His Pro Pro Gly Lys Lys Tyr Leu Thr Ser
        195                 200                 205

atg cag att act cag ttt ctg gtc ggt atc acc att gcc gtg tcc tac      672
Met Gln Ile Thr Gln Phe Leu Val Gly Ile Thr Ile Ala Val Ser Tyr
    210                 215                 220

ctc ttc gtt cct ggc tgc atc cga aca ccc ggt gct cag atg gct gtc      720
Leu Phe Val Pro Gly Cys Ile Arg Thr Pro Gly Ala Gln Met Ala Val
225                 230                 235                 240

tgg atc aac gtc ggc tac ctg ttt ccc ttg acc tat ctg ttc gtg gac      768
Trp Ile Asn Val Gly Tyr Leu Phe Pro Leu Thr Tyr Leu Phe Val Asp
                245                 250                 255

ttt gcc aag cga acc tac tcc aag cga tct gcc att gcc gct cag aaa      816
Phe Ala Lys Arg Thr Tyr Ser Lys Arg Ser Ala Ile Ala Ala Gln Lys
            260                 265                 270

aag gct cag taa                                                      828
Lys Ala Gln
        275

<210> SEQ ID NO 49
<211> LENGTH: 275
<212> TYPE: PRT
<213> ORGANISM: Mortierella alpina
```

-continued

<400> SEQUENCE: 49

Met Glu Ser Gly Pro Met Pro Ala Gly Ile Pro Phe Pro Glu Tyr Tyr
1 5 10 15

Asp Phe Phe Met Asp Trp Lys Thr Pro Leu Ala Ile Ala Ala Thr Tyr
20 25 30

Thr Ala Ala Val Gly Leu Phe Asn Pro Lys Val Gly Lys Val Ser Arg
35 40 45

Val Val Ala Lys Ser Ala Asn Ala Lys Pro Ala Glu Arg Thr Gln Ser
50 55 60

Gly Ala Ala Met Thr Ala Phe Val Phe Val His Asn Leu Ile Leu Cys
65 70 75 80

Val Tyr Ser Gly Ile Thr Phe Tyr Tyr Met Phe Pro Ala Met Val Lys
85 90 95

Asn Phe Arg Thr His Thr Leu His Glu Ala Tyr Cys Asp Thr Asp Gln
100 105 110

Ser Leu Trp Asn Asn Ala Leu Gly Tyr Trp Gly Tyr Leu Phe Tyr Leu
115 120 125

Ser Lys Phe Tyr Glu Val Ile Asp Thr Ile Ile Ile Ile Leu Lys Gly
130 135 140

Arg Arg Ser Ser Leu Leu Gln Thr Tyr His His Ala Gly Ala Met Ile
145 150 155 160

Thr Met Trp Ser Gly Ile Asn Tyr Gln Ala Thr Pro Ile Trp Ile Phe
165 170 175

Val Val Phe Asn Ser Phe Ile His Thr Ile Met Tyr Cys Tyr Tyr Ala
180 185 190

Phe Thr Ser Ile Gly Phe His Pro Pro Gly Lys Lys Tyr Leu Thr Ser
195 200 205

Met Gln Ile Thr Gln Phe Leu Val Gly Ile Thr Ile Ala Val Ser Tyr
210 215 220

Leu Phe Val Pro Gly Cys Ile Arg Thr Pro Gly Ala Gln Met Ala Val
225 230 235 240

Trp Ile Asn Val Gly Tyr Leu Phe Pro Leu Thr Tyr Leu Phe Val Asp
245 250 255

Phe Ala Lys Arg Thr Tyr Ser Lys Arg Ser Ala Ile Ala Ala Gln Lys
260 265 270

Lys Ala Gln
275

<210> SEQ ID NO 50
<211> LENGTH: 8739
<212> TYPE: DNA
<213> ORGANISM: Artificial Sequence
<220> FEATURE:
<223> OTHER INFORMATION: Plasmid pY116

<400> SEQUENCE: 50
ggccgccacc gcggcccgag attccggcct cttcggccgc caagcgaccc gggtggacgt 60
ctagaggtac ctagcaatta acagatagtt tgccggtgat aattctctta acctcccaca 120
ctcctttgac ataacgattt atgtaacgaa actgaaattt gaccagatat tgtgtccgcg 180
gtggagctcc agcttttgtt ccctttagtg agggtttaaa cgagcttggc gtaatcatgg 240
tcatagctgt ttcctgtgtg aaattgttat ccgctcacaa ttccacacaa cgtacgagcc 300
ggaagcataa agtgtaaagc ctggggtgcc taatgagtga gctaactcac attaattgcg 360

-continued

```
ttgcgctcac tgcccgcttt ccagtcggga aacctgtcgt gccagctgca ttaatgaatc    420
ggccaacgcg cggggagagg cggtttgcgt attgggcgct cttccgcttc ctcgctcact    480
gactcgctgc gctcggtcgt tcggctgcgg cgagcggtat cagctcactc aaaggcggta    540
atacggttat ccacagaatc aggggataac gcaggaaaga acatgtgagc aaaaggccag    600
caaaaggcca ggaaccgtaa aaaggccgcg ttgctggcgt ttttccatag gctccgcccc    660
cctgacgagc atcacaaaaa tcgacgctca agtcagaggt ggcgaaaccc gacaggacta    720
taaagatacc aggcgtttcc ccctggaagc tccctcgtgc gctctcctgt tccgaccctg    780
ccgcttaccg gatacctgtc cgcctttctc ccttcgggaa gcgtggcgct ttctcatagc    840
tcacgctgta ggtatctcag ttcggtgtag gtcgttcgct ccaagctggg ctgtgtgcac    900
gaaccccccg ttcagcccga ccgctgcgcc ttatccggta actatcgtct tgagtccaac    960
ccggtaagac acgacttatc gccactggca gcagccactg gtaacaggat tagcagagcg   1020
aggtatgtag gcggtgctac agagttcttg aagtggtggc ctaactacgg ctacactaga   1080
aggacagtat ttggtatctg cgctctgctg aagccagtta ccttcggaaa aagagttggt   1140
agctcttgat ccggcaaaca aaccaccgct ggtagcggtg gtttttttgt ttgcaagcag   1200
cagattacgc gcagaaaaaa aggatctcaa gaagatcctt tgatcttttc tacggggtct   1260
gacgctcagt ggaacgaaaa ctcacgttaa gggattttgg tcatgagatt atcaaaaagg   1320
atcttcacct agatcctttt aaattaaaaa tgaagtttta aatcaatcta aagtatatat   1380
gagtaaactt ggtctgacag ttaccaatgc ttaatcagtg aggcacctat ctcagcgatc   1440
tgtctatttc gttcatccat agttgcctga ctccccgtcg tgtagataac tacgatacgg   1500
gagggcttac catctggccc cagtgctgca atgataccgc gagacccacg ctcaccggct   1560
ccagatttat cagcaataaa ccagccagcc ggaagggccg agcgcagaag tggtcctgca   1620
actttatccg cctccatcca gtctattaat tgttgccggg aagctagagt aagtagttcg   1680
ccagttaata gtttgcgcaa cgttgttgcc attgctacag gcatcgtggt gtcacgctcg   1740
tcgtttggta tggcttcatt cagctccggt tcccaacgat caaggcgagt tacatgatcc   1800
cccatgttgt gcaaaaaagc ggttagctcc ttcggtcctc cgatcgttgt cagaagtaag   1860
ttggccgcag tgttatcact catggttatg gcagcactgc ataattctct tactgtcatg   1920
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg tttttcgccc tttgacgttg gagtccacgt tctttaatag tggactcttg   2700
ttccaaactg gaacaacact caaccctatc tcggtctatt cttttgattt ataagggatt   2760
```

-continued

```
ttgccgattt cggcctattg gttaaaaaat gagctgattt aacaaaaatt taacgcgaat   2820
tttaacaaaa tattaacgct tacaatttcc attcgccatt caggctgcgc aactgttggg   2880
aagggcgatc ggtgcgggcc tcttcgctat tacgccagct ggcgaaaggg ggatgtgctg   2940
caaggcgatt aagttgggta acgccagggt tttcccagtc acgacgttgt aaaacgacgg   3000
ccagtgaatt gtaatacgac tcactatagg gcgaattggg taccgggccc cccctcgagg   3060
tcgatggtgt cgataagctt gatatcgaat tcatgtcaca caaaccgatc ttcgcctcaa   3120
ggaaacctaa ttctacatcc gagagactgc cgagatccag tctacactga ttaattttcg   3180
ggccaataat ttaaaaaaat cgtgttatat aatattatat gtattatata tatacatcat   3240
gatgatactg acagtcatgt cccattgcta aatagacaga ctccatctgc cgcctccaac   3300
tgatgttctc aatatttaag ggtcatctc gcattgttta ataataaaca gactccatct   3360
accgcctcca aatgatgttc tcaaaatata ttgtatgaac ttatttttat tacttagtat   3420
tattagacaa cttacttgct ttatgaaaaa cacttcctat ttaggaaaca atttataatg   3480
gcagttcgtt catttaacaa tttatgtaga ataaatgtta taaatgcgta tgggaaatct   3540
taaatatgga tagcataaat gatatctgca ttgcctaatt cgaaatcaac agcaacgaaa   3600
aaaatccctt gtacaacata aatagtcatc gagaaatatc aactatcaaa gaacagctat   3660
tcacacgtta ctattgagat tattattgga cgagaatcac acactcaact gtctttctct   3720
cttctagaaa tacaggtaca agtatgtact attctcattg ttcatacttc tagtcatttc   3780
atcccacata ttccttggat ttctctccaa tgaatgacat tctatcttgc aaattcaaca   3840
attataataa gatataccaa agtagcggta tagtggcaat caaaaagctt ctctggtgtg   3900
cttctcgtat ttatttttat tctaatgatc cattaaaggt atatatttat ttcttgttat   3960
ataatccttt tgtttattac atgggctgga tacataaagg tattttgatt taatttttg    4020
cttaaattca atccccccctc gttcagtgtc aactgtaatg gtaggaaatt accatacttt   4080
tgaagaagca aaaaaaatga aagaaaaaaa aaatcgtatt tccaggttag acgttccgca   4140
gaatctagaa tgcggtatgc ggtacattgt tcttcgaacg taaaagttgc gctccctgag   4200
atattgtaca tttttgcttt tacaagtaca agtacatcgt acaactatgt actactgttg   4260
atgcatccac aacagtttgt tttgtttttt tttgtttttt ttttttctaa tgattcatta   4320
ccgctatgta tacctacttg tacttgtagt aagccgggtt attggcgttc aattaatcat   4380
agacttatga atctgcacgg tgtgcgctgc gagttacttt tagcttatgc atgctacttg   4440
ggtgtaatat tgggatctgt tcggaaatca acggatgctc aaccgatttc gacagtaatt   4500
aattaatttg aatcgaatcg gagcctaaaa tgaacccgag tatatctcat aaaattctcg   4560
gtgagaggtc tgtgactgtc agtacaaggt gccttcatta tgccctcaac cttaccatac   4620
ctcactgaat gtagtgtacc tctaaaaatg aaatacagtg ccaaaagcca aggcactgag   4680
ctcgtctaac ggacttgata tacaaccaat taaaacaaat gaaaagaaat acagttcttt   4740
gtatcatttg taacaattac cctgtacaaa ctaaggtatt gaaatcccac aatattccca   4800
aagtccaccc ctttccaaat tgtcatgcct acaactcata taccaagcac taacctacca   4860
aacaccacta aaaccccaca aaatatatct taccgaatat acagtaacaa gctaccacca   4920
cactcgttgg gtgcagtcgc cagcttaaag atatctatcc acatcagcca caactccctt   4980
cctttaataa accgactaca cccttggcta ttgaggttat gagtgaatat actgtagaca   5040
agacactttc aagaagactg tttccaaaac gtaccactgt cctccactac aaacacaccc   5100
```

-continued

```
aatctgcttc ttctagtcaa ggttgctaca ccggtaaatt ataaatcatc atttcattag   5160
cagggcaggg cccttttat agagtcttat acactagcgg accctgccgg tagaccaacc   5220
cgcaggcgcg tcagtttgct ccttccatca atgcgtcgta gaaacgactt actccttctt   5280
gagcagctcc ttgaccttgt tggcaacaag tctccgacct cggaggtgga ggaagagcct   5340
ccgatatcgg cggtagtgat accagcctcg acggactcct tgacggcagc ctcaacagcg   5400
tcaccggcgg gcttcatgtt aagagagaac ttgagcatca tggcggcaga cagaatggtg   5460
gcaatggggt tgaccttctg cttgccgaga tcgggggcag atccgtgaca gggctcgtac   5520
agaccgaacg cctcgttggt gtcgggcaga gaagccagag aggcggaggg cagcagaccc   5580
agagaaccgg ggatgacgga ggcctcgtcg gagatgatat cgccaaacat gttggtggtg   5640
atgatgatac cattcatctt ggagggctgc ttgatgagga tcatggcggc cgagtcgatc   5700
agctggtggt tgagctcgag ctgggggaat tcgtccttga ggactcgagt gacagtcttt   5760
cgccaaagtc gagaggaggc cagcacgttg gccttgtcaa gagaccacac gggaagaggg   5820
gggttgtgct gaagggccag gaaggcggcc attcgggcaa ttcgctcaac ctcaggaacg   5880
gagtaggtct cggtgtcgga agcgacgcca gatccgtcat cctcctttcg ctctccaaag   5940
tagatacctc cgacgagctc tcggacaatg atgaagtcgg tgccctcaac gtttcggatg   6000
ggggagagat cggcgagctt gggcgacagc agctggcagg gtcgcaggtt ggcgtacagg   6060
ttcaggtcct ttcgcagctt gaggagaccc tgctcgggtc gcacgtcggt tcgtccgtcg   6120
ggagtggtcc atacggtgtt ggcagcgcct ccgacagcac cgagcataat agagtcagcc   6180
tttcggcaga tgtcgagagt agcgtcggtg atgggctcgc cctccttctc aatggcagct   6240
cctccaatga gtcggtcctc aaacacaaac tcggtgccgg aggcctcagc aacagacttg   6300
agcaccttga cggcctcggc aatcacctcg gggccacaga agtcgccgcc gagaagaaca   6360
atcttcttgg agtcagtctt ggtcttctta gtttcgggtt ccattgtgga tgtgtgtggt   6420
tgtatgtgtg atgtggtgtg tggagtgaaa atctgtggct ggcaaacgct cttgtatata   6480
tacgcacttt tgcccgtgct atgtggaaga ctaaacctcc gaagattgtg actcaggtag   6540
tgcggtatcg gctagggacc caaaccttgt cgatgccgat agcgctatcg aacgtacccc   6600
agccggccgg gagtatgtcg gaggggacat acgagatcgt caagggtttg tggccaactg   6660
gtatttaaat gtagctaacg gtagcaggcg aactactggt acatacctcc cccggaatat   6720
gtacaggcat aatgcgtatc tgtgggacat gtggtcgttg cgccattatg taagcagcgt   6780
gtactcctct gactgtccat atggtttgct ccatctcacc ctcatcgttt tcattgttca   6840
caggcggcca caaaaaaact gtcttctctc cttctctctt cgccttagtc tactcggacc   6900
agttttagtt tagcttggcg ccactggata aatgagacct caggccttgt gatgaggagg   6960
tcacttatga agcatgttag gaggtgcttg tatggataga gaagcaccca aaataataag   7020
aataataata aaacaggggg cgttgtcatt tcatatcgtg ttttcaccat caatacacct   7080
ccaaacaatg cccttcatgt ggccagcccc aatattgtcc tgtagttcaa ctctatgcag   7140
ctcgtatctt attgagcaag taaaactctg tcagccgata ttgcccgacc cgcgacaagg   7200
gtcaacaagg tggtgtaagg ccttcgcaga agtcaaaact gtgccaaaca aacatctaga   7260
gtctctttgg tgtttctcgc atatatttwa tcggctgtct tacgtatttg cgcctcggta   7320
ccggactaat ttcggatcat ccccaatacg ctttttcttc gcagctgtca acagtgtcca   7380
tgatctatcc acctaaatgg gtcatatgag gcgtataatt tcgtggtgct gataataatt   7440
cccatatatt tgacacaaaa cttccccccc tagacataca tctcacaatc tcacttcttg   7500
```

-continued

```
tgcttctgtc acacatctcc tccagctgac ttcaactcac acctctgccc cagttggtct   7560
acagcggtat aaggtttctc cgcatagagg tgcaccactc ctcccgatac ttgtttgtgt   7620
gacttgtggg tcacgacata tatatctaca cacattgcgc caccctttgg ttcttccagc   7680
acaacaaaaa cacgacacgc taaccatggc caatttactg accgtacacc aaaatttgcc   7740
tgcattaccg gtcgatgcaa cgagtgatga ggttcgcaag aacctgatgg acatgttcag   7800
ggatcgccag gcgttttctg agcatacctg gaaaatgctt ctgtccgttt gccggtcgtg   7860
ggcggcatgg tgcaagttga ataaccggaa atggtttccc gcagaacctg aagatgttcg   7920
cgattatctt ctatatcttc aggcgcgcgg tctggcagta aaaactatcc agcaacattt   7980
gggccagcta aacatgcttc atcgtcggtc cgggctgcca cgaccaagtg acagcaatgc   8040
tgtttcactg gttatgcggc ggatccgaaa agaaaacgtt gatgccggtg aacgtgcaaa   8100
acaggctcta gcgttcgaac gcactgattt cgaccaggtt cgttcactca tggaaaatag   8160
cgatcgctgc caggatatac gtaatctggc atttctgggg attgcttata acaccctgtt   8220
acgtatagcc gaaattgcca ggatcagggt taaagatatc tcacgtactg acggtgggag   8280
aatgttaatc catattggca gaacgaaaac gctggttagc accgcaggtg tagagaaggc   8340
acttagcctg ggggtaacta aactggtcga gcgatggatt tccgtctctg gtgtagctga   8400
tgatccgaat aactacctgt tttgccgggt cagaaaaaat ggtgttgccg cgccatctgc   8460
caccagccag ctatcaactc gcgccctgga agggattttt gaagcaactc atcgattgat   8520
ttacggcgct aaggatgact ctggtcagag atacctggcc tggtctggac acagtgcccg   8580
tgtcggagcc gcgcgagata tggcccgcgc tggagtttca ataccggaga tcatgcaagc   8640
tggtggctgg accaatgtaa atattgtcat gaactatatc cgtaacctgg atagtgaaac   8700
aggggcaatg gtgcgcctgc tggaagatgg cgattaagc                          8739
```

<210> SEQ ID NO 51
<211> LENGTH: 8255
<212> TYPE: DNA
<213> ORGANISM: Artificial Sequence
<220> FEATURE:
<223> OTHER INFORMATION: Plasmid pZUFmEaD8S

<400> SEQUENCE: 51

```
catggtcaag cgacccgctc tgcctctcac cgtggacggt gtcacctacg acgtttctgc     60
ctggctcaac caccatcccg gaggtgccga cattatcgag aactaccgag gtcgggatgc    120
taccgacgtc ttcatggtta tgcactccga gaacgccgtg tccaaactca gacgaatgcc    180
catcatggaa ccttcctctc ccctgactcc aacacctccc aagccaaact ccgacgaacc    240
tcaggaggat ttccgaaagc tgcgagacga gctcattgct gcaggcatgt tcgatgcctc    300
tcccatgtgg tacgcttaca agaccctgtc gactctcgga ctgggtgtcc ttgccgtgct    360
gttgatgacc cagtggcact ggtacctggt tggtgctatc gtcctcggca ttcactttca    420
acagatggga tggctctcgc acgacatttg ccatcaccag ctgttcaagg accgatccat    480
caacaatgcc attggcctgc tcttcggaaa cgtgcttcag ggcttttctg tcacttggtg    540
gaaggaccga cacaacgctc atcactccgc caccaacgtg cagggtcacg atcccgacat    600
cgacaacctg cctctcctgg cgtggtccaa ggaggacgtc gagcgagctg gcccgttttc    660
tcgacggatg atcaagtacc aacagtatta cttctttttc atctgtgccc ttctgcgatt    720
catctggtgc tttcagtcca ttcatactgc cacgggtctc aaggatcgaa gcaatcagta    780
```

-continued

```
ctatcgaaga cagtacgaga aggagtccgt cggtctggca ctccactggg gtctcaaggc    840
cttgttctac tatttctaca tgccctcgtt tctcaccgga ctcatggtgt tctttgtctc    900
cgagctgctt ggtggcttcg gaattgccat cgttgtcttc atgaaccact accctctgga    960
gaagattcag gactccgtgt gggatggtca tggcttctgt gctggacaga ttcacgagac   1020
catgaacgtt cagcgaggcc tcgtcacaga ctggtttttc ggtggcctca actaccagat   1080
cgaacatcac ctgtggccta ctcttcccag acacaacctc accgctgcct ccatcaaagt   1140
ggagcagctg tgcaagaagc acaacctgcc ctaccgatct cctcccatgc tcgaaggtgt   1200
cggcattctt atctcctacc tgggcacctt cgctcgaatg gttgccaagg cagacaaggc   1260
ctaagcggcc gcaagtgtgg atggggaagt gagtgcccgg ttctgtgtgc acaattggca   1320
atccaagatg gatggattca acacagggat atagcgagct acgtggtggt gcgaggatat   1380
agcaacggat atttatgttt gacacttgag aatgtacgat acaagcactg tccaagtaca   1440
atactaaaca tactgtacat actcatactc gtacccgggc aacggtttca cttgagtgca   1500
gtggctagtg ctcttactcg tacagtgtgc aatactgcgt atcatagtct ttgatgtata   1560
tcgtattcat tcatgttagt tgcgtacgag ccggaagcat aaagtgtaaa gcctggggtg   1620
cctaatgagt gagctaactc acattaattg cgttgcgctc actgcccgct ttccagtcgg   1680
gaaacctgtc gtgccagctg cattaatgaa tcggccaacg cgcggggaga ggcggtttgc   1740
gtattgggcg ctcttccgct tcctcgctca ctgactcgct gcgctcggtc gttcggctgc   1800
ggcgagcggt atcagctcac tcaaaggcgg taatacggtt atccacagaa tcaggggata   1860
acgcaggaaa gaacatgtga gcaaaaggcc agcaaaaggc caggaaccgt aaaaaggccg   1920
cgttgctggc gtttttccat aggctccgcc cccctgacga gcatcacaaa aatcgacgct   1980
caagtcagag gtggcgaaac ccgacaggac tataaagata ccaggcgttt ccccctggaa   2040
gctccctcgt gcgctctcct gttccgaccc tgccgcttac cggatacctg tccgcctttc   2100
tcccttcggg aagcgtggcg ctttctcata gctcacgctg taggtatctc agttcggtgt   2160
aggtcgttcg ctccaagctg ggctgtgtgc acgaaccccc cgttcagccc gaccgctgcg   2220
ccttatccgg taactatcgt cttgagtcca acccggtaag acacgactta tcgccactgg   2280
cagcagccac tggtaacagg attagcagag cgaggtatgt aggcggtgct acagagttct   2340
tgaagtggtg gcctaactac ggctacacta gaaggacagt atttggtatc tgcgctctgc   2400
tgaagccagt taccttcgga aaaagagttg gtagctcttg atccggcaaa caaaccaccg   2460
ctggtagcgg tggttttttt gtttgcaagc agcagattac gcgcagaaaa aaaggatctc   2520
aagaagatcc tttgatcttt tctacggggt ctgacgctca gtggaacgaa aactcacgtt   2580
aagggatttt ggtcatgaga ttatcaaaaa ggatcttcac ctagatcctt ttaaattaaa   2640
aatgaagttt taaatcaatc taaagtatat atgagtaaac ttggtctgac agttaccaat   2700
gcttaatcag tgaggcacct atctcagcga tctgtctatt tcgttcatcc atagttgcct   2760
gactccccgt cgtgtagata actacgatac gggagggctt accatctggc cccagtgctg   2820
caatgatacc gcgagaccca cgctcaccgg ctccagattt atcagcaata aaccagccag   2880
ccggaagggc cgagcgcaga agtggtcctg caactttatc cgcctccatc cagtctatta   2940
attgttgccg ggaagctaga gtaagtagtt cgccagttaa tagtttgcgc aacgttgttg   3000
ccattgctac aggcatcgtg gtgtcacgct cgtcgtttgg tatggcttca ttcagctccg   3060
gttcccaacg atcaaggcga gttacatgat cccccatgtt gtgcaaaaaa gcggttagct   3120
ccttcggtcc tccgatcgtt gtcagaagta agttggccgc agtgttatca ctcatggtta   3180
```

-continued

```
tggcagcact gcataattct cttactgtca tgccatccgt aagatgcttt tctgtgactg   3240
gtgagtactc aaccaagtca ttctgagaat agtgtatgcg gcgaccgagt tgctcttgcc   3300
cggcgtcaat acgggataat accgcgccac atagcagaac tttaaaagtg ctcatcattg   3360
gaaaacgttc ttcggggcga aaactctcaa ggatcttacc gctgttgaga tccagttcga   3420
tgtaacccac tcgtgcaccc aactgatctt cagcatcttt tactttcacc agcgtttctg   3480
ggtgagcaaa aacaggaagg caaaatgccg caaaaaaggg aataagggcg acacggaaat   3540
gttgaatact catactcttc ctttttcaat attattgaag catttatcag ggttattgtc   3600
tcatgagcgg atacatattt gaatgtattt agaaaaataa acaaataggg gttccgcgca   3660
catttccccg aaaagtgcca cctgacgcgc cctgtagcgg cgcattaagc gcggcgggtg   3720
tggtggttac gcgcagcgtg accgctacac ttgccagcgc cctagcgccc gctcctttcg   3780
ctttcttccc ttcctttctc gccacgttcg ccggctttcc ccgtcaagct ctaaatcggg   3840
ggctcccttt agggttccga tttagtgctt tacggcacct cgaccccaaa aaacttgatt   3900
agggtgatgg ttcacgtagt gggccatcgc cctgatagac ggtttttcgc cctttgacgt   3960
tggagtccac gttctttaat agtggactct tgttccaaac tggaacaaca ctcaacccta   4020
tctcggtcta ttcttttgat ttataaggga ttttgccgat ttcggcctat tggttaaaaa   4080
atgagctgat ttaacaaaaa tttaacgcga attttaacaa aatattaacg cttacaattt   4140
ccattcgcca ttcaggctgc gcaactgttg ggaagggcga tcggtgcggg cctcttcgct   4200
attacgccag ctggcgaaag ggggatgtgc tgcaaggcga ttaagttggg taacgccagg   4260
gttttcccag tcacgacgtt gtaaaacgac ggccagtgaa ttgtaatacg actcactata   4320
gggcgaattg ggtaccgggc ccccctcga ggtcgatggt gtcgataagc ttgatatcga   4380
attcatgtca cacaaaccga tcttcgcctc aaggaaacct aattctacat ccgagagact   4440
gccgagatcc agtctacact gattaatttt cgggccaata atttaaaaaa atcgtgttat   4500
ataatattat atgtattata tatatacatc atgatgatac tgacagtcat gtcccattgc   4560
taaatagaca gactccatct gccgcctcca actgatgttc tcaatattta aggggtcatc   4620
tcgcattgtt taataataaa cagactccat ctaccgcctc caaatgatgt tctcaaaata   4680
tattgtatga acttattttt attacttagt attattagac aacttacttg ctttatgaaa   4740
aacacttcct atttaggaaa caatttataa tggcagttcg ttcatttaac aatttatgta   4800
gaataaatgt tataaatgcg tatgggaaat cttaaatatg gatagcataa atgatatctg   4860
cattgcctaa ttcgaaatca acagcaacga aaaaaatccc ttgtacaaca taaatagtca   4920
tcgagaaata tcaactatca aagaacagct attcacacgt tactattgag attattattg   4980
gacgagaatc acacactcaa ctgtctttct ctcttctaga aatacaggta caagtatgta   5040
ctattctcat tgttcatact tctagtcatt tcatcccaca tattccttgg atttctctcc   5100
aatgaatgac attctatctt gcaaattcaa caattataat aagatatacc aaagtagcgg   5160
tatagtggca atcaaaaagc ttctctggtg tgcttctcgt atttattttt attctaatga   5220
tccattaaag gtatatattt atttcttgtt atataatcct tttgtttatt acatgggctg   5280
gatacataaa ggtattttga tttaattttt tgcttaaatt caatcccccc tcgttcagtg   5340
tcaactgtaa tggtaggaaa ttaccatact tttgaagaag caaaaaaaat gaaagaaaaa   5400
aaaaatcgta tttccaggtt agacgttccg cagaatctag aatgcggtat gcggtacatt   5460
gttcttcgaa cgtaaaagtt gcgctccctg agatattgta catttttgct tttacaagta   5520
```

-continued

```
caagtacatc gtacaactat gtactactgt tgatgcatcc acaacagttt gttttgtttt   5580
tttttgtttt tttttttct aatgattcat taccgctatg tatacctact tgtacttgta   5640
gtaagccggg ttattggcgt tcaattaatc atagacttat gaatctgcac ggtgtgcgct   5700
gcgagttact tttagcttat gcatgctact tgggtgtaat attgggatct gttcggaaat   5760
caacggatgc tcaatcgatt tcgacagtaa ttaattaagt catacacaag tcagctttct   5820
tcgagcctca tataagtata agtagttcaa cgtattagca ctgtacccag catctccgta   5880
tcgagaaaca caacaacatg ccccattgga cagatcatgc ggatacacag gttgtgcagt   5940
atcatacata ctcgatcaga caggtcgtct gaccatcata caagctgaac aagcgctcca   6000
tacttgcacg ctctctatat acacagttaa attacatatc catagtctaa cctctaacag   6060
ttaatcttct ggtaagcctc ccagccagcc ttctggtatc gcttggcctc ctcaatagga   6120
tctcggttct ggccgtacag acctcggccg acaattatga tatccgttcc ggtagacatg   6180
acatcctcaa cagttcggta ctgctgtccg agagcgtctc ccttgtcgtc aagacccacc   6240
ccgggggtca gaataagcca gtcctcagag tcgcccttag gtcggttctg ggcaatgaag   6300
ccaaccacaa actcggggtc ggatcgggca agctcaatgg tctgcttgga gtactcgcca   6360
gtggccagag agcccttgca agacagctcg gccagcatga gcagacctct ggccagcttc   6420
tcgttgggag aggggactag gaactccttg tactgggagt tctcgtagtc agagacgtcc   6480
tccttcttct gttcagagac agtttcctcg gcaccagctc gcaggccagc aatgattccg   6540
gttccgggta caccgtgggc gttggtgata tcggaccact cggcgattcg gtgacaccgg   6600
tactggtgct tgacagtgtt gccaatatct gcgaactttc tgtcctcgaa caggaagaaa   6660
ccgtgcttaa gagcaagttc cttgaggggg agcacagtgc cggcgtaggt gaagtcgtca   6720
atgatgtcga tatgggtttt gatcatgcac acataaggtc cgaccttatc ggcaagctca   6780
atgagctcct tggtggtggt aacatccaga gaagcacaca ggttggtttt cttggctgcc   6840
acgagcttga gcactcgagc ggcaaaggcg gacttgtgga cgttagctcg agcttcgtag   6900
gagggcattt tggtggtgaa gaggagactg aaataaattt agtctgcaga actttttatc   6960
ggaaccttat ctggggcagt gaagtatatg ttatggtaat agttacgagt tagttgaact   7020
tatagataga ctggactata cggctatcgg tccaaattag aaagaacgtc aatggctctc   7080
tgggcgtcgc ctttgccgac aaaaatgtga tcatgatgaa agccagcaat gacgttgcag   7140
ctgatattgt tgtcggccaa ccgcgccgaa aacgcagctg tcagacccac agcctccaac   7200
gaagaatgta tcgtcaaagt gatccaagca cactcatagt tggagtcgta ctccaaaggc   7260
ggcaatgacg agtcagacag atactcgtcg acgtttaaac agtgtacgca gatctactat   7320
agaggaacat ttaaattgcc ccggagaaga cggccaggcc gcctagatga caaattcaac   7380
aactcacagc tgactttctg ccattgccac tagggggggg ccttttata tggccaagcc   7440
aagctctcca cgtcggttgg gctgcaccca acaataaatg ggtagggttg caccaacaaa   7500
gggatgggat ggggggtaga agatacgagg ataacggggc tcaatggcac aaataagaac   7560
gaatactgcc attaagactc gtgatccagc gactgacacc attgcatcat ctaagggcct   7620
caaaactacc tcggaactgc tgcgctgatc tggacaccac agaggttccg agcactttag   7680
gttgcaccaa atgtcccacc aggtgcaggc agaaaacgct ggaacagcgt gtacagtttg   7740
tcttaacaaa aagtgagggc gctgaggtcg agcagggtgg tgtgacttgt tatagccttt   7800
agagctgcga aagcgcgtat ggatttggct catcaggcca gattgagggt ctgtggacac   7860
atgtcatgtt agtgtacttc aatcgccccc tggatatagc cccgacaata ggccgtggcc   7920
```

-continued

```
tcattttttt gccttccgca catttccatt gctcgatacc cacaccttgc ttctcctgca    7980
cttgccaacc ttaatactgg tttacattga ccaacatctt acaagcgggg ggcttgtcta    8040
gggtatatat aaacagtggc tctcccaatc ggttgccagt ctcttttttc ctttctttcc    8100
ccacagattc gaaatctaaa ctacacatca cagaattccg agccgtgagt atccacgaca    8160
agatcagtgt cgagacgacg cgttttgtgt aatgacacaa tccgaaagtc gctagcaaca    8220
cacactctct acacaaacta acccagctct ggtac                                8255
```

Δ-8 DESATURASES AND THEIR USE IN MAKING POLYUNSATURATED FATTY ACIDS

This application claims the benefit of U.S. Provisional Patent Application No. 60/910,831, filed Apr. 10, 2007, which is incorporated herein in its entirety by reference.

FIELD OF THE INVENTION

This invention is in the field of biotechnology. More specifically, this invention pertains to the identification of polynucleotide sequences encoding Δ8 fatty acid desaturases and the use of these desaturases in making long-chain polyunsaturated fatty acids (PUFAs).

BACKGROUND OF THE INVENTION

Today, a variety of different hosts including plants, algae, fungi, stramenopiles and yeast are being investigated as means for commercial PUFA production. Genetic engineering has demonstrated that the natural abilities of some hosts (even those natively limited to linoleic acid (LA; 18:2 ω-6) or α-linolenic acid (ALA; 18:3 ω-3) fatty acid production) can be substantially altered to result in high-level production of various long-chain ω-3/ω-6 PUFAs. Accordingly, production of arachidonic acid (ARA; 20:4 ω-6), eicosapentaenoic acid (EPA; 20:5 ω-3) and docosahexaenoic acid (DHA; 22:6 ω-3) may require expression of a Δ8 desaturase.

The Δ8 desaturase enzymes identified thus far have the ability to convert both eicosadienoic acid (EDA; 20:2 ω-6) to dihomo-γ-linolenic acid (DGLA; 20:3 ω-6) and eicosatrienoic acid (ETrA; 20:3 ω-3) to eicosatetraenoic acid (ETA; 20:4 ω-3) (wherein ARA are EPA are subsequently synthesized from DGLA and ETA, respectively, following reaction with a Δ5 desaturase, while DHA synthesis requires subsequent expression of an additional $C_{20/22}$ elongase and a Δ4 desaturase).

Based on the role Δ8 desaturase enzymes play in the synthesis of e.g., ARA, EPA and DHA, considerable effort has been made to identify and characterize these enzymes from various sources. Initial efforts have focused on the isolation and characterization of Δ8 desaturases from *Euglena gracilis*; and, several sequence variations within the *Euglena gracilis* Δ8 desaturase have been reported (see, e.g., Wallis et al., *Arch. Biochem. and Biophys.,* 365(2):307-316 (1999); PCT Publication No. WO 2000/34439; U.S. Pat. No. 6,825,017; PCT Publication No. WO 2004/057001). Additionally, commonly owned, co-pending U.S. application Ser. No. 11/166,003 and U.S. Pat. No. 7,256,033 disclose amino acid and nucleic acid sequences for a *Euglena gracilis* Δ8 desaturase. In other work commonly owned, co-pending applications U.S. patent application Ser. No. 11/635,258 and Ser. No. 11/951,697 describe a synthetically engineered mutant Δ8 desaturase, derived from *Euglena gracilis.*

U.S. Publication No. 2005/0273885 discloses amino acid and nucleic acid sequences for a Δ8 desaturase enzyme from *Pavlova salina* and commonly owned and co-pending application U.S. patent application Ser. No. 11/737,772 discloses amino acid and nucleic acid sequences for a Δ8 desaturase enzyme from *Pavlova lutheri* (CCMP459), whereas U.S. patent application Ser. No. 11/876,115 discloses amino acid and nucleic acid sequences for Δ8 desaturase enzymes from *Tetruetreptia pomquetensis* CCMP1491, *Eutreptiella* sp. CCMP389 and *Eutreptiella cf_gymnastica* CCMP1594. Sayanova et al. (*FEBS Lett.,* 580:1946-1952 (2006)) describe the isolation and characterization of a cDNA from the free living soil amoeba *Acanthamoeba castellanii* that, when expressed in *Arabidopsis*, encodes a polypeptide having $C_{20}$ Δ8 desaturase activity.

Despite the disclosures cited above, there is a need for additional genes encoding polypeptides having Δ8 desaturase activity as it is only through genetic variation that a wide variety of host cells may be optimized for PUFA production. Applicants address the stated need herein by reporting the isolation of genes encoding Δ8 fatty acid desaturases from *Euglena anabaena.*

SUMMARY OF THE INVENTION

The present invention relates to new genetic constructs encoding polypeptides having Δ8 desaturase activity, and their use in algae, bacteria, yeast, euglenoids, stramenopiles and fungi for the production of PUFAs. Accordingly the invention provides, a microbial host cell comprising an isolated polynucleotide comprising:

(a) a nucleotide sequence encoding a polypeptide having Δ8 desaturase activity, wherein the polypeptide has at least 80% amino acid identity, based on the Clustal V method of alignment, when compared to an amino acid sequence selected from the group consisting of: SEQ ID NO:21, SEQ ID NO:22, SEQ ID NO:23 and SEQ ID NO:24;

(b) a nucleotide sequence encoding a polypeptide having Δ8 desaturase activity, wherein the nucleotide sequence has at least 80% sequence identity, based on the BLASTN method of alignment, when compared to a nucleotide sequence selected from the group consisting of: SEQ ID NO:17, SEQ ID NO:18, SEQ ID NO:19, SEQ ID NO:20 and SEQ ID NO:39;

(c) a nucleotide sequence encoding a polypeptide having Δ8 desaturase activity, wherein the nucleotide sequence hybridizes under stringent conditions to a nucleotide sequence selected from the group consisting of: SEQ ID NO:17, SEQ ID NO:18, SEQ ID NO:19, SEQ ID NO:20 and SEQ ID NO:39; or (d) a complement of the nucleotide sequence of (a), (b) or (c), wherein the complement and the nucleotide sequence consist of the same number of nucleotides and are 100% complementary.

In another embodiment the invention provides a method for the production of dihomo-γ-linoleic acid comprising:

a) providing a microbial host cell comprising:
   (i) a recombinant nucleotide molecule encoding a Δ8 desaturase polypeptide having at least 80% amino acid identity, based on the Clustal V method of alignment, when compared to a polypeptide having an amino acid sequence selected from the group consisting of: SEQ ID NO:21, SEQ ID NO:22, SEQ ID NO:23 and SEQ ID NO:24; and,
   (ii) a source of eicosadienoic acid;

b) growing the microbial host cell of step (a) under conditions wherein the nucleic acid fragment encoding the Δ8 desaturase polypeptide is expressed and the eicosadienoic acid is converted to dihomo-γ-linoleic acid; and, optionally recovering the dihomo-γ-linoleic acid of step (b).

Similarly the invention provides a method for the production of eicosatetraenoic acid comprising:

a) providing a microbial host cell comprising:
   (i) a recombinant nucleotide molecule encoding a Δ5 desaturase polypeptide having at least 80% amino acid identity, based on the Clustal V method of alignment, when compared to a polypeptide having an amino acid sequence selected from the group consisting of: SEQ ID NO:21, SEQ ID NO:22, SEQ ID NO:23 and SEQ ID NO:24; and, (ii) a source of eicosatrienoic acid;

b) growing the microbial host cell of step (a) under conditions wherein the nucleic acid fragment encoding the Δ8 desaturase polypeptide is expressed and the eicosatrienoic acid is converted to eicosatetraenoic acid; and, c) optionally recovering the eicosatetraenoic acid of step (b).

In another embodiment the invention provides an isolated nucleic acid molecule which encodes a Δ8 desaturase as set forth in SEQ ID NO:39 wherein at least 208 codons are codon-optimized for expression in *Yarrowia* sp.

BRIEF DESCRIPTION OF THE DRAWINGS AND SEQUENCE LISTINGS

FIG. 1 is a representative ω-3 and ω-6 fatty acid biosynthetic pathway providing for the conversion of myristic acid through various intermediates to DHA.

Figure 2:
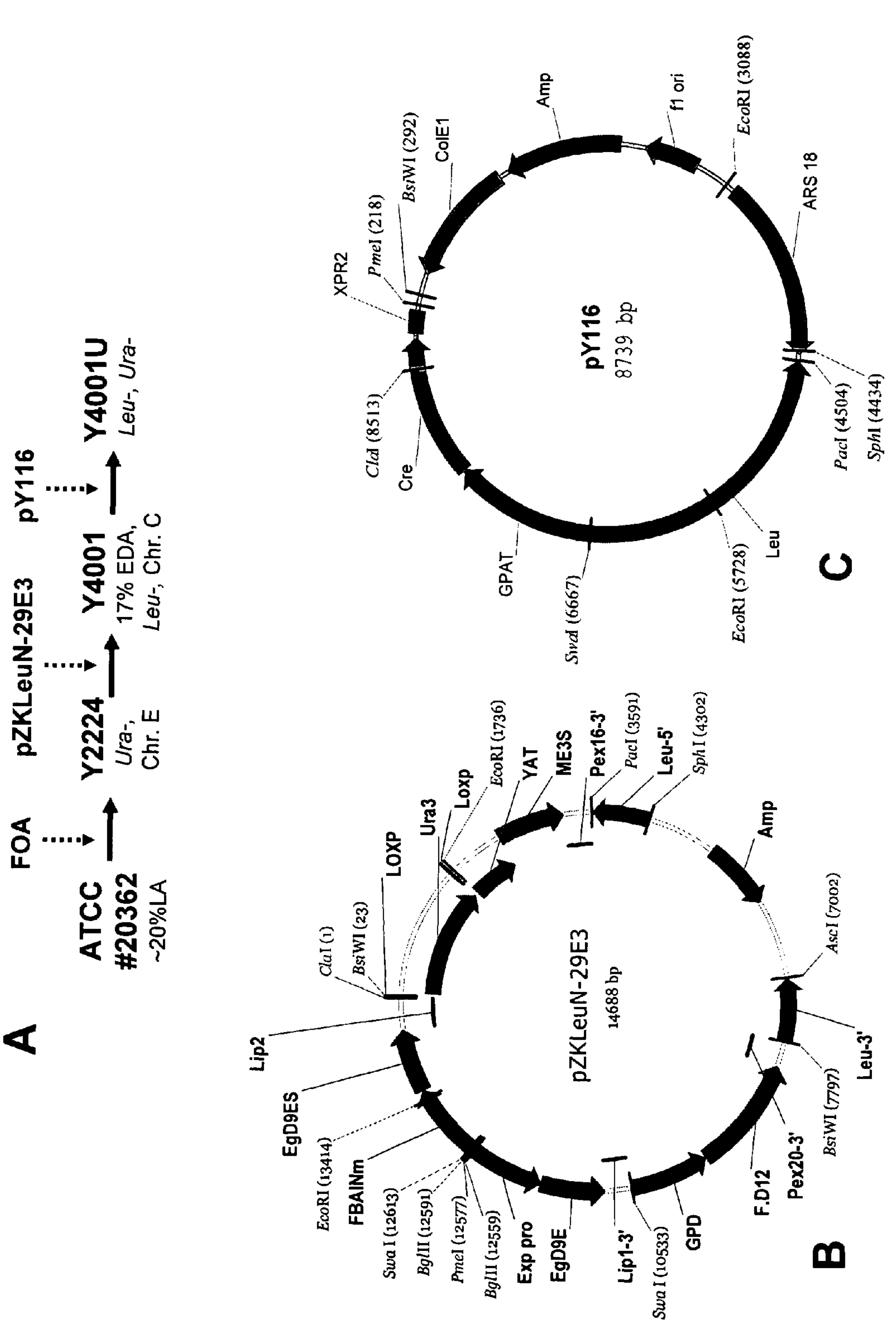

FIG. 2A diagrams the development of *Yarrowia lipolytica* strain Y4001U, producing about 17% EDA in the total lipid fraction. FIG. 2B provides the plasmid map for pZKLeuN-29E3, while FIG. 2C provides the plasmid map for pY116.

Figure 3:
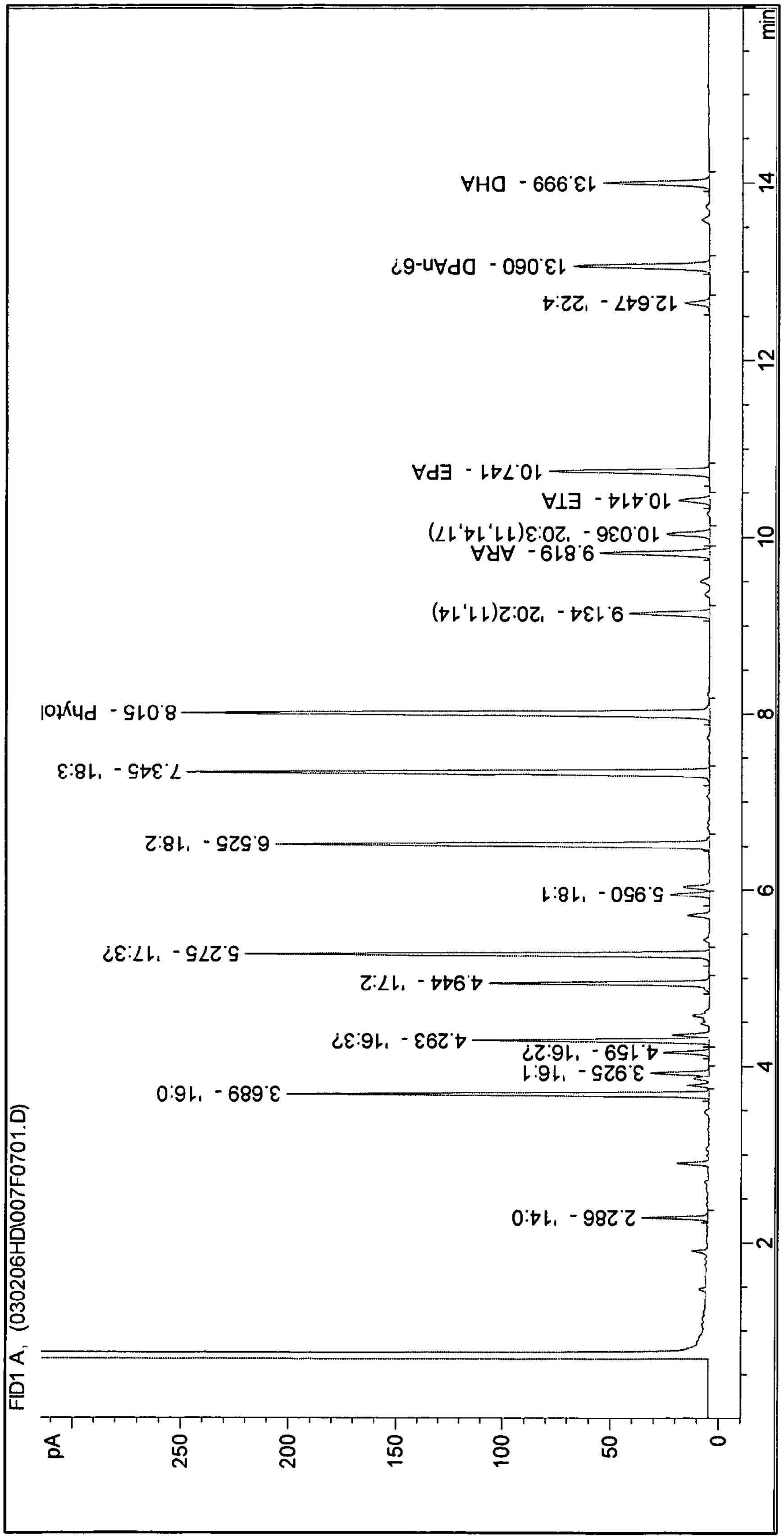

FIG. 3 shows a chromatogram of the lipid profile of an *Euglena anabaena* cell extract as described in Example 1.

FIGS. 4A, 4B and 4C show a Clustal V alignment of the Δ8 desaturase sequences for EaD8Des1 (SEQ ID NO:21), EaD8Des2 (SEQ ID NO:22), EaD8Des3 (SEQ ID NO:23) and EaD8Des4 (SEQ ID NO:24), and a functional variant *Euglena gracilis* Δ8 desaturase amino acid sequence (EgD8; SEQ ID NO:25; described as Eg5 in PCT Application No. WO 2006/012325).

Figure 5:
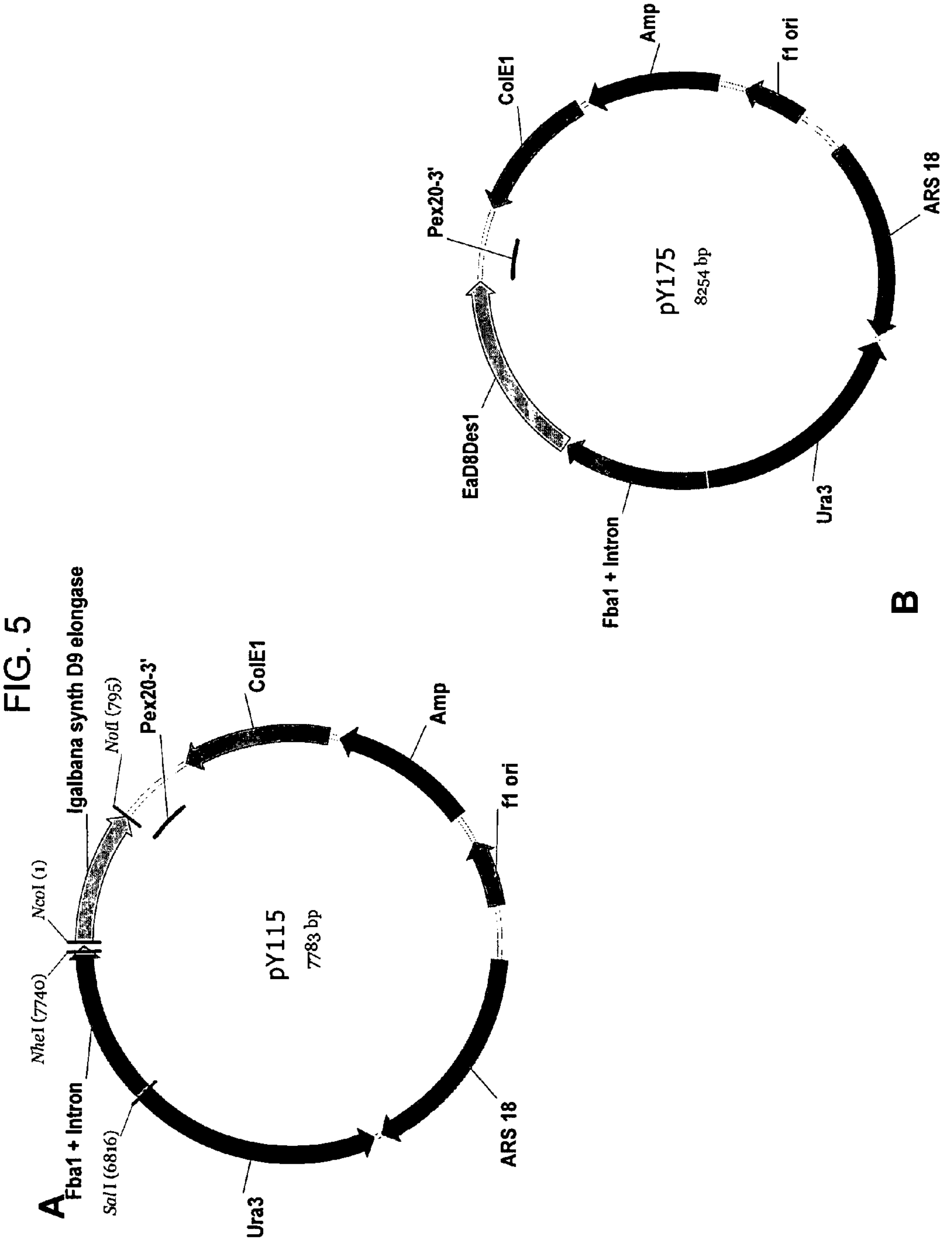

FIG. 5 provides plasmid maps for the following: (A) pY115 (SEQ ID NO:34); and, (B) pY175 (SEQ ID NO:35).

FIG. 6 provides the fatty acid profiles for *Yarrowia lipolytica* expressing pY175, pY176, pY177 and pY178 (see Example 5).

Figure 7A:
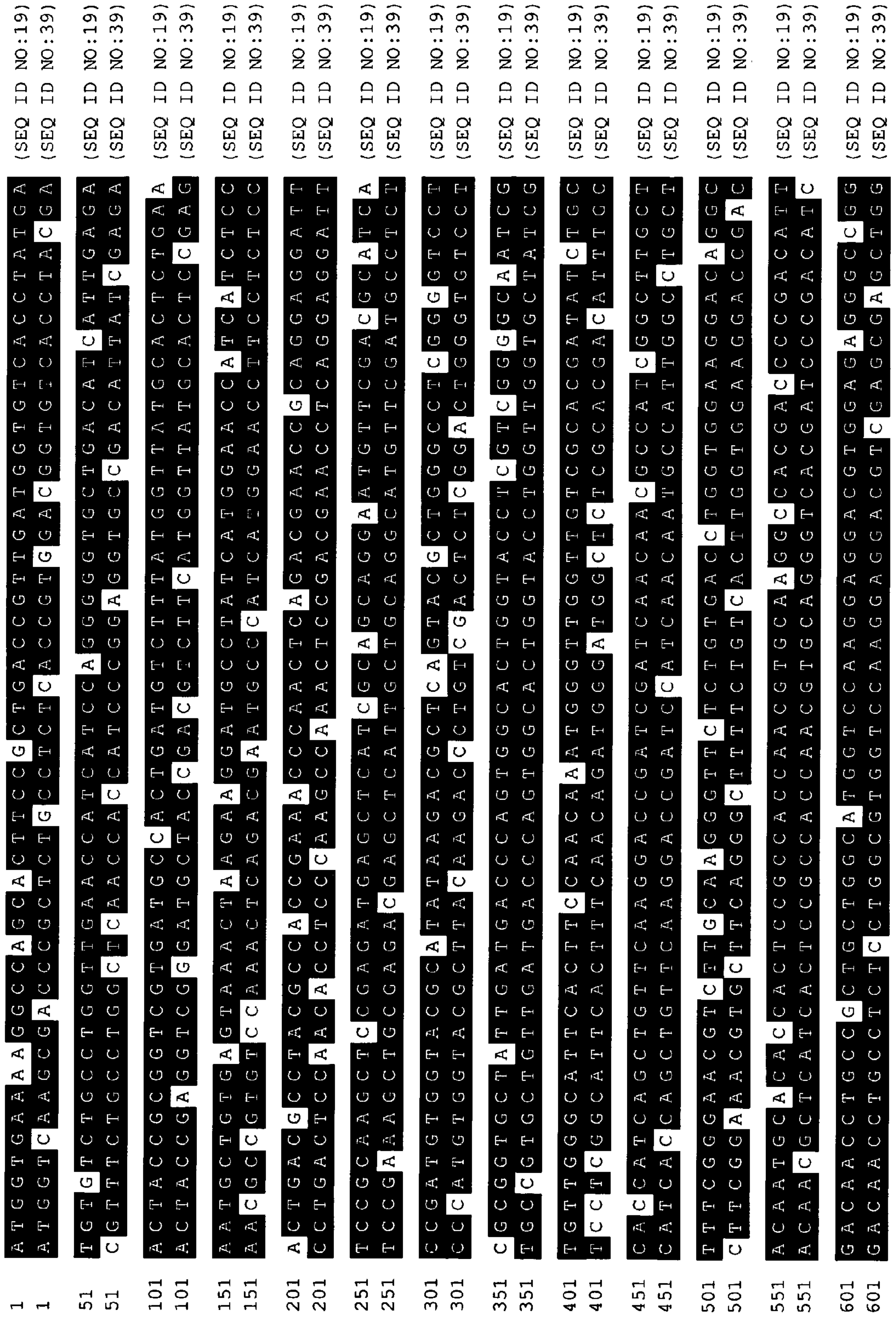
Figure 7B:
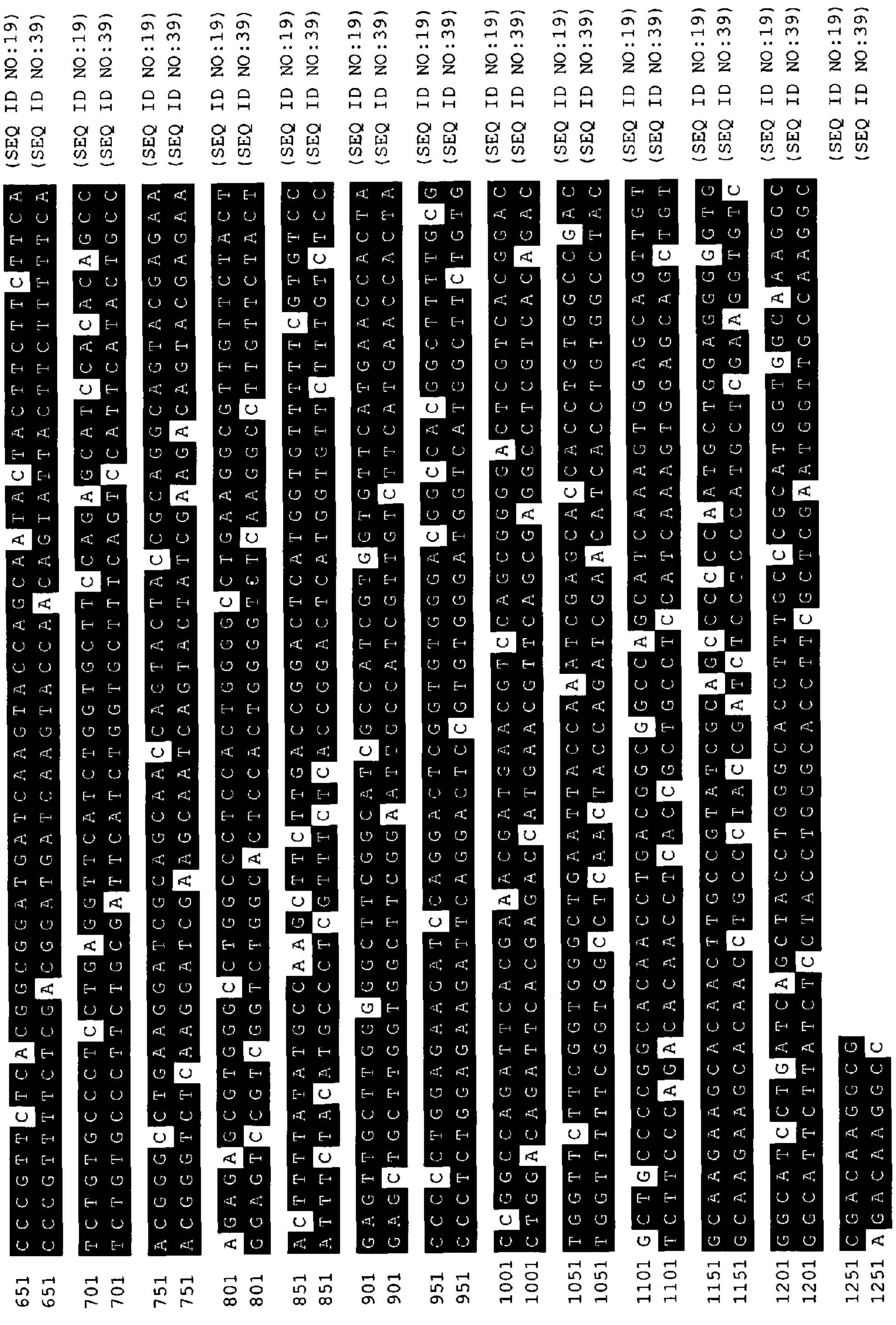

FIGS. 7A and 7B show a comparison of the nucleotide sequences of EaD8Des3 (SEQ ID NO:19) and EaD8S (SEQ ID NO:39).

Figure 8:
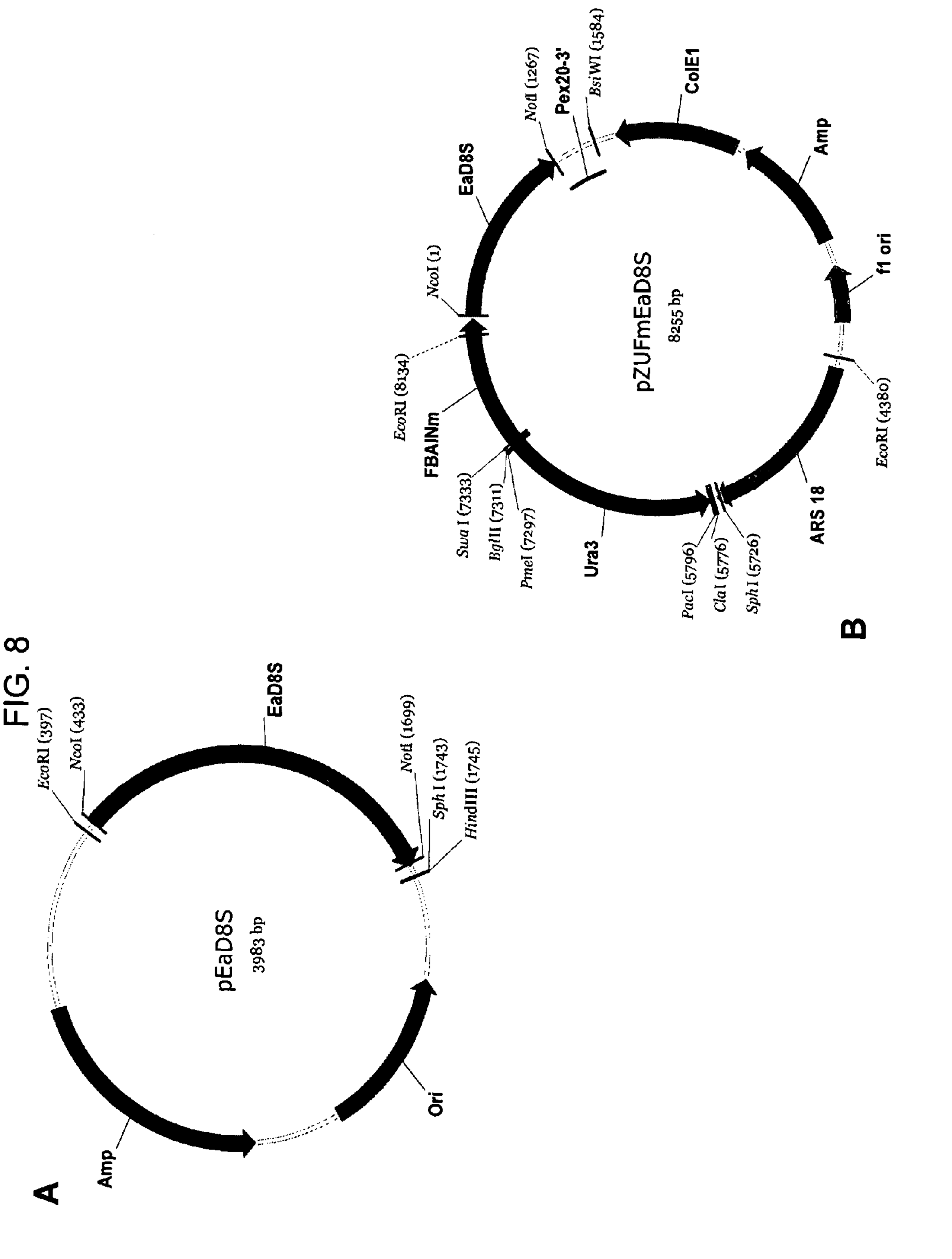

FIG. 8 provides plasmid maps for the following: (A) pEaD8S (SEQ ID NO:41); and, (B) pZUFmEaD8S (SEQ ID NO:51).

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1, 2, 10, 11, 13-25, and 28-51 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Euglena anabaena* Δ8 desaturase partial sequence | 1 (604 bp) | — |
| *Euglena gracilis* Δ8 desaturase CDS ("Eg5") | 2 (1263 bp) | — |
| Plasmid pHD23-1 | 10 (4116 bp) | — |
| *Euglena gracilis* Δ8 desaturase (NCBI Accession No. AAD45877) | — | 11 (419 AA) |
| Plasmid pLF118-1 | 13 (4363 bp) | — |
| Plasmid pLF118-2 | 14 (4307 bp) | — |
| Plasmid pLF118-3 | 15 (4307 bp) | — |
| Plasmid pLF118-4 | 16 (4297 bp) | — |
| *Euglena anabaena* Δ8 desaturase 1 coding sequence ("EaD8Des1") | 17 (1260 bp) | 21 (420 AA) |
| *Euglena anabaena* Δ8 desaturase 2 coding sequence ("EaD8Des2") | 18 (1260 bp) | 22 (420 AA) |
| *Euglena anabaena* Δ8 desaturase 3 coding sequence ("EaD8Des3") | 19 (1260 bp) | 23 (420 AA) |
| *Euglena anabaena* Δ8 desaturase 4 coding sequence ("EaD8Des4") | 20 (1260 bp) | 24 (420 AA) |
| *Euglena gracilis* Δ8 desaturase ("EgD8") (U.S. Pat. No. 7,256,033) | — | 25 (421 AA) |
| Plasmid pLF120-1 | 28 (4794 bp) | — |
| Plasmid pLF120-2 | 29 (4794 bp) | — |
| Plasmid pLF120-3 | 30 (4794 bp) | — |
| Plasmid pLF120-4 | 31 (4794 bp) | — |
| plasmid pDMW263 | 32 (9472 bp) | — |
| plasmid pDMW237 | 33 (7879 bp) | — |
| plasmid pY115 | 34 (7783 bp) | — |
| plasmid pY175 | 35 (8254 bp) | — |
| plasmid pY176 | 36 (8254 bp) | — |
| plasmid pY177 | 37 (8254 bp) | — |
| plasmid pY178 | 38 (8254 bp) | — |
| Synthetic Δ8 desaturase, derived from *Euglena anabaena*, codon-optimized for expression in *Yarrowia lipolytica* ("EaD8S") | 39 (1260 bp) | 40 (420 AA) |
| Plasmid pEaD8S | 41 (3983 bp) | — |
| Plasmid pZKLeuN-29E3 | 42 (14,688 bp) | — |
| *Fusarium moniliforme* Δ12 desaturase ("FmD12") | 43 (1434 bp) | 44 (477 AA) |
| Synthetic Δ9 elongase derived from *Euglena gracilis*, codon-optimized for expression in *Yarrowia lipolytica* ("EgD9eS") | 45 (777 bp) | 46 (258 AA) |
| *Escherichia coli* LoxP recombination site, recognized by a Cre recombinase enzyme | 47 (34 bp) | — |
| Synthetic $C_{16/18}$ elongase derived from *Mortierella alpina* ELO3, codon-optimized for expression in *Yarrowia lipolytica* ("ME3S") | 48 (828 bp) | 49 (275 AA) |
| Plasmid pY116 | 50 (8739 bp) | — |
| Plasmid pZUFmEaD8S | 51 (8255 bp) | — |

SEQ ID NO:3 is the nucleotide sequence of the vector-specific primer pDonor222Eg5-1.

SEQ ID NOs:4-7 correspond to degenerate primers D8DEG3-1, D8DEG3-2, D8DEG3-3 and D8DEG3-4, respectively, used to amplify a portion of the Δ8 desaturase genes from Euglena anabaena UTEX 373.

SEQ ID NOs:8 and 9 correspond to the T7 primer and primer M13-28Rev, respectively, used for sequencing a partial putative Δ8 desaturase cDNA fragment.

SEQ ID NO:12 is the nucleotide sequence of primer EaD8seq-1, used for full insert sequencing of eug1c Δ8 desaturase clones.

SEQ ID NOs:26 and 27 correspond to primers EaD8-5 and EaD8-3, respectively, used to amplify the EaD8Des1, EaD8Des2, EaD8Des3 and EaD8Des4 coding sequences.

DETAILED DESCRIPTION OF THE INVENTION

New *Euglena anabaena* Δ8 desaturase enzymes and genes encoding the same that may be used for the manipulation of biochemical pathways for the production of healthful PUFAs are disclosed herein. PUFAs, or derivatives thereof, are used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Definitions

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in U.S. Pat. No. 7,238,482.

Fatty acids are described herein by a simple notation system of "X:Y", where X is the total number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the remainder of the specification, and each compounds' chemical name.

TABLE 2

Nomenclature of Polyunsaturated Fatty Acids and Precursors

| Common Name | Abbreviation | Chemical Name | Shorthand Notation |
|---|---|---|---|
| Myristic | — | tetradecanoic | 14:0 |
| Palmitic | PA or Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA or ERA | cis-11,14,17-eicosatrienoic | 20:3 ω-3 |
| Eicosatetraenoic | ETA | cis-8,11,14,17-eicosatetraenoic | 20:4 ω-3 |
| Juniperonic | JUP | cis-5,11,14,17-eicosatrienoic | 20:4b ω-3 |
| Docosatrienoic | DRA | cis-10,13,16-docosatrienoic | 22:3 ω-6 |
| Docosatetraenoic | DTA | cis-7,10,13,16-docosatetraenoic | 22:4 ω-6 |
| Docosapentaenoic | DPAn-6 | cis-4,7,10,13,16-docosapentaenoic | 22:5 ω-6 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature (e.g., see PCT Publication No. WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a Δ9 elongase, a $C_{14/16}$ elongase, a $C_{16/18}$ elongase, a $C_{18/20}$ elongase, a $C_{20/22}$ elongase, a Δ4 desaturase, a Δ5 desaturase, a Δ6 desaturase, a Δ12 desaturase, a Δ15 desaturase, a Δ17 desaturase, a Δ9 desaturase and/or a Δ8 desaturase.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, ω-6 fatty acids.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the PUFA biosynthetic pathway enzyme genes are required, as a number of fatty acid products will only require the expression of a subset of the genes of this pathway.

The term "Δ6 desaturase/Δ6 elongase pathway" will refer to a PUFA biosynthetic pathway that minimally includes at least one Δ6 desaturase and at least one $C_{18/20}$ elongase (also referred to as a Δ6 elongase), thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "Δ9 elongase/Δ8 desaturase pathway" will refer to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the Δ9 elongase/Δ8 desaturase pathway, sciadonic acid (SCI) and juniperonic acid (JUP) also can be produced by the action of a Δ5 desaturase on either EDA or ETrA, respectively. They are considered to be "by-product fatty acids" since neither can be further converted to EPA by the action of other metabolic pathway enzymes.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ8 desaturases that desaturate a fatty acid between the eighth and ninth carbon atom numbered from the carboxyl-terminal end of the molecule and that can, for example, catalyze the conversion of EDA to DGLA and/or ETrA to ETA. Other fatty acid desaturases include, for example: (1) Δ5 desaturases that catalyze the conversion of DGLA to ARA and/or ETA to EPA; (2) Δ6 desaturases that catalyze the conversion of LA to GLA and/or ALA to STA; (3) Δ4 desaturases that catalyze the conversion of DPA to DHA and/or DTA to DPAn-6; (4) Δ12 desaturases that catalyze the conversion of oleic acid to LA; (5) Δ15 desaturases that catalyze the conversion of LA to ALA and/or GLA to STA; (6) Δ17 desaturases that catalyze the conversion of ARA to EPA and/or DGLA to ETA; and, (7) Δ9 desaturases that catalyze the conversion of palmitic acid to palmitoleic acid (16:1) and/or stearic acid to oleic acid (18:1). In the art, Δ15 and Δ17 desaturases are also occasionally referred to as "omega-3 desaturases", "w-3 desaturases" and/or "ω-3 desaturases", based on their ability to convert ω-6 fatty acids into their ω-3 counterparts (e.g., conversion of LA into ALA and ARA into EPA, respectively). In some embodiments, it may be most desirable to empirically determine the specificity of a particular fatty acid desaturase by transforming a suitable host with the gene for the fatty acid desaturase and determining its effect on the fatty acid profile of the host.

The term "EaD8Des1" refers to a Δ8 desaturase enzyme (SEQ ID NO:21) isolated from *Euglena anabaena*, encoded by SEQ ID NO:17 herein. The term "EaD8Des2" refers to a Δ8 desaturase enzyme (SEQ ID NO:22) isolated from *E. anabaena*, encoded by SEQ ID NO:18 herein. Likewise, the term "EaD8Des3" refers to a Δ8 desaturase enzyme (SEQ ID NO:23) isolated from *E. anabaena*, encoded by SEQ ID NO:19 herein. The term "EaD8Des4" refers to a Δ8 desaturase enzyme (SEQ ID NO:24) isolated from *E. anabaena*, encoded by SEQ ID NO:20 herein. Similarly, the term "EaD8S" refers to a synthetic Δ8 desaturase derived from *E. anabaena* that is codon-optimized for expression in *Yarrowia lipolytica* (i.e., SEQ ID NOs:39 and 40).

The term "EgD8" refers to a Δ8 desaturase enzyme (encoded by the nucleotide sequence set forth as SEQ ID NO:2) isolated from *Euglena gracilis*. EgD8 is 100% identical and functionally equivalent to "Eg5", as described in PCT Publication Nos. WO 2006/012325 and WO 2006/012326 (i.e., SEQ ID NO:2 of U.S. Pat. No. 7,256,033).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in U.S. Patent Publication No. 2005/0132442. Examples of reactions catalyzed by elongase systems are the conversion of GLA to DGLA, STA to ETA, LA to EDA, ALA to ETrA, ARA to DTA and EPA to DPA.

In general, the substrate selectivity of elongases is somewhat broad but segregated by both chain length and the degree of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., ARA, EPA). Similarily, a "Δ9 elongase" is able to catalyze the conversion of LA to EDA and/or ALA to ETrA. It is important to note that some elongases have broad specificity and thus a single enzyme may be capable of catalyzing several elongase reactions (e.g., thereby acting as both a $C_{16/18}$ elongase and a $C_{18/20}$ elongase). It may be desirable to empirically determine the specificity of a fatty acid elongase by transforming a suitable host with the gene for the fatty acid elongase and determining its effect on the fatty acid profile of the host.

The term "oleaginous" refers to those organisms that tend to store their energy source in the form of lipid (Weete, In: Fungal Lipid Biochemistry, 2$^{nd}$ Ed., Plenum, 1980). Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil.

The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*. Preferred for use in the present invention are oleaginous strains of *Yarrowia lipolytica*.

The term "Euglenophyceae" refers to a group of unicellular colorless or photosynthetic flagellates ("euglenoids") found living in freshwater, marine, soil and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and refer to a polymer of RNA or DNA that is single- or double-stranded, optionally containing synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the important factors being the ionic strength and temperature of the final wash solution. For DNA-DNA hybrids, the $T_m$ can be approximated from the equation of Meinkoth et al., *Anal. Biochem.,* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); and, low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS,* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant euglenoid polypeptides as set forth in SEQ ID NOs:21, 22, 23 and 24. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". It is further recognized that since in most cases the exact boundaries of regulatory sequences have not been completely defined, DNA fragments of some variation may have identical promoter activity.

A promoter sequence may consist of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter.

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.,* 3:225-236 (1995)).

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA derived from the nucleic acid fragments of the invention. Expression may also refer to translation of mRNA into a protein (either precursor or mature).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: (1) a promoter sequence; (2) a coding sequence (i.e., ORF); and, (3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

A "recombinant DNA construct" (also referred to interchangeably herein as a "expression construct" and "construct") comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.,* 4:2411-2418 (1985); De Almeida et al., *Mol. Gen. Genetics,* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "introduced" means providing a nucleic acid (e.g., expression cassette) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct or expression cassette) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms or "recombinant" or "transformed" organisms.

As used herein, "transgenic" refers to a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression cassette. Transgenic is used herein to include any cell or cell line, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by naturally occurring events such as random cross-fertilization, non-recombinant viral infection, non-recombinant bacterial transformation, non-recombinant transposition, or spontaneous mutation.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987). Transformation methods are well known to those skilled in the art and are described infra. *An Overview: Microbial Biosynthesis Of Fatty Acids And Triacylglycerols*

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in U.S. Pat. No. 7,238,482. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and, (4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ9 elongase/Δ8 desaturase pathway" and LA as substrate, long chain ω-6 fatty acids are formed as follows: (1) LA is converted to EDA by a Δ9 elongase; (2) EDA is converted to DGLA by a Δ8 desaturase; (3) DGLA is converted to ARA by a Δ5 desaturase; (4) ARA is converted to DTA by a $C_{20/22}$ elongase; and, (5) DTA is converted to DPAn-6 by a Δ4 desaturase. Alternatively, the "Δ9 elongase/Δ8 desaturase pathway" can use ALA as substrate to produce long chain ω-3 fatty acids as follows: (1) LA is converted to ALA, the first of the ω-3 fatty acids, by a Δ15 desaturase; (2) ALA is converted to ETrA by a Δ9 elongase; (3) ETrA is converted to ETA by a Δ8 desaturase; (4) ETA is converted to EPA by a Δ5 desaturase; (5) EPA is converted to DPA by a $C_{20/22}$ elongase; and, (6) DPA is converted to DHA by a Δ4 desaturase. Optionally, ω-6 fatty acids may be converted to ω-3 fatty acids; for example, ALA is produced from LA by Δ15 desaturase activity; ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase (i.e., the "Δ6 desaturase/Δ6 elongase pathway"). More specifically, LA and ALA may be converted to GLA and STA, respectively, by a Δ6 desaturase; then, a $C_{18/20}$ elongase converts GLA to DGLA and/or STA to ETA. Downstream PUFAs are subsequently formed as described above.

It is contemplated that the particular functionalities required to be introduced into a specific host organism for production of ω-3/ω-6 fatty acids will depend on the host cell (and its native PUFA profile and/or desaturase/elongase profile), the availability of substrate, and the desired end product(s). For example, expression of the Δ9 elongase/Δ8 desaturase pathway may be preferred in some embodiments, as opposed to expression of the Δ6 desaturase/Δ6 elongase pathway, since PUFAs produced via the former pathway are devoid of GLA and/or STA.

One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; (4) co-factors required by the polypeptide; and/or, (5) whether the polypeptide was modified after its production (e.g., by a kinase or a prenyltransferase). The expressed polypeptide preferably has parameters compatible with the biochemical environment of its location in the host cell (see U.S. Pat. No. 7,238,482).

It will also be useful to consider the conversion efficiency of each particular desaturase and/or elongase. Since each enzyme rarely functions with 100% efficiency to convert substrate to product, the final lipid profile of unpurified oils produced in a host cell will typically be a mixture of various PUFAs consisting of the desired ω-3/ω-6 fatty acid, as well as various upstream intermediary PUFAs. Thus, each enzyme's conversion efficiency must be considered when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Δ8 Desaturases

In the present invention, nucleotide sequences encoding Δ8 desaturases have been isolated from *Euglena anabaena*, as summarized below in Table 3.

TABLE 3

Summary Of *Euglena anabaena* Δ8 Desaturases

| Abbreviation | Nucleotide SEQ ID NO | Amino Acid SEQ ID NO |
|---|---|---|
| EaD8Des1 | 17 | 21 |
| EaD8Des2 | 18 | 22 |
| EaD8Des3 | 19 | 23 |
| EaD8Des4 | 20 | 24 |
| EaD8S | 39 | 40 |

*Note:
SEQ ID NO: 40 is identical in sequence to SEQ ID NO: 23.

Thus, the present invention concerns an isolated polynucleotide comprising:

(a) a nucleotide sequence encoding a polypeptide having Δ8 desaturase activity, wherein the polypeptide has at least 80% amino acid identity, based on the Clustal V method of alignment, when compared to an amino acid sequence as set forth in SEQ ID NO:21, SEQ ID NO:22, SEQ ID NO:23 or SEQ ID NO:24;

(b) a nucleotide sequence encoding a polypeptide having Δ8 desaturase activity, wherein the nucleotide sequence has at least 80% sequence identity, based on the BLASTN method of alignment, when compared to a nucleotide sequence as set forth in SEQ ID NO:17, SEQ ID NO:18, SEQ ID NO:19, SEQ ID NO:20 or SEQ ID NO:39; or, (c) a complement of the nucleotide sequence of (a) or (b), wherein the complement and the nucleotide sequence consist of the same number of nucleotides and are 100% complementary, and host cells comprising the same.

In still another aspect, the invention concerns an isolated polynucleotide comprising a nucleotide sequence encoding a polypeptide having Δ8 desaturase activity, wherein the nucleotide sequence has at least 90% sequence identity, based on the BLASTN method of alignment, when compared to a nucleotide sequence as set forth in SEQ ID NO:17, SEQ ID NO:18, SEQ ID NO:19, SEQ ID NO:20 or SEQ ID NO:39.

More preferred amino acid fragments that are at least about 80%-90% identical are particularly suitable and those sequences that are at least about 90%-95% identical are most preferred. Similarly, preferred Δ8 desaturase encoding nucleic acid sequences corresponding to the instant ORFs are those encoding active proteins and which are at least about 80%-90% identical; those sequences that are at least about 90%-95% identical are most preferred.

In alternate embodiments, the instant EaD8Des1, EaD8Des2, EaD8Des3 and/or EaD8Des4 desaturase sequences can be codon-optimized for expression in a particular host organism. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In one embodiment of the invention, EaD8Des3 (SEQ ID NO:19) was codon-optimized for expression in *Yarrowia lipolytica*. This was possible based on previous determination of the *Y. lipolytica* codon usage profile, identification of those codons that were preferred, and determination of the consensus sequence around the 'ATG' initiation codon (see U.S. Pat. No. 7,238,482 and U.S. Pat. No. 7,125,672, incorporated herein by reference). The resultant synthetic gene is referred to as EaD8S (SEQ ID NO:39). The protein sequence encoded by the codon-optimized Δ8 desaturase gene (i.e., SEQ ID NO:40) is identical to that of the wildtype protein sequence (i.e., SEQ ID NO:23). Similar techniques could be utilized to produce a synthetic Δ8 desaturase derived from EaD8Des1, EaD8Des2 and/or EaD8Des4 for expression in *Y. lipolytica*.

One skilled in the art would be able to use the teachings herein to create various other codon-optimized Δ8 desaturase proteins suitable for optimal expression in alternate hosts, based on the wildtype EaD8Des1, EaD8Des2, EaD8Des3 and/or EaD8Des4 sequences. Accordingly, the instant invention relates to any codon-optimized Δ8 desaturase protein that is derived from the wildtype nucleotide sequences of EaD8Des1 (SEQ ID NO:17), EaD8Des2 (SEQ ID NO:18), EaD8Des3 (SEQ ID NO:19) or EaD8Des4 (SEQ ID NO:20). This includes, but is not limited to, the nucleotide sequence set forth in SEQ ID NO:39, which encodes a synthetic Δ8 desaturase protein (i.e., EaD8S) that was codon-optimized for expression in *Yarrowia lipolytica*. In alternate embodiments, it may be desirable to modify a portion of the codons encoding EaD8Des1, EaD8Des2, EaD8Des3 and/or EaD8Des4 to enhance expression of the gene in a host organism including, but not limited to, a plant or plant part.

Identification and Isolation of Homologs

Any of the instant desaturase sequences (i.e., EaD8Des1, EaD8Des2, EaD8Des3, EaD8Des4, EaD8S) or portions thereof may be used to search for Δ8 desaturase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ8 desaturase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ8 desaturase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., *Proc. Acad. Sci. U.S.A.,* 82:1074 (1985); or strand displacement amplification (SDA), Walker et al., *Proc. Natl. Acad. Sci. U.S.A.,* 89:392 (1992)]; and, (3) methods of library construction and screening by complementation.

For example, genes encoding similar proteins or polypeptides to the Δ8 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing DGLA and/or ETA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, V A; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl Acad. Sci. U.S.A.,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Natl Acad. Sci. U.S.A.,* 86:5673 (1989); Loh et al., *Science,* 243:217 (1989)).

In other embodiments, any of the Δ8 desaturase nucleic acid fragments described herein (or any homologs identified thereof) may be used for creation of new and/or improved fatty acid desaturases. As is well known in the art, in vitro mutagenesis and selection, chemical mutagenesis, "gene shuffling" methods or other means can be employed to obtain mutations of naturally occurring desaturase genes (wherein such mutations may include deletions, insertions and point mutations, or combinations thereof). This would permit production of a polypeptide having desaturase activity, respectively, in vivo with more desirable physical and kinetic parameters for function in the host cell such as a longer half-life or a higher rate of production of a desired PUFA. If desired, the regions of a polypeptide of interest (i.e., a Δ8 desaturase) important for enzymatic activity can be determined through routine mutagenesis, expression of the resulting mutant polypeptides and determination of their activities. An overview of these techniques is described in U.S. Pat. No. 7,238,482. All such mutant proteins and nucleotide sequences encoding them that are derived from EaD8Des1, EaD8Des2, EaD8Des3, EaD8Des4 and EaD8S are within the scope of the present invention.

Alternatively, improved fatty acids may be synthesized by domain swapping, wherein a functional domain from any of the Δ8 desaturase nucleic acid fragments described herein are exchanged with a functional domain in an alternate desaturase gene to thereby result in a novel protein. As used herein, "domain" or "functional domain" refer to nucleic acid sequence(s) that are capable of eliciting a biological response in plants or yeast.

Methods for Production of Various Omega-3 and/or Omega-6 Fatty Acids

It is expected that introduction of chimeric genes encoding the Δ8 desaturases described herein (i.e., EaD8Des1, EaD8Des2, EaD8Des3, EaD8Des4, EaD8S or other mutant enzymes, codon-optimized enzymes or homologs thereof), under the control of the appropriate promoters will result in increased production of DGLA and/or ETA in the transformed host organism. As such, the present invention encompasses a method for the direct production of PUFAs comprising exposing a fatty acid substrate (i.e., EDA and/or ETrA) to the desaturase enzymes described herein (e.g., EaD8Des1, EaD8Des2, EaD8Des3, EaD8Des4 or EaD8S), such that the substrate is converted to the desired fatty acid product (i.e., DGLA and/or ETA, respectively).

More specifically, it is an object of the present invention to provide a method for the production of DGLA in a microbial host cell (e.g., yeast, algae, bacteria, euglenoids, stramenopiles and fungi), wherein the microbial host cell comprises:

a) a recombinant nucleotide molecule encoding a Δ8 desaturase polypeptide having at least 80% amino acid identity, based on the Clustal V method of alignment, when compared to a polypeptide having an amino acid sequence selected from the group consisting of: SEQ ID NO:21, SEQ ID NO:22, SEQ ID NO:23 and SEQ ID NO:24; and, b) a source of EDA;

wherein the microbial host cell is grown under conditions such that the nucleic acid fragment encoding the Δ8 desaturase is expressed and the EDA is converted to DGLA, and wherein the DGLA is optionally recovered.

In alternate embodiments of the present invention, the Δ8 desaturase may be used for the conversion of ETrA to ETA. Accordingly the invention provides a method for the production of ETA, wherein the microbial host cell comprises:

a) a recombinant nucleotide molecule encoding a Δ8 desaturase polypeptide having at least 80% amino acid identity, based on the Clustal V method of alignment, when compared to a polypeptide having an amino acid sequence selected from the group consisting of: SEQ ID NO:21, SEQ ID NO:22, SEQ ID NO:23 and SEQ ID NO:24; and, b) a source of ETrA;

wherein the microbial host cell is grown under conditions such that the nucleic acid fragment encoding the Δ8 desaturase is expressed and the ETrA is converted to ETA, and wherein the ETA is optionally recovered.

Alternatively, each Δ8 desaturase gene and its corresponding enzyme product described herein can be used indirectly for the production of various ω-6 and ω-3 PUFAs (see FIG. 1 and U.S. Pat. No. 7,238,482). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ8 desaturases described herein (i.e., EaD8Des1, EaD8Des2, EaD8Des3, EaD8Des4, EaD8S or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ8 desaturases, Δ15 desaturases, Δ9 desaturases, Δ12 desaturases, $C_{14/16}$ elongases, $C_{16/18}$ elongases, Δ9 elongases, Δ5 desaturases, Δ4 desaturases, $C_{20/22}$ elongases) to result in higher levels of production of longer-chain ω-3/ω-6 fatty acids (e.g., ARA, EPA, DTA, DPAn-6, DPA and/or DHA).

In preferred embodiments, the Δ8 desaturases of the present invention will minimally be expressed in conjunction with a Δ9 elongase (e.g., from *Isochrysis galbana* [PCT Publication No. WO 2002/077213]; from *Euglena gracilis* [PCT Publication No. WO 2007/061845]; and from *Eutreptiella* sp. CCMP389 [PCT Publication No. WO 2007/061742]. However, the particular genes included within a particular expression cassette will depend on the host cell (and its PUFA profile and/or desaturase/elongase profile), the availability of substrate and the desired end product(s).

In some embodiments, it may be useful to express more than one Δ8 desaturase (i.e., the same or different Δ8 desaturase), to minimize by-product fatty acids. The relative abundance of by-product fatty acids could be decreased by increasing total Δ8 desaturase activity. One approach to minimize by-product fatty acids would be to express more than one Δ8 desaturase. For instance, the presence of sciadonic acid (SCI) and/or juniperonic acid (JUP) [commonly found in the seed lipids of gymnosperms (Wolff et al., *Lipids,* 35(1): 1-22 (2000)), such as those in the Pinaceae family (pine)] might be considered by-product fatty acids of a Δ6 desaturase/Δ6 elongase pathway or Δ9 elongase/Δ8 desaturase pathway. Although these fatty acids are considered to have various health-enhancing properties themselves (Nakane et al., *Biol. Pharm. Bull.,* 23: 758-761 (2000)), their presence as by-product fatty acids in an engineered PUFA pathway, such as in an oilseed crop, may not be desirable depending on the application.

Occasionally, a Δ6 elongase may elongate fatty acids other than the intended fatty acid. For instance, Δ6 elongases generally convert GLA to DGLA but some Δ6 elongases may also convert unintended substrates such as LA or ALA to EDA or ETrA, respectively. In a Δ6 desaturase/Δ6 elongase pathway, EDA and ETrA would be considered "by-product fatty acids". Addition of a Δ8 desaturase to a Δ6 desaturase/Δ6 elongase pathway would provide a means to convert the "by-product fatty acids" EDA and ETrA back into the "intermediate fatty acids" DGLA and ETA, respectively.

Microbial Expression Systems, Cassettes and Vectors

The Δ8 desaturase genes and gene products described herein (i.e., EaD8Des1, EaD8Des2, EaD8Des3, EaD8Des4, EaD8S or other mutant enzymes, codon-optimized enzymes or homologs thereof) may be expressed in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors (e.g., constructs, plasmids) and DNA expression cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcription (e.g., a promoter), the gene coding sequence, and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Transcriptional control regions (also initiation control regions or promoters) which are useful to drive expression of the instant Δ8 desaturase ORFs in the desired microbial host cell are numerous and familiar to those skilled in the art. Virtually any promoter (i.e., native, synthetic, or chimeric) capable of directing expression of these genes in the selected host cell is suitable for the present invention, although transcriptional and translational regions from the host species are particularly useful. Expression in a microbial host cell can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest. As an example, when the host cell is yeast, transcriptional and translational regions functional in yeast cells are provided, particularly from the host species (e.g., see Patent Publication No. US-2006-0115881-A1, for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. In alternate embodiments, the 3'-region can also be synthetic, as one of skill in the art can utilize available information to design and synthesize a 3'-region sequence that functions as a transcription terminator. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the genome of the host cell; the final cellular location of the synthesized foreign protein; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell. Each of these types of modifications are encompassed in the present invention, as means to further optimize expression of the Δ8 desaturases described herein.

Transformation of Microbial Host Cells

Once a DNA cassette that is suitable for expression in an appropriate microbial host cell has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a microbial host cell by any standard technique. These techniques include transformation (e.g., lithium acetate transformation [*Methods in Enzymology,* 194:186-187 (1991)]), protoplast fusion, bolistic impact, electroporation, microinjection, or any other method that introduces the gene(s) of interest into the host cell.

For convenience, a host cell that has been manipulated by any method to take up a DNA sequence (e.g., an expression cassette) will be referred to as "transformed", "transformant" or "recombinant" herein. The transformed host will have at least one copy of the expression construct and may have two or more, depending upon whether the expression cassette is integrated into the genome or is present on an extrachromosomal element having multiple copy numbers.

The transformed host cell can be identified by various selection techniques, as described in U.S. Pat. Nos. 7,238,482 and 7,259,255 and PCT Publication No. WO 2006/052870.

Following transformation, substrates suitable for the instant Δ8 desaturases (and, optionally other PUFA enzymes that are co-expressed within the host cell) may be produced by the host either naturally or transgenically, or they may be provided exogenously.

Preferred Microbial Host Cells for Recombinant Expression

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. The genes described in the instant invention have been expressed in an oleaginous yeast (an oleaginous stain of *Yarrowia lipolytica*); however, it is contemplated that because transcription, translation and the protein biosynthetic apparatus are highly conserved, any bacteria, yeast, algae, euglenoid, stramenopiles and/or fungus will be a suitable microbial host for expression of the present nucleic acid fragments.

Preferred microbial hosts are oleaginous organisms, such as oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as comprising strains that may be oleaginous include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*). In alternate embodiments, oil biosynthesis may be genetically engineered such that the microbial host cell (e.g., a yeast) can produce more than 25% oil of the cellular dry weight, and thereby be considered oleaginous.

Preferred oleaginous yeasts are oleaginous strains of *Yarrowia lipolytica* where particularly preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

Specific teachings applicable for transformation of oleaginous yeasts (i.e., *Yarrowia lipolytica*) include U.S. Pat. No. 4,880,741, U.S. Pat. No. 5,071,764 and Chen, D. C. et al. (*Appl. Microbiol. Biotechnol.*, 48(2):232-235 (1997)). Specific teachings applicable for engineering ARA, EPA and DHA production in *Y. lipolytica* are provided in U.S. patent application Ser. No. 11/264,784, U.S. patent application Ser. No. 11/265,761, and U.S. patent application Ser. No. 11/264,737 respectively.

The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (U.S. Pat. No. 7,214,491), the Lip1 gene locus (GenBank Accession No. Z50020), the Lip2 gene locus (GenBank Accession No. AJ012632), and/or the Pex10 gene locus (GenBank Accession No. CAG81606.

Preferred selection methods for use in *Yarrowia lipolytica* are resistance to kanamycin, hygromycin and the amino glycoside G418, as well as ability to grow on media lacking uracil, leucine, lysine, tryptophan or histidine. Additionally 5-fluoroorotic acid (5-fluorouracil-6-carboxylic acid monohydrate; "5-FOA") may be used for selection of yeast $Ura^-$ mutants. The compound is toxic to yeast cells that possess a functioning URA3 gene encoding orotidine 5'-monophosphate decarboxylase (OMP decarboxylase) and, because of this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997; see also PCT Publication No. WO 2006/052870 for 5-FOA use in *Yarrowia*).

An alternate preferred selection method for use in *Yarrowia* relies on a dominant, non-antibiotic marker for *Yarrowia lipolytica* based on sulfonylurea (chlorimuron ethyl; E. I. duPont de Nemours & Co., Inc., Wilmington, Del.) resistance. More specifically, the marker gene is a native acetohydroxyacid synthase (AHAS or acetolactate synthase; E.C. 4.1.3.18) that has a single amino acid change (W497L) that confers sulfonyl urea herbicide resistance (PCT Publication No. WO 2006/052870). AHAS is the first common enzyme in the pathway for the biosynthesis of branched-chain amino acids (i.e., valine, leucine, isoleucine) and it is the target of the sulfonylurea and imidazolinone herbicides.

Other preferred microbial hosts include oleaginous bacteria, algae, euglenoids, stramenopiles and other fungi, may of which may be genetically engineered for the production of omega-3 fatty acids. Thus, for example, transformation of *Mortierella alpina* (which is commercially used for production of ARA) with any of the present Δ8 desaturase genes under the control of inducible or regulated promoters could yield a transformant capable of synthesizing increased quantities of DGLA. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium, Schizochytrium*) are disclosed in U.S. Pat. No. 7,001,772.

Irrespective of the host selected for expression of the Δ8 desaturases described herein, it may be necessary to screen multiple transformants to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

Accordingly the scope of the present invention includes a method of producing either DGLA or ETA, respectively, comprising:

(a) providing an oleaginous yeast (e.g., *Yarrowia lipolytica*) comprising:
  (i) a first recombinant nucleotide molecule encoding a Δ8 desaturase polypeptide, operably linked to at least one regulatory sequence; and,
  (ii) a source of desaturase substrate consisting of EDA and/or ETrA, respectively; and,
(b) growing the yeast of step (a) in the presence of a suitable fermentable carbon source wherein the gene encoding the Δ8 desaturase polypeptide is expressed and EDA is converted to DGLA and/or ETrA is converted to ETA, respectively; and,
(c) optionally recovering the DGLA and/or ETA, respectively, of step (b). Substrate feeding may be required.

The nucleotide sequence of the gene encoding a Δ8 desurase may be selected from the group consisting of SEQ ID NO:17, SEQ ID NO:18, SEQ ID NO:19 and SEQ ID NO:20.

In alternate embodiments, the nucleotide sequence of the gene encoding a Δ8 desaturase polypeptide is set forth in SEQ ID NO:39 (wherein at least 208 codons have been optimized for expression in *Yarrowia* relative to SEQ ID NO:19).

Since naturally produced PUFAs in oleaginous yeast are limited to 18:2 fatty acids (i.e., LA), and less commonly, 18:3 fatty acids (i.e., ALA), the oleaginous yeast will be genetically engineered to express multiple enzymes necessary for long-chain PUFA biosynthesis (thereby enabling production of e.g., ARA, EPA, DPA and DHA), in addition to the Δ8 desaturases described herein. Specifically, in one embodiment this invention concerns an oleaginous yeast comprising:

(a) a first recombinant DNA construct comprising an isolated polynucleotide encoding a Δ8 desaturase polypeptide, operably linked to at least one regulatory sequence; and, (b) at least one additional recombinant DNA construct comprising an isolated polynucleotide, operably linked to at least one regulatory sequence, encoding a polypeptide selected from the group consisting of: a Δ4 desaturase, a Δ5 desaturase, a Δ6 desaturase, a Δ9 desaturase, a Δ12 desaturase, a Δ15 desaturase, a Δ17 desaturase, a Δ9 elongase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having delta-9 elongase activity.

Metabolic Engineering of Omega-3 and/or Omega-6 Fatty Acid Biosynthesis in Microbes Knowledge of the sequences of the present Δ8 desaturases will be useful for manipulating ω-3 and/or ω-6 fatty acid biosynthesis in various host cells. Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This manipulation may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in U.S. Patent Publication No. 2006-0094092-A1, U.S. Patent Publication No. 2006-0115881-A1, and U.S. Patent Publication No. 2006-0110806-A1, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the Δ9 elongase/Δ8 desaturase biosynthetic pathway are introduced into oleaginous yeasts for the production of ω-3 and/or ω-6 fatty acids. It will be particularly useful to express the present the Δ8 desaturase genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

Microbial Fermentation Processes for PUFA Production

The transformed microbial host cell is grown under conditions that optimize expression of chimeric desaturase and elongase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in U.S. Pat. No. 7,238,482. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in U.S. Pat. No. 7,238,482, as are various suitable fermentation process designs (i.e., batch, fed-batch and continuous) and considerations during growth.

Purification and Processing of PUFA Oils

PUFAs may be found in the host microorganisms as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology,* 12(5/6):463-491 (1992)). A brief review of downstream processing is also available by A. Singh and O. Ward (*Adv. Appl. Microbiol.,* 45:271-312 (1997)).

In general, means for the purification of PUFAs may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. One is referred to the teachings of U.S. Pat. No. 7,238,482 for additional details.

PUFA-Containing Oils for Use in Foodstuffs, Health Food Products, Pharmaceuticals and Animal Feeds The market place currently supports a large variety of food and feed products, incorporating ω-3 and/or ω-6 fatty acids (particularly e.g., ALA, GLA, ARA, EPA, DPA and DHA). It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils of the invention containing ω-3 and/or ω-6 fatty acids will be suitable for use in a variety of food and feed products including, but not limited to: food analogs, meat products, cereal products, baked foods, snack foods and dairy products (see Patent Publication No. US-2006-0094092 for details).

Additionally, the present compositions may be used in formulations to impart health benefit in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by: 1.) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and, 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" or "hr" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature for Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica:*

*Yarrowia lipolytica* strains with ATCC Accession Nos. #20362, #76982 and #90812 were purchased from the American Type Culture Collection (Rockville, Md.). *Yarrowia lipolytica* strains were typically grown at 28-30° C. in several media, according to the recipes shown below. Agar plates were prepared as required by addition of 20 g/L agar to each liquid media, according to standard methodology.

YPD agar medium (per liter): 10 g of yeast extract [Difco], 20 g of Bacto peptone [Difco]; and 20 g of glucose.

Basic Minimal Media (MM) (per liter): 20 g glucose; 1.7 g yeast nitrogen base without amino acids; 1.0 g proline; and pH 6.1 (not adjusted).

Minimal Media+Leucine (MM+leucine or MMLeu) (per liter): Prepare MM media as above and add 0.1 g leucine.

Minimal Media+Leucine+Uracil (MMLeuUra) (per liter): Prepare MM media as above and add 0.1 g leucine, 0.1 g uracil and 0.1 g uridine.

Minimal Media+5-Fluoroorotic Acid (MM+5-FOA) (per liter): 20 g glucose, 6.7 g Yeast Nitrogen base, 75 mg uracil, 75 mg uridine and appropriate amount of FOA (Zymo Research Corp., Orange, Calif.), based on FOA activity testing against a range of concentrations from 100 mg/L to 1000 mg/L (since variation occurs within each batch received from the supplier).

High Glucose Media (HGM) (per liter): 80 glucose, 2.58 g $KH_2PO_4$ and 5.36 g $K_2HPO_4$, pH 7.5 (do not need to adjust).

Transformation of *Yarrowia lipolytica* was performed according to the method of Chen, D. C. et al. (*Appl. Microbiol. Biotechnol.,* 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer, comprising: 2.25 mL of 50% PEG, average MW 3350; 0.125 mL of 2 M lithium acetate, pH 6.0; 0.125 mL of 2 M DTT; and (optionally) 50 μg sheared salmon sperm DNA. Then, approximately 500 ng of linearized plasmid DNA (or 100 ng circular plasmid) was incubated in 100 μL of resuspended cells, and maintained at 39° C. for 1 h with vortex mixing at 15 min intervals. The cells were plated onto selection media plates and maintained at 30° C. for 2 to 3 days.

Fatty Acid Analysis of *Yarrowia lipolytica:*

Unless otherwise stated, for fatty acid analysis cells were collected by centrifugation and lipids were extracted as described in Bligh, E. G. & Dyer, W. J. (*Can. J. Biochem. Physiol.,* 37:911-917 (1959)). Fatty acid methyl esters were prepared by transesterification of the lipid extract with sodium methoxide (Roughan, G. and Nishida I., *Arch Biochem Biophys.,* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, Yarrowia culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Construction of *Yarrowia lipolytica* Strain Y4001U:

*Y. lipolytica* strain Y4001U was used as the host in Example 7, infra. The following description is a summary of the construction of strain Y4001U, derived from *Yarrowia lipolytica* ATCC #20362, capable of producing about 17% EDA relative to the total lipids via expression of a Δ9 elongase/Δ8 desaturase pathway and having a Leu- and Ura-phenotype (FIG. 2A).

The development of strain Y4001U required the construction of strain Y2224 (a FOA resistant mutant from an autonomous mutation of the Ura3 gene of wildtype *Yarrowia* strain ATCC #20362) and strain Y4001 (producing 17% EDA with a Leu-phenotype).

Generation Of Strain Y2224: Strain Y2224 was isolated in the following manner: *Yarrowia lipolytica* ATCC #20362 cells from a YPD agar plate were streaked onto a MM plate (75 mg/L each of uracil and uridine, 6.7 g/L YNB with ammonia sulfate, without amino acids, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Generation Of Strain Y4001 To Produce About 17% EDA Of Total Lipids: Strain Y4001 was created via integration of construct pZKLeuN-29E3 (FIG. 2B). This construct, comprising four chimeric genes (i.e., a Δ12 desaturase, a $C_{16/18}$ elongase and two Δ9 elongases), was integrated into the Leu2 loci of strain Y2224 to thereby enable production of EDA.

Construct pZKLeuN-29E3 contained the components shown below in Table 4.

TABLE 4

Description of Plasmid pZKLeuN-29E3 (SEQ ID NO: 42)

| RE Sites And Nucleotides Within SEQ ID NO: 42 | Description Of Fragment And Chimeric Gene Components |
|---|---|
| BsiW I/Asc I (7797-7002) | 788 bp 3' portion of *Yarrowia* Leu2 gene (GenBank Accession No. AF260230) |
| Sph I/Pac I (4302-3591) | 703 bp 5' portion of *Yarrowia* Leu2 gene (GenBank Accession No. AF260230) |
| Swa I/BsiW I (10533-7797) | GPD::FmD12::Pex20, comprising:<br>GPD: *Yarrowia lipolytica* GPD promoter (U.S. Pat. No. 7,259,255);<br>FmD12: *Fusarium moniliforme* Δ12 desaturase gene (SEQ ID NO: 43) (labeled as "F.D12" in Figure; PCT Publication No. WO 2005/047485);<br>Pex20: Pex20 terminator sequence from *Yarrowia* Pex20 gene (GenBank Accession No. AF054613) |
| Bgl II/Swa I (12559-10533) | EXP1::EgD9eS::Lip1, comprising:<br>EXP1: *Yarrowia lipolytica* export protein (EXP1) promoter (labeled as "Exp pro" in Figure; PCT Publication No. WO 2006/052870 and U.S. Patent Application No. 11/265,761);<br>EgD9eS: codon-optimized Δ9 elongase (SEQ ID NO: 45), derived from *Euglena gracilis* (labeled as "EgD9E" in FIGURE; PCT Publication No. WO 2007/061742);<br>Lip1: Lip1 terminator sequence from *Yarrowia* Lip1 gene (GenBank Accession No. Z50020) |
| Pme I/Cla I (12577-1) | FBAINm::EgD9eS::Lip2, comprising:<br>FBAINm: *Yarrowia lipolytica* FBAINm promoter (U.S. Pat. No. 7,202,356);<br>EgD9eS: codon-optimized Δ9 elongase gene (SEQ ID NO: 45), derived from *Euglena gracilis* (labeled as "EgD9ES" in FIGURE; PCT Publication No. WO 2007/061742);<br>Lip2: Lip2 terminator sequence from *Yarrowia* Lip2 gene (GenBank Accession No. AJ012632) |
| Cla I/EcoR I (1-1736) | LoxP::Ura3::LoxP, comprising:<br>LoxP sequence (SEQ ID NO: 47);<br>*Yarrowia* Ura3 gene (GenBank Accession No. AJ306421);<br>LoxP sequence (SEQ ID NO: 47) |
| EcoR I/Pac I (1736-3591) | YAT1::ME3S::Pex16, comprising:<br>YAT1: *Yarrowia lipolytica* YAT1 promoter (labeled as "YAT" in FIGURE; Patent Publication No. U.S. 2006/0094102-A1);<br>ME3S: codon-optimized $C_{16/18}$ elongase gene (SEQ ID NO: 48), derived from *M. alpina* (PCT Publication No. WO 2007/046817);<br>Pex16: Pex16 terminator sequence of *Yarrowia* Pex 16 gene (GenBank Accession No. U75433) |

Plasmid pZKLeuN-29E3 was digested with AscI/SphI, and then used for transformation of *Y. lipolytica* strain Y2224 (i.e., ATCC #20362 Ura3-) according to the General Methods. The transformant cells were plated onto MMLeu media plates and maintained at 30° C. for 2 to 3 days. The colonies were picked and streaked onto MM and MMLeu selection plates. The colonies that could grow on MMLeu plates but not on MM plates were selected as Leu-strains. Single colonies of Leu-strains were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EDA in the transformants containing the 4 chimeric genes of pZKLeuN-29E3, but not in the *Yarrowia* Y2224 control strain. Most of the selected 36 Leu-strains produced about 12 to 16.9% EDA of total lipids. There were 3 strains (i.e., strains #11, #30 and #34) that produced about 17.4%, 17% and 17.5% EDA of total lipids; they were designated as strains Y4001, Y4002 and Y4003, respectively.

Single colonies of Y4001, Y4002 and Y4003 strains were inoculated in liquid MMLeu at 30° C. and shaken at 250 rpm/min for 2 days. The cells were collected by centrifugation, resuspended in High Glucose Media and then shaken at 250 rpm/min for 5 days. The cells were collected by centrifugation, lipids were extracted, and fatty acid methyl esters were prepared by trans-esterification, and subsequently analyzed with a Hewlett-Packard 6890 GC. GC analyses showed that the Y4001, Y4002 and Y4003 strains produced about 24% EDA of total lipids.

Generation Of Strain Y4001U (Leu-, Ura-): Strain Y4001U was created via temporary expression of the Cre recombinase enzyme in plasmid pY116 (FIG. 2C) within strain Y4001 to produce a Leu- and Ura-phenotype. Construct pY116 contained the following components:

TABLE 5

Description of Plasmid pY116 (SEQ ID NO: 50)

| RE Sites And Nucleotides Within SEQ ID NO: 50 | Description Of Fragment And Chimeric Gene Components |
|---|---|
| 1328-448 | ColE1 plasmid origin of replication |
| 2258-1398 | Ampicillin-resistance gene ($Amp^R$) for selection in *E. coli* |
| 3157-4461 | *Yarrowia* autonomous replication sequence (ARS18; GenBank Accession No. A17608) |
| SwaI/PacI 6667-4504 | *Yarrowia* Leu2 gene (GenBank Accession No. AF260230) |
| Swa I/Pme I (6667-218) | GPAT::Cre::XPR2, comprising:<br>GPAT: *Yarrowia lipolytica* GPAT promoter (U.S. Pat. No. 7,264,949);<br>Cre: Enterobacteria phage P1 Cre gene for recombinase protein (GenBank Accession No. X03453);<br>XPR2: ~100 bp of the 3' region of the *Yarrowia* Xpr gene (GenBank Accession No. M17741) |

Plasmid pY116 was used for transformation of freshly grown Y4001 cells according to the General Methods. The transformant cells were plated onto MMLeuUra plates containing 280 μg/mL sulfonylurea (chlorimuron ethyl, E. I. duPont de Nemours & Co., Inc., Wilmington, Del.) and maintained at 30° C. for 3 to 4 days. Four colonies were picked, inoculated into 3 mL liquid YPD media at 30° C. and shaken at 250 rpm/min for 1 day. The cultures were diluted to 1:50,000 with liquid MMLeuUra media, and 100 μL was plated onto new YPD plates and maintained at 30° C. for 2 days. Colonies were picked and streaked onto MMLeu and MMLeuUra selection plates. The colonies that could grow on MMLeuUra plates but not on MMLeu plates were selected and analyzed by GC to confirm the presence of C20:2 (EDA). Several strains, having a Leu- and Ura-phenotype, produced about 17% EDA of total lipids and were designated collectively as Y4001U; one of these strains was designated as Y4001U1.

Example 1

Synthesis of a cDNA Library From *Euglena anabaena* UTEX 373

The present Example describes the synthesis of a cDNA library from *Euglena anabaena* UTEX 373. This work included preparation of RNA, synthesis of cDNA, and generation of a cDNA library.

Growth of *Euglena anabaena* UTEX 373 and Preparation of RNA

*Euglena anabaena* UTEX 373 was obtained from Dr. Richard Triemer's lab at Michigan State University (East Lansing, Mich.). Approximately 2 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this step, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Catalog No. 24152). The oven temperature was programmed to hold at 170° C. for 1.0 min, increase to 240° C. at 5° C./min and then hold for an additional 1.0 min. Carrier gas was supplied by a Whatman hydrogen generator. Retention times were compared to those for methyl esters of standards commercially available (Nu-Chek Prep, Inc. Catalog No. U-99-A) and the resulting chromatogram is shown in FIG. 3. The presence of EDA, ERA, EPA and DHA in the fatty acid profile, with the absence of GLA and STA, suggested that *Euglena anabaena* uses the Δ9 elongase/Δ8 desaturase pathway for long-chain (LC) PUFA biosynthesis and would be a good source for LC-PUFA biosynthetic genes such as, but not limited to, Δ8 desaturases.

The remaining 5 mL of an actively growing culture was transferred into 25 mL of AF-6 Medium (Watanabe & Hiroki, NIES-Collection List of Strains, $5^{th}$ ed., National Institute for Environmental Studies, Tsukuba, 127 pp (2004)) in a 125 mL glass flask. *Euglena anabaena* cultures were grown at 22° C. with a 16 h light, 8 h dark cycle for 2 weeks with very gentle agitation.

After 2 weeks, the culture (25 mL) was transferred to 100 mL of AF-6 medium in a 500 mL glass bottle and the culture was grown for 1 month as described above. After this time, two 50 mL aliquots were transferred into two separate 500 mL glass bottles containing 250 mL of AF-6 medium and the cultures were grown for two months as described above (giving a total of ~600 mL of culture). Next, the cultures were pelleted by centrifugation at 1,800×g for 10 min, washed once with water and re-centrifuged. Total RNA was extracted from one of the resulting pellets using the RNA STAT-60™ reagent (TEL-TEST, Inc., Friendswood, Tex.) and following the manufacturer's protocol provided (use 5 mL of reagent, dissolved RNA in 0.5 mL of water). In this way, 340 μg of total RNA (680 ug/mL) was obtained from the pellet. The remaining pellet was frozen in liquid nitrogen and stored at −80° C. The mRNA was isolated from all 340 μg of total RNA using the mRNA Purification Kit (Amersham Biosciences, Piscataway, N.J.) following the manufacturer's protocol provided. In this way, 9.0 μg of mRNA was obtained.

Preparation of *Euglena anabaena* cDNA and Generation of cDNA Library eug1c

A cDNA library was generated using the Cloneminer™ cDNA Library Construction Kit (Catalog No. 18249-029, Invitrogen Corporation, Carlsbad, Calif.) and following the manufacturer's protocol provided (Version B, 25-0608). Using the non-radiolabeling method, cDNA was synthesized from 5.12 μg of mRNA (described above) using the Biotin-attB2-Oligo(dT) primer. After synthesis of the first and second strand, the attB1 adapter was added, ligated and the cDNA was size fractionated using column chromatography. DNA from fractions were concentrated, recombined into pDONR™222 and transformed into *E. coli* ElectroMAX™ DH10B™ T1 Phage-Resistant cells (Invitrogen Corporation). The *Euglena anabaena* library was named eug1c.

The cDNA library eug1c was plated onto LB+Kanamycin plates (approx. 100,000 colonies), the colonies were scraped off and DNA was isolated using the QIAprep® Spin Miniprep Kit (Qiagen Inc., Valencia, Calif.) following the manufacturer's protocol. In this way, a plasmid DNA sub-library from eug1c was obtained.

Example 2

Isolation of a cDNA Fragment Encoding a Partial Δ8 Desaturase From *Euglena anabaena* UTEX 373

The present Example describes the identification of a cDNA fragment (SEQ ID NO:1) encoding a partial Δ8 desaturase from *Euglena anabaena* UTEX 373, based on PCR amplification of the cDNA library using degenerate oligonucleotides based on a *Euglena gracilis* Δ8 desaturase sequence (SEQ ID NO:2).

Identification of cDNA Fragments Encoding Partial Putative Δ8 Desaturases

The plasmid DNA sub-library described in Example 1 was used as template for degenerate PCR using degenerate primers based on a nucleotide sequence of the *Euglena gracilis* Δ8 fatty acid desaturase (SEQ ID NO:2; described as Eg5 in PCT Publication No. WO 2006/012325) and the vector-specific primer pDonor222Eg5-1 (SEQ ID NO:3). The 4 degenerate primers used are shown in Table 6.

TABLE 6

Degenerate Oligonucleotides Used To Amplify A Portion Of The Δ8 Desaturase Genes From *Euglena anabaena* UTEX 373

| Primer | Nucleotide Sequence | SEQ ID NO: |
|---|---|---|
| D8DEG3-1 | RTTRTGNCKATCTTTCCACCA | SEQ ID NO:4 |
| D8DEG3-2 | RTTRTGNCKGTCTTTCCACCA | SEQ ID NO:5 |
| D8DEG3-3 | RTTRTGNCKATCCTTCCACCA | SEQ ID NO:6 |
| D8DEG3-4 | RTTRTGNCKGTCCTTCCACCA | SEQ ID NO:7 |

A total of 5 reactions were set up for the cDNA sample. The reaction mixture contained 1 μL of cDNA, 1 μL each of the vector-specific and degenerate primers (20 μM) and Phusion™ High-Fidelity DNA Polymerase (Catalog No. F553S, Finnzymes Oy, Finland). The PCR was carried out following the manufacturer's protocol. The resulting DNA fragments were cloned into the pCR-Blunt® cloning vector using the Zero Blunt® PCR Cloning Kit (Invitrogen Corporation), following the manufacturer's protocol.

Plasmid DNA from the resulting clones was purified using the QIAprep® Spin Miniprep Kit (Qiagen Inc.) following the manufacturer's protocol and DNA inserts were end-sequenced in 384-well plates, using vector-primed T7 primer (SEQ ID NO:8) and M13rev-28 primer (SEQ ID NO:9) with the ABI BigDye version 3 Prism sequencing kit. For the sequencing reaction, 100-200 ng of template and 6.4 pmol of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

A consensus sequence was assembled from the individual sequences obtained and one representative clone, designated as pHD23-1 (SEQ ID NO:10) having a sequence identical to the consensus was choosen for further study.

Identification of the partial cDNA insert in pHD23-1 (SEQ ID NO:1) as a partial Δ8 desaturase was confirmed using BLAST (Basic Local Alignment Search Tool; Altschul et al., *J. Mol. Biol.,* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The partial cDNA sequence obtained (SEQ ID NO:1) was translated in all reading frames and compared for similarity to all publicly available protein sequences contained in the "nr" database using the BLASTX algorithm (Gish and States, *Nat. Genet.,* 3:266-272 (1993)) provided by the NCBI with the default parameter and the filter turned off. For convenience, the P-value (probability) of observing a match of a cDNA sequence to a sequence contained in the searched databases merely by chance as calculated by BLAST are reported herein as a "pLog" value, which represents the negative of the logarithm of the reported P-value. Accordingly, the greater the pLog value, the greater the likelihood that the cDNA sequence and the BLAST "hit" represent homologous proteins.

The BLASTX search using the nucleotide sequence insert from pHD23-1 revealed similarity of the protein encoded by the partial cDNA (SEQ ID NO:1) to the *Euglena gracilis* Δ8 desaturase amino acid sequence (SEQ ID NO:11) (NCBI Accession No. AAD45877 (GI 5639724), locus AAD45877, CDS AF139720; Wallis and Browse, *Arch. Biochem. Biophys.,* 365:307-316 (1999)) and yielded a pLog value of 63.4 (E value of 4e-63).

Example 3

Isolation of Full-length Δ8 Desaturases from *Euglena anabaena* UTEX 373

Approximately 17,000 clones of cDNA library eug1c were plated onto three large square (24 cm×24 cm) petri plates (Corning, Corning, N.Y.) each containing LB+50 μg/mL kanamycin agar media. Cells were grown overnight at 37° C. and plates were then cooled to room temperature.

Colony Lifts

Biodyne B 0.45 μm membrane (Catalog No. 60207, Pall Corporation, Pensacola, Fla.) was trimmed to approximately 22 cm×22 cm and the membrane was carefully layed on top of the agar to avoid air bubbles. After incubation for 2 min at room temperature, the membrane was marked for orientation, lifted off with tweezers and placed colony-side up on filter paper soaked with 0.5 M sodium hydroxide and 1.5 M sodium chloride. After denaturation for 4 min, the sodium hydroxide was neutralized by placing the membrane on filter paper soaked with 0.5 M Tris-HCL (pH 7.5) and 1.5 M sodium chloride for 4 min. This step was repeated and the membrane was rinsed briefly in 2×SSC buffer (20×SSC is 3 M sodium chloride, 0.3 M sodium citrate; pH 7.0) and air dried on filter paper.

Hybridization

Membranes were pre-hybridized at 65° C. in 200 mL hybridization solution for 2 hr. Hybridization solution contained 6×SSPE (20×SSPE is 3 M sodium chloride, 0.2 M sodium phosphate, 20 mM EDTA; pH 7.4), 5×Denhardt's reagent (100×Denhardt's reagent is 2% (w/v) Ficoll, 2% (w/v) polyvinylpyrrolidone, 2% (w/v) acetylated bovine serum albumin), 0.5% sodium dodecyl sulfate (SDS), 100 μg/mL sheared salmon sperm DNA and 5% dextran sulfate.

A DNA probe was made using an agarose gel purified EcoRI DNA fragment, containing the *Euglena anabaena* Δ8 desaturase partial DNA fragment, from pHD23-1 (Example 2) labeled with $P^{32}$ dCTP using the RadPrime DNA Labeling System (Catalog No. 18428-011, Invitrogen, Carlsbad, Calif.) following the manufacturer's instructions. Unincorporated $P^{32}$ dCTP was separated using a NICK column (Catalog No. 17-0855-02, Amersham Biosciences, Piscataway, N.J.) following the manufacturer's instructions. The probe was denatured for 5 min at 100° C., placed on ice for 3 min and half was added to the hybridization solution.

The membrane was hybridized with the probe overnight at 65° C. with gentle shaking and then washed the following day twice with 2×SSC containing 0.5% SDS (5 min each) and twice with 0.2×SSC containing 0.1% SDS (15 min each). After washing, hyperfilm (Catalog No. RPN30K, Amersham Biosciences, Piscataway, N.J.) was exposed to the membrane overnight at −80° C.

Based on alignment of plates with the exposed hyperfilm, positive colonies were picked using the blunt end of a Pasteur pipette into 1 mL of water and vortexed. Several dilutions were made and plated onto small round Petri dishes (82 mm) containing LB media plus 50 μg/mL kanamycin to obtain around 100 well isolated colonies on a single plate. Lifts were done as described above except NytranN membrane circles (Catalog No. 10416116, Schleicher & Schuell, Keene, N.H.) were used and hybridization was carried out in 100 mL using the remaining radiolabeled probe. In this way, positive clones were confirmed.

Individual positive clones were grown at 37° C. in LB+50 μg/mL kanamycin liquid media and plasmid was purified using the QIAprep® Spin Miniprep Kit (Qiagen Inc.) following the manufacturer's protocol.

The plasmid insert was sequenced as described in Example 2 with the ABI BigDye version 3 Prism sequencing kit using vector-primed T7 primer (SEQ ID NO:8), vector-primed M13rev-28 primer (SEQ ID NO:9) and the poly(A) tail-primed WobbleT oligonucleotides. Briefly, the WobbleT primer is an equimolar mix of 21 mer poly(T)A, poly(T)C and poly(T)G, used to sequence the 3' end of cDNA clones. Based on initial sequence data, additional internal fragment sequence was obtained in a similar way using oligonucleotide EaD8seq-1 (SEQ ID NO:12). In this way, the full insert sequences of the eug1c Δ8 desaturase clones were obtained.

Sequences were aligned and compared using Sequencher™ (Version 4.2, Gene Codes Corporation, Ann Arbor, Mich.) and in this way, the clones could be categorized into one of four distinct groups based on insert sequence (designated as EaD8Des1, EaD8Des2, EaD8Des3 or EaD8Des4). Representative clones containing the cDNA for each class of sequence were chosen for further study and sequences for each representative plasmid (i.e., pLF118-1, pLF118-2, pLF118-3 and pLF118-4) are shown in SEQ ID NO:13, SEQ ID NO:14, SEQ ID NO:15 and SEQ ID NO:16, respectively. The sequence shown by a string of NNNN's represents a region of the polyA tail which was not sequenced. The coding sequences for EaD8Des1, EaD8Des2, EaD8Des3 and EaD8Des4 are shown in SEQ ID NO:17, SEQ ID NO:18, SEQ ID NO:19 and SEQ ID NO:20, respectively. The corresponding amino acid sequences for EaD8Des1, EaD8Des2, EaD8Des3 and EaD8Des4 are shown in SEQ ID NO:21, SEQ ID NO:22, SEQ ID NO:23 and SEQ ID NO:24, respectively. EaD8Des1, EaD8Des2, EaD8Des3 and EaD8Des4 are collectively referred to as EaD8Des genes.

Example 4

Primary Sequence Analysis of the Δ8 Desaturase Sequences of *Euglena anabaena* UTEX 373 and Comparison to a Δ8 Desaturase Sequence of *Euglena gracilis*

The amino acid sequences for EaD8Des1 (SEQ ID NO:21), EaD8Des2 (SEQ ID NO:22), EaD8Des3 (SEQ ID NO:23) and EaD8Des4 (SEQ ID NO:24) were compared using the Clustal W method (using the MegAlign™ v 6.1 program of the LASERGENE bioinformatics computing suite (DNASTAR Inc.) with the default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB).

Compared to EaD8Des1 (SEQ ID NO:21), EaD8Des2 (SEQ ID NO:22) has 3 amino acid substitutions (i.e., T110S, M223I and K251T; based on numbering for EaD8Des1), EaD8Des3 (SEQ ID NO:23) has 2 amino acid substitutions (i.e., T110S and K251T) and EaD8Des4 (SEQ ID NO:24) has 1 amino acid substitution (i.e., T110S).

The amino acid sequences for EaD8Des1 (SEQ ID NO:21), EaD8Des2 (SEQ ID NO:22), EaD8Des3 (SEQ ID NO:23) and EaD8Des4 (SEQ ID NO:24) were evaluated by BLASTP (Basic Local Alignment Search Tool; Altschul et al., *J. Mol. Biol.,* 215:403-410 (1993)) searches for similarity to sequences contained in the BLAST "nr" database (supra, Example 2) using default parameters and the filter off. For convenience, the P-value (probability) of observing a match of a cDNA sequence to a sequence contained in the searched databases merely by chance as calculated by BLAST are reported herein as "pLog" values, which represent the negative of the logarithm of the reported P-value.

All four sequences yielded a pLog value of 177 (P value of e-177) versus the *Euglena gracilis* Δ8 desaturase amino acid sequence (SEQ ID NO:11) (NCBI Accession No. AAD45877 (GI 5639724), locus AAD45877, CDS AF139720; Wallis and Browse, *Arch. Biochem. Biophys.,* 365:307-316 (1999)) when compared to the "nr" database. BLAST scores and probabilities indicate that the instant nucleic acid fragments encode entire *Euglena anabaena* Δ8 fatty acid desaturases.

The amino acid sequences for EaD8Des1 (SEQ ID NO:21), EaD8Des2 (SEQ ID NO:22), EaD8Des3 (SEQ ID NO:23) and EaD8Des4 (SEQ ID NO:24) were then compared to a functional variant *Euglena gracilis* Δ8 desaturase amino acid sequence (identified herein as EgD8 and set forth as SEQ ID NO:25; described as Eg5 in PCT Application No. WO 2006/012325) using BlastP (default parameters, filter off), Clustal V and the Jotun Hein methods of sequence comparison and the % identity using each method is shown in Table 7.

Sequence percent identity calculations performed by the Clustal V method (Higgins, D. G. and Sharp, P. M., *Comput. Appl. Biosci.,* 5:151-153 (1989); Higgins et al., *Comput. Appl. Biosci.,* 8:189-191 (1992)) were done using the MegAlign™ v 6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). Sequence percent identity calculations performed by the Jotun Hein method (Hein, J. J., *Meth. Enz.,* 183:626-645 (1990)) were done using the MegAlign™ v 6.1 program of the LASERGENE bioinformatics computing suite (DNASTAR Inc., Madison, Wis.) with the default parameters for pairwise alignment (KTUPLE=2).

TABLE 7

Sequence Comparison Of EaD8Des1 (SEQ ID NO: 21), EaD8Des2 (SEQ ID NO: 22), EaD8Des3 (SEQ ID NO: 23) And EaD8Des4 (SEQ ID NO: 24) To EgD8 (SEQ ID NO: 25)

| Desaturase | % Identity to EgD8 (SEQ ID NO: 25) by BLASTP | % Identity to EgD8 (SEQ ID NO: 25) by the Jotun Hein Method | % Identity to EgD8 (SEQ ID NO: 25) by the Clustal V Method |
|---|---|---|---|
| EaD8Des1 | 73% | 74.4% | 72.1% |
| EaD8Des2 | 73% | 74.2% | 71.9% |
| EaD8Des3 | 73% | 74.2% | 71.9% |
| EaD8Des4 | 73% | 74.2% | 71.9% |

The Clustal V alignment of these five amino acid sequences can be seen in FIGS. 4A, 4B and 4C. Table 8 below sets forth a comparison of the percent identity (shown in the upper half triangle) and percent divergence (shown in the lower half triangle), among the five Δ8 desaturase sequences aligned in FIGS. 4A, 4B and 4C.

TABLE 8

Percent Identity And Percent Divergence Among EaD8Des1 (SEQ ID NO: 21), EaD8Des2 (SEQ ID NO: 22), EaD8Des3 (SEQ ID NO: 23), EaD8Des4 (SEQ ID NO: 24) And EgD8 (SEQ ID NO: 25)

| | EaD8Des1 | EaD8Des2 | EaD8Des3 | EaD8Des4 | EgD8 |
|---|---|---|---|---|---|
| EaD8Des1 | — | 99.3 | 99.5 | 99.8 | 72.1 |
| EaD8Des2 | 0.7 | — | 99.8 | 99.5 | 71.9 |
| EaD8Des3 | 0.5 | 0.2 | — | 99.8 | 71.9 |
| EaD8Des4 | 0.2 | 0.5 | 0.2 | — | 71.9 |
| EgD8 | 31.4 | 31.8 | 31.8 | 31.8 | — |

Example 5

Functional Analysis of the *Euglena anabaena* UTEX 373 Δ8 Desaturases in *Yarrowia lipolytica*

The present Example describes functional analysis of EaD8Des1 (SEQ ID NO:21), EaD8Des2 (SEQ ID NO:22), EaD8Des3 (SEQ ID NO:23) and EaD8Des4 (SEQ ID NO:24) in *Yarrowia lipolytica*. This work included the following steps: (1) PCR amplification of each Δ8 desaturase with appropriate restriction sites for cloning from the plasmids described in Example 2; (2) cloning of the EaD8Des PCR products into cloning vector pCR-Blunt® (Invitrogen Corporation) to produce pY120-1, pY120-2, pY120-3 and pY120-4; (3) cloning of the EaD8Des genes into *Yarrowia* expression vector pY115 to produce pY175, pY176, pY177 and pY178; and, (4) comparison of lipid profiles within transformant organisms comprising pY175, pY176, pY177 and pY178, after substrate feeding.

PCR Amplification of the *Euglena anabaena* Δ8 Desaturase Genes

In order to introduce NotI and NcoI restriction sites at the 5' end of the coding sequences and a NotI site at the 3' end of the coding sequences, each of the EaD8Des genes were PCR amplified. The coding sequences for EaD8Des1 (SEQ ID NO:17), EaD8Des2 (SEQ ID NO:18), EaD8Des3 (SEQ ID NO:19) and EaD8Des4 (SEQ ID NO:20) were amplified from pLF118-1 (SEQ ID NO:13), pLF118-2 (SEQ ID NO:14), pLF118-3 (SEQ ID NO:15) and pLF118-4 (SEQ ID NO:16), respectively, with oligonucleotide primers EaD8-5 (SEQ ID NO:26) and EaD8-3 (SEQ ID NO:27) using the Phusion™ High-Fidelity DNA Polymerase (Catalog No. F553S, Finnzymes Oy, Finland) following the manufacturer's protocol. The resulting DNA fragments were cloned into the pCR-Blunt® cloning vector using the Zero Blunt® PCR Cloning Kit (Invitrogen Corporation), following the manufacturer's protocol, to produce pLF120-1 (SEQ ID NO:28), pLF120-2 (SEQ ID NO:29), pLF120-3 (SEQ ID NO:30) and pLF120-4 (SEQ ID NO:31), respectively.

Construction of *Yarrowia* Expression Vectors pY115, pY175, pY176, pY177 and pY178

Plasmid pY5-30 (described in U.S. Pat. No. 7,259,255) is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (AmpR), for selection in *E. coli*; a *Yarrowia* LEU2 gene, for selection in *Yarrowia*; and a chimeric TEF::GUS::XPR gene. Plasmid pDMW263 (SEQ ID NO:32) was created from pY5-30, by replacing the TEF promoter with the *Yarrowia lipolytica* FBAINm promoter (U.S. Pat. No. 7,202,356) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fbal gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 9 summarizes the components of pDMW263 (SEQ ID NO:32).

TABLE 9

Components Of Plasmid pDMW263

| RE Sites and Nucleotides Within SEQ ID NO: 32 | Description of Fragment and Chimeric Gene Components |
|---|---|
| 4992-4296 | ARS18 sequence (GenBank Accession No. A17608) |
| SalI/SacII (8505-2014) | FBAINm::GUS::XPR, comprising:<br>FBAINm: *Yarrowia lipolytica* FBAINm promoter (U.S. Pat. No. 7,202,356);<br>GUS: *E. coli* gene encoding β-glucuronidase (Jefferson, R. A. Nature, 14: 342: 837-838 (1989);<br>XPR: ~100 bp of the 3' region of the *Yarrowia* Xpr gene (GenBank Accession No. M17741) |
| 6303-8505 | *Yarrowia* Leu2 gene (GenBank Accession No. AF260230) |

The NcoI/SalI DNA fragment from pDMW263 (SEQ ID NO:32), containing the *Yarrowia lipolytica* FBAINm promoter, was cloned into the NcoI/SalI DNA fragment of pDMW237 (SEQ ID NO:33), previously described in PCT Publication No. WO 2006/012325 (the contents of which are hereby incorporated by reference), containing a synthetic Δ9 elongase gene derived from *Isochrysis galbana* and codon-optimized for expression in *Yarrowia lipolytica*, to produce pY115 (SEQ ID NO:34; FIG. 5A). In FIG. 5A and FIG. 5B, the modified FBAINm promoter is labeled as FBA1+Intron.

The NcoI/NotI DNA fragments from pLF120-1 (SEQ ID NO:28), pLF120-2 (SEQ ID NO:29), pLF120-3 (SEQ ID NO:30) and pLF120-4 (SEQ ID NO:31), containing each EaD8Des, were cloned into the NcoI/NotI DNA fragment from pY115, containing the *Yarrowia lipolytica* FBAINm promoter, to produce pY175 (SEQ ID NO:35; FIG. 5B), pY176 (SEQ ID NO:36), pY177 (SEQ ID NO:37) and pY178 (SEQ ID NO:38), respectively.

Functional Analysis of the *Euglena anabaena* Δ8 Desaturase Genes in *Yarrowia lipolytica* Strain Y2224

Strain Y2224 (see General Methods) was transformed with pY175 (SEQ ID NO:35), pY176 (SEQ ID NO:36), pY177 (SEQ ID NO:37) and pY178 (SEQ ID NO:38) as described in the General Methods.

Single colonies of transformant *Yarrowia lipolytica* containing pY175, pY176, pY177 and pY178 were grown in 3 mL minimal media lacking uracil supplemented with 0.2% tergitol at 30° C. for 1 day. After this, 0.1 mL was transferred to 3 mL of the same medium supplemented with EDA (20:2 (11,14)) or ETrA (20:3(11,14,17)) to 0.175 mM. These were incubated for 16 hr at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.,* 276(1):38-46 (1990)) with 500 μL of 1% sodium methoxide for 30 min at 50° C. after which 500 μL of 1 M sodium chloride and 100 μL of heptane were added. After thorough mixing and centrifugation, fatty acid methyl esters (FAMEs) were analyzed by GC. FAMEs (5 μL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for Yarrowia lipolytica expressing pY175, pY176, pY177 and pY178 are shown in FIG. 6. Percent C20 desaturation ("C20% delta-8 desat") was calculated either by dividing the weight percent (wt %) for DGLA by the sum of the wt % for EDA and DGLA and multiplying by 100 to express as a % or by dividing the wt % for ETA by the sum of the wt % for ERA and DTA and multiplying by 100 to express as a %, depending on which substrate was fed (i.e., EDA or ERA). Averages are indicated by Ave. followed by the appropriate header. The ratio of desaturation of EDA to ERA is calculated by dividing the Ave. C20% delta-8 desat for EDA by that of ERA.

All of the *Euglena anabaena* Δ8 desaturases function similarly well in *Yarrowia* and convert approximately 50% of the fed EDA to DGLA. There appears to be a slight preference for the EDA over ERA with a EDA/ERA ratio of 1.1 to 1.2.

Example 6

Synthesis of a Codon-Optimized Δ8 Desaturase Gene for *Yarrowia lipolytica* (EaD8S)

The codon usage of the Δ8 desaturase gene (EaD8Des3; SEQ ID NO:19) of *Euglena anabaena* was optimized for expression in *Yarrowia lipolytica*, in a manner similar to that described in PCT Publication No. WO 2004/101753 and U.S. Pat. No. 7,125,672. Specifically, a codon-optimized Δ8 desaturase gene (designated "EaD8S", SEQ ID NO:39) was designed based on the coding sequence of EaD8Des3 (SEQ ID NOs:19 and 23), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 231 bp of the 1260 bp coding region were modified (18.3%) and 208 codons were optimized (49.5%). The GC content was reduced from 56.8% within the wild type gene (i.e., EaD8Des3) to 54.8% within the synthetic gene (i.e., EaD8S). A NcoI site and NotI sites were incorporated around the translation initiation codon and after the stop codon of EaD8S (SEQ ID NO:39), respectively. FIGS. 7A and 7B show a comparison of the nucleotide sequences of EaD8Des3 (SEQ ID NO:19) and EaD8S (SEQ ID NO:39). The protein sequence encoded by the codon-optimized gene (i.e., SEQ ID NO:40) is identical to that of the wildtype EaD8Des3 protein sequence (i.e., SEQ ID NO:23). The designed EaD8S gene was synthesized by GenScript Corporation (Piscataway, N.J.) and cloned into pUC57 (GenBank Accession No. Y14837) to generate pEaD8S (SEQ ID NO:41; FIG. 8A).

Example 7

Construction and Functional Analysis of *Yarrowia lipolytica* Expression Vector pZUFmEaD8S, Comprising a Synthetic Δ8 Desaturase Gene (Derived from *Euglena anabaena*), Codon-Optimized for Expression in *Yarrowia lipolytica* (EaD8S)

The present Example describes the functional expression of *Yarrowia lipolytica* vector pZUFmEaD8S, comprising a chimeric FBAINm::EaD8S::Pex20 gene, wherein EaD8S is the synthetic Δ8 desaturase derived from *Euglena anabaena* and codon-optimized for expression in *Yarrowia* (Example 6). The plasmid pZUFmEaD8S (FIG. 8B) contained the following components:

TABLE 10

Components Of Plasmid pZUFmEaD8S (SEQ ID NO: 51)

| RE Sites And Nucleotides Within SEQ ID NO: 51 | Description Of Fragment And Chimeric Gene Components |
|---|---|
| Swa I/BsiW I (7333-1584) | FBAINm::EaD8S::Pex20, comprising:<br>FBAINm: *Yarrowia lipolytica* FBAIN promoter (U.S. Pat. No. 7,202,356)<br>EaD8S: codon-optimized Δ8 desaturase (SEQ ID NO: 39), derived from *Euglena anabaena*<br>Pex20: Pex20 terminator sequence of *Yarrowia* Pex20 gene (GenBank Accession No. AF054613) |

TABLE 10-continued

| Components Of Plasmid pZUFmEaD8S (SEQ ID NO: 51) | |
|---|---|
| RE Sites And Nucleotides Within SEQ ID NO: 51 | Description Of Fragment And Chimeric Gene Components |
| 2620-1740 | ColE1 plasmid origin of replication |
| 3550-2690 | Ampicillin-resistance gene ($Amp^R$) for selection in *E. coli* |
| 4449-5753 | *Yarrowia* autonomous replication sequence (ARS18; GenBank Accession No. A17608) |
| 7297-5796 | *Yarrowia* Ura 3 gene (GenBank Accession No. AJ306421) |

Functional Analysis of *Yarrowia lipolytica* Transformants Comprising pZUFmEaD8S Plasmid pZUFmEaD8S (SEQ ID NO:51; FIG. 8B) was transformed into strain Y4001U as described in the General Methods. The transformants were selected on MMLeu plates. After 2 days growth at 30° C., transformants were picked and re-streaked onto fresh MMLeu plates. Once grown, these strains were individually inoculated into 3 mL liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 6.5% DGLA and 9.4% EDA of total lipids produced in all 7 transformants, wherein the conversion efficiency of EDA to DGLA in these 7 strains was determined to be about 41%.

What is claimed is:

1. An isolated microbial host cell comprising an isolated polynucleotide comprising:

(a) a nucleotide sequence encoding a polypeptide having Δ8 desaturase activity, wherein the polypeptide has at least 90% amino acid identity, based on the Clustal V method of alignment, when compared to an amino acid sequence selected from the group consisting of: SEQ ID NO:21, SEQ ID NO:22, SEQ ID NO:23 and SEQ ID NO:24;

(b) a nucleotide sequence encoding a polypeptide having Δ8 desaturase activity, wherein the nucleotide sequence has at least 90% sequence identity, based on the BLASTN method of alignment, when compared to a nucleotide sequence selected from the group consisting of: SEQ ID NO:17, SEQ ID NO:18, SEQ ID NO:19, SEQ ID NO:20 and SEQ ID NO:39; or (c) a complement of the nucleotide sequence of (a) or (b), wherein the complement and the nucleotide sequence consist of the same number of nucleotides and are 100% complementary.

2. The microbial host cell of claim 1 wherein the isolated polynucleotide encodes an amino acid sequence selected from the group consisting of: SEQ ID NO:21, SEQ ID NO:22, SEQ ID NO:23 and SEQ ID NO:24.

3. The microbial host cell of claim 1 wherein the microbial host cell is selected from the group consisting of yeast, algae, bacteria, euglenoids, stramenopiles and fungi.

4. The microbial host cell of claim 3 wherein the cell is a fungus of the genus *Mortierella.*

5. The microbial host cell of claim 3 wherein the cell is a stramenopiles selected from the genus consisting of: *Thraustochytrium* and *Schizochytrium.*

6. The microbial host cell of claim 3 wherein the yeast is an oleaginous yeast.

7. The microbial host cell of claim 6 wherein the oleaginous yeast is selected from the group consisting of: *Yarrowia, Candida, Rhodotorula, Rhodosporidium, Cryptococcus, Trichosporon* and *Lipomyces.*

8. The microbial host cell of claim 1, wherein the isolated nucleic acid molecule encoding a polypeptide having Δ8 desaturase activity is set forth in SEQ ID NO:39 and wherein at least 208 codons of the encoded polypeptide are codon-optimized for expression in *Yarrowia* sp.

* * * * *